US009884895B2

(12) United States Patent
Baric et al.

(10) Patent No.: US 9,884,895 B2

(45) Date of Patent: Feb. 6, 2018

(54) METHODS AND COMPOSITIONS FOR CHIMERIC CORONAVIRUS SPIKE PROTEINS

(71) Applicant: The University of North Carolina at Chapel Hill, Chapel Hill, NC (US)

(72) Inventors: Ralph Baric, Haw River, NC (US); Sudhakar Agnihothram, Ellicott City, MD (US); Boyd Yount, Hillsborough, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/124,992

(22) PCT Filed: Mar. 20, 2015

(86) PCT No.: PCT/US2015/021773

§ 371 (c)(1),
(2) Date: Sep. 9, 2016

(87) PCT Pub. No.: WO2015/143335

PCT Pub. Date: Sep. 24, 2015

(65) Prior Publication Data

US 2017/0096455 A1 Apr. 6, 2017

Related U.S. Application Data

(60) Provisional application No. 61/968,279, filed on Mar. 20, 2014.

(51) Int. Cl.

| | |
|---|---|
| ***C07K 16/10*** | (2006.01) |
| ***A61K 39/12*** | (2006.01) |
| ***A61K 39/215*** | (2006.01) |
| ***A61K 39/395*** | (2006.01) |
| ***A61K 45/06*** | (2006.01) |
| ***C07K 14/005*** | (2006.01) |
| ***C12N 7/00*** | (2006.01) |
| *A61K 39/00* | (2006.01) |

(52) U.S. Cl.

CPC ............ *C07K 14/005* (2013.01); *A61K 39/12* (2013.01); *C07K 16/10* (2013.01); *C12N 7/00* (2013.01); *A61K 2039/5256* (2013.01); *A61K 2039/5258* (2013.01); *A61K 2039/70* (2013.01); *C07K 2317/34* (2013.01); *C07K 2317/76* (2013.01); *C12N 2770/20022* (2013.01); *C12N 2770/20034* (2013.01); *C12N 2770/36123* (2013.01); *C12N 2770/36143* (2013.01)

(58) Field of Classification Search

CPC .. A61K 39/12; A61K 2039/505; C07K 16/10; C07K 2317/76; C12N 2770/20034

See application file for complete search history.

(56) References Cited

U.S. PATENT DOCUMENTS

| | | | |
|---|---|---|---|
| 3,610,795 | A | 10/1971 | Antoine |
| 4,474,893 | A | 10/1984 | Reading |
| 4,676,980 | A | 6/1987 | Segal et al. |
| 4,816,567 | A | 3/1989 | Cabilly et al. |
| 5,879,881 | A | 3/1999 | Rubenstein |
| 2003/0073147 | A1 | 4/2003 | Alderete et al. |

FOREIGN PATENT DOCUMENTS

| | | | |
|---|---|---|---|
| WO | WO 93/23422 | A1 | 11/1993 |
| WO | WO 2005/002500 | A2 | 1/2005 |
| WO | WO 2005/081716 | A2 | 9/2005 |

OTHER PUBLICATIONS

Agnihothram et al. "Evaluation of Serologic and Antigenic Relationships Between Middle Eastern Respiratory Syndrome Coronavirus and Other Coronaviruses to Develop Vaccine Platforms for the Rapid Response to Emerging Coronaviruses" *The Journal of Infectious Diseases* 209:995-1006 (2014).
International Search Report and the Written Opinion of the International Searching Authority corresponding to International Patent Application No. PCT/US2015/021773 (12 pages) (dated Jun. 10, 2015).
GenBank Accession No. ACJ60694.1, "Spike glycoprotein [recombinant coronavirus]", *NCBI*, 2 pages, Jul. 26, 2016.
GenBank Accession No. AAP13441.1, "S protein [SARS coronavirus Urbani]", *NCBI*, 2 pages, Jul. 25, 2016.
GenBank Accession No. ABG47069, "Spike protein [Bat CoV 279/2005]", *NCBI*, 2 pages, Jul. 19, 2006.
GenBank Accession No. ABN10848.1, "Spike glycoprotein [Bat coronavirus HKU4-2]", *NCBI*, 2 pages, Feb. 7, 2007.
GenBank Accession No. AFS88936.1, "S protein [Human betacoronavirus 2c EMC/2012]", *NCBI*, 2 pages, Dec. 4, 2012.
GenBank Accession No. ABN10902.1, "Spike glycoprotein [Bat coronavirus HKU5-5]", *NCBI*, 2 pages, Feb. 7, 2007.
GenBank Accession No. FJ211859, "Recombinant coronavirus clone Bat SARS-CoV, complete sequence", *NCBI*, 11 pages, Jul. 26, 2016.
GenBank Accession No. FJ211860, "Recombinant coronavirus clone Bat-SRBD spike glycoprotein gene, complete cds", *NCBI*, 3 pages, Dec. 31, 2008.
GenBank Accession No. DQ022305, "Bat SARS coronavirus HKU3-1, complete genome", *NCBI*, 12 pages, Oct. 25, 2005.
GenBank Accession No. DQ084199, "Bat SARS coronavirus HKU3-2, complete genome", *NCBI*, 12 pages, Sep. 28, 2005.
GenBank Accession No. DQ084200, "Bat SARS coronavirus HKU3-3, complete genome", *NCBI*, 12 pages, Sep. 28, 2005.
GenBank Accession No. DQ412043, "Bat SARS coronavirus Rm1, complete genome", *NCBI*, 12 pages, Jul. 13, 2006.
GenBank Accession No. DQ648857, "Bat coronavirus (BtCoV/279/2005), complete genome", *NCBI*, 11 pages, Jul. 19, 2006.
GenBank Accession No. DQ412042, "Bat SARS coronavirus Rf1, complete genome", *NCBI*, 12 pages, Jul. 13, 2016.
GenBank Accession No. DQ648856, "Bat coronavirus (BtCoV/273/2005), complete genome", *NCBI*, 11 pages, Jul. 19, 2006.

(Continued)

*Primary Examiner* — Barry A Chestnut

(74) *Attorney, Agent, or Firm* — Myers Bigel, P.A.

(57) ABSTRACT

The present invention provides compositions and methods comprising a chimeric coronavirus spike protein.

23 Claims, 19 Drawing Sheets

(56) References Cited

OTHER PUBLICATIONS

GenBank Accession No. DQ071615, "Bat SARS coronavirus Rp3, complete genome", *NCBI*, 12 pages, Jan. 25, 2006.
GenBank Accession No. AY686863, "SARS coronavirus A022, complete genome", *NCBI*, 12 pages, Jul. 21, 2006.
GenBank Accession No. AY278554, "SARS coronavirus CUHK-W1, complete genome", *NCBI*, 14 pages, Jul. 31, 2003.
GenBank Accession No. AY278489, "SARS coronavirus GD01, complete genome", *NCBI*, 13 pages, Sep. 1, 2009.
GenBank Accession No. AY515512, "SARS coronavirus HC/SZ/61/03, complete genome", *NCBI*, 8 pages, Jan. 1, 2005.
Genbank accession No. AY304488, "SARS coronavirus SZ16, complete genome", *NCBI* 8 pages, Nov. 5, 2003.
GenBank Accession No. AY278741, "SARS coronavirus Urbani, complete genome", *NCBI* 14 pages, Jul. 25, 2016.
GenBank Accession No. AY572035, "SARS coronavirus civet010, complete genome", *NCBI*, 12 pages, Dec. 1, 2005.
GenBank Accession No. DQ497008, "SARS coronavirus strain MA-15, complete genome", *NCBI*, 13 pages, Mar. 20, 2007.
GenBank Accession No. KC881005, "Bat SARS-like coronavirus RsSHC014, complete genome", *NCBI*, 13 pages, Nov. 22, 2013.
GenBank Accession No. KC881006, Bat SARS-like coronavirus Rs3367, complete genome, *NCBI*, 13 pages, Nov. 22, 2013.
GenBank Accession No. KC881007, "Bat SARS-like coronavirus WIV1 spike protein (S) gene, complete cds", *NCBI*, 3 pages, Nov. 22, 2013.
GenBank Accession No. KF600652.1, "Middle East respiratory syndrome coronavirus isolate Riyadh_2_2012, complete genome", *NCBI*, 13 pages, Jul. 24, 2014.
GenBank Accession No. KF600651.1, "Middle East respiratory syndrome coronavirus isolate", *NCBI*, 13 pages, Jul. 24, 2014.
GenBank Accession No. KF600647.1, "Middle East respiratory syndrome coronavirus isolate Al-Hasa_17_2013, complete genome", *NCBI*, 13 pages, Jul. 24, 2014.
GenBank Accession No. KF600645.1, "Middle East respiratory syndrome coronavirus isolate Al-Hasa_15_2013, complete genome", *NCBI*, 13 pages, Jul. 24, 2014.
GenBank Accession No. KF600644.1, "Middle East respiratory syndrome coronavirus isolate Al-Hasa_16_2013, complete genome", *NCBI*, 13 pages, Jul. 24, 2014.
GenBank Accession No. KF600634, "Middle East respiratory syndrome coronavirus isolate Al-Hasa_21_2013, complete genome", *NCBI*, 13 pages, Jul. 24, 2014.
GenBank Accession No. KF600632, "Middle East respiratory syndrome coronavirus isolate Al-Hasa_19_2013, complete genome", *NCBI*, 13 pages, Jul. 24, 2014.
GenBank Accession No. KF600630.1, "Middle East respiratory syndrome coronavirus isolate Buraidah_1_2013, complete genome", *NCBI*, 13 pages, Jul. 24, 2014.
GenBank Accession No. KF600628.1, "Middle East respiratory syndrome coronavirus isolate Hafr-Al-Batin_1_2013, complete genome", *NCBI*, 13 pages, Jul. 24, 2014.
GenBank Accession No. KF600627.1, "Middle East respiratory syndrome coronavirus isolate Al-Hasa_12_2013, complete genome", *NCBI*, 13 pages, Jul. 24, 2014.
GenBank Accession No. KF600620.1, "Middle East respiratory syndrome coronavirus isolate Bisha_1_2012, complete genome", *NCBI*, 13 pages, Jul. 24, 2014.
GenBank Accession No. KF600613.1, "Middle East respiratory syndrome coronavirus isolate Riyadh_3_2013, complete genome", *NCBI*, 13 pages, Jul. 24, 2014.
GenBank Accession No. KF600612.1, "Middle East respiratory syndrome coronavirus isolate Riyadh_1_2012, complete genome", *NCBI*, 13 pages, Jul. 24, 2014.
GenBank Accession No. KF186565.1, "Middle East respiratory syndrome coronavirus isolate Al-Hasa_3_2013, complete genome", *NCBI*, 13 pages, Jul. 24, 2014.
GenBank Accession No. KF186567.1, "Middle East respiratory syndrome coronavirus isolate Al-Hasa_1_2013, complete genome", *NCBI*, 13 pages, Jul. 24, 2014.
GenBank Accession No. KF186566.1, "Middle East respiratory syndrome coronavirus isolate Al-Hasa_2_2013, complete genome", *NCBI*, 13 pages, Jul. 24, 2014.
GenBank Accession No. KF186564.1, "Middle East respiratory syndrome coronavirus isolate Al-Hasa_4_2013, complete genome", *NCBI*, 13 pages, Jul. 24, 2014.
GenBank Accession No. KF192507.1, "Middle East respiratory syndrome coronavirus, complete genome", *NCBI*, 13 pages, Jul. 24, 2014.
GenBank Accession No. NC_019843, "Middle East respiratory syndrome coronavirus, complete genome", *NCBI*, 16 pages, Sep. 9, 2014.
GenBank Accession No. KC667074, "Human betacoronavirus 2c England-Qatar/2012, complete genome", *NCBI*, 13 pages, Apr. 30, 2013.
GenBank Accession No. KF600656.1, "Middle East respiratory syndrome coronavirus isolate Al-Hasa_13d_2013, partial genome", *NCBI*, 2 pages, Jul. 24, 2014.
GenBank Accession No. KF600655.1, "Middle East respiratory syndrome coronavirus isolate Al-Hasa_7a_2013, partial genome", *NCBI*, 8 pages, Jul. 24, 2014.
GenBank Accession No. KF600654.1, "Middle East respiratory syndrome coronavirus isolate Al-Hasa_9b_2013, partial genome", *NCBI*, 2 pages, Jul. 24, 2014.
GenBank Accession No. KF600649.1, "Middle East respiratory syndrome coronavirus isolate Al-Hasa_9c_2013, partial genome", *NCBI*, 2 pages, Jul. 24, 2014.
GenBank Accession No. KF600648.1, "Middle East respiratory syndrome coronavirus isolate Al-Hasa_9a_2013, partial genome", *NCBI*, 3 pages, Jul. 24, 2014.
GenBank Accession No. KF600646.1, "Middle East respiratory syndrome coronavirus isolate Al-Hasa_11b_2013, partial genome", *NCBI*, 4 pages, Jul. 24, 2014.
GenBank Accession No. KF600643.1, "Middle East respiratory syndrome coronavirus isolate Al-Hasa_14b_2013, partial genome", *NCBI*, 7 pages, Jul. 24, 2014.
GenBank Accession No. KF600642.1, "Middle East respiratory syndrome coronavirus isolate Al-Hasa_10b_2013, partial genome", *NCBI*, 3 pages, Jul. 24, 2014.
GenBank Accession No. KF600640.1, "Middle East respiratory syndrome coronavirus isolate Al-Hasa_13e_2013, partial genome", *NCBI*, 2 pages, Jul. 24, 2014.
GenBank Accession No. KF600639.1, "Middle East respiratory syndrome coronavirus isolate Al-Hasa_9e_2013, partial genome", *NCBI*, 2 pages, Jul. 24, 2014.
GenBank Accession No. KF600638.1, "Middle East respiratory syndrome coronavirus isolate Al-Hasa_8b_2013, partial genome", *NCBI*, 3 pages, Jul. 24, 2014.
GenBank Accession No. KF600637.1, "Middle East respiratory syndrome coronavirus isolate Al-Hasa_13c_2013, partial genome", *NCBI*, 2 pages, Jul. 24, 2014.
GenBank Accession No. KF600636.1, "Middle East respiratory syndrome coronavirus isolate Al-Hasa_11c_2013, partial genome", *NCBI*, 7 pages, Jul. 24, 2014.
GenBank Accession No, KF600635.1, "Middle East respiratory syndrome coronavirus isolate Al-Hasa_8d_2013, partial genome", *NCBI*, 2 pages, Jul. 24, 2014.
GenBank Accession No. KF600631.1, "Middle East respiratory syndrome coronavirus isolate Al-Hasa_22e_2013, partial genome", *NCBI*, 3 pages, Jul. 24, 2014.
GenBank Accession No. KF600626.1, "Middle East respiratory syndrome coronavirus isolate Al-Hasa_8c_2013, partial genome", *NCBI*, 5 pages, Jul. 24, 2014.
GenBank Accession No. KF600625.1, "Middle East respiratory syndrome coronavirus isolate Al-Hasa_22b_2013, partial genome", *NCBI*, 2 pages, Jul. 24, 2014.
GenBank Accession No. KF600624.1, "Middle East respiratory syndrome coronavirus isolate Al-Hasa_10c_2013, partial genome", *NCBI*, 2 pages, Jul. 24, 2014.

(56) References Cited

OTHER PUBLICATIONS

GenBank Accession No. KF600623.1, "Middle East respiratory syndrome coronavirus isolate Al-Hasa_7b_2013, partial genome", *NCBI*, 5 pages, Jul. 24, 2014.
GenBank Accession No. KF600622.1, "Middle East respiratory syndrome coronavirus isolate Al-Hasa_9d_2013, partial genome", *NCBI*, 3 pages, Jul. 24, 2014.
GenBank Accession No. KF600621.1, "Middle East respiratory syndrome coronavirus isolate Al-Hasa_22f_2013, partial genome", *NCBI*, 2 pages, Jul. 24, 2014.
GenBank Accession No. KF600619.1, "Middle East respiratory syndrome coronavirus isolate Al-Hasa_22d_2013, partial genome", *NCBI*, 3 pages, Jul. 24, 2014.
GenBank Accession No. KF600618.1, "Middle East respiratory syndrome coronavirus isolate Al-Hasa_8a_2013, partial genome", *NCBI*, 2 pages, Jul. 24, 2014.
GenBank Accession No. KF600616.1, "Middle East respiratory syndrome coronavirus isolate Al-Hasa_13b_2013, partial genome", *NCBI*, 3 pages, Jul. 24, 2014.
GenBank Accession No. KF600615.1, "Middle East respiratory syndrome coronavirus isolate Al-Hasa_14a_2013, partial genome", *NCBI*, 4 pages, Jul. 24, 2014.
GenBank Accession No. KF600614.1, "Middle East respiratory syndrome coronavirus isolate Al-Hasa_10e_2013, partial genome", *NCBI*, 2 pages, Jul. 24, 2014.
GenBank Accession No. KF600641.1, "Middle East respiratory syndrome coronavirus isolate Al-Hasa_10d_2013, partial genome", *NCBI*, 1 page, Jul. 24, 2014.
GenBank Accession No. KF600633.1, "Middle East respiratory syndrome coronavirus isolate Al-Hasa_22c_2013, partial genome", *NCBI*, 2 pages, Jul. 24, 2014.
GenBank Accession No. KF600629.1, "Middle East respiratory syndrome coronavirus isolate Al-Hasa_11a_2013, partial genome", *NCBI*, 2 pages, Jul. 24, 2014.
GenBank Accession No. KF600617.1, "Middle East respiratory syndrome coronavirus isolate Al-Hasa_22a_2013, partial genome", *NCBI*, 2 pages, Jul. 24, 2014.
GenBank Accession No. KC869678.2, "Coronavirus Neoromicia/PML-PHE1/RSA/2011 RNA-dependent RNA polymerase (ORF1b) gene, partial cds", *NCBI*, 2 pages, Aug. 27, 2013.
GenBank Accession No. KF493885.1, "Bat Coronavirus Taper/CII_KDS_287/Bisha/Saudi Arabia/2012 RNA-directed RNA polymerase gene, partial cds", *NCBI*, 1 page, Nov. 14, 2013.
GenBank Accession No. KF493888.1, "Bat coronavirus Rhhar/CII_KSA_003/Bisha/Saudi Arabia/2013 RNA-directed RNA polymerase gene, partial cds", *NCBI*, 1 page, Nov. 14, 2013.
GenBank Accession No. KF493887.1, "Bat coronavirus Pikuh/CII_KSA_001/Riyadh/Saudi Arabia/2013 RNA-directed RNA polymerase gene, partial cds", *NCBI*, 1 page, Nov. 14, 2013.
GenBank Accession No. KF493886.1, "Bat coronavirus Rhhar/CII_KSA_002/Bisha/Saudi Arabia/2013 RNA-directed RNA polymerase gene, partial cds", *NCBI*, 1 page, Nov. 14, 2013.
GenBank Accession No. KF493884.1, "Bat coronavirus Rhhar/CII_KSA_004/Bisha/Saudi Arabia/2013 RNA-directed RNA polymerase gene, partial cds", *NCBI*, 1 page, Nov. 14, 2013.
GenBank Accession No. EF065506, "Bat coronavirus HKU4-2, complete genome", *NCBI*, 12 pages, Feb. 7, 2007.
GenBank Accession No. NC_009019, "Bat coronavirus HKU4-1, complete genome", *NCBI*, 13 pages, Mar. 28, 2016.
GenBank Accession No. EF065507, "Bat coronavirus HKU4-3, complete genome", *NCBI*, 12 pages, Feb. 7, 2007.
GenBank Accession No. EF065508, "Bat coronavirus HKU4-4, complete genome", *NCBI*, 12 pages, Feb. 7, 2007.
GenBank Accession No. NC_008315, "Bat coronavirus (BtCoV/133/2005), complete genome", *NCBI*, 12 pages, May 22, 2007.
GenBank Accession No. EF065512, "Bat coronavirus HKU5-5, complete genome", *NCBI*, 12 pages, Feb. 7, 2007.
GenBank Accession No. NC_009020, "Bat coronavirus HKU5-1, complete genome", *NCBI*, 13 pages, Mar. 28, 2016.
GenBank Accession No. EF065510, "Bat coronavirus HKU5-2, complete genome", *NCBI*, 12 pages, Feb. 7, 2007.
GenBank Accession No. EF065511, "Bat coronavirus HKU5-3, complete genome", *NCBI*, 12 pages, Feb. 7, 2007.
GenBank Accession No. KC776174.1, "Human betacoronavirus 2c Jordan-N3/2012, complete genome", *NCBI*, 13 pages, Mar. 25, 2013.
GenBank Accession No. JX869059.2, "Human betacoronavirus 2c EMC/2012, complete genome", *NCBI*, 13 pages, Dec. 4, 2012.
GenBank Accession No. KC522089.1, "Pipistrellus bat coronavirus HKU5 isolate 33R RNA-dependent RNA polymerase gene, partial cds", *NCBI*, 2 pages, Jul. 15, 2013.
GenBank Accession No. KC522088.1, "Pipistrellus bat coronavirus HKU5 isolate 32R RNA-dependent RNA polymerase gene, partial cds", *NCBI*, 2 pages, Jul. 15, 2013.
GenBank Accession No. KC522087.1, "Pipistrellus bat coronavirus HKU5 isolate 31R RNA-dependent RNA polymerase gene, partial cds", *NCBI*, 2 pages, Jul. 15, 2013.
GenBank Accession No. KC522086.1, "Pipistrellus bat coronavirus HKU5 isolate 30R RNA-dependent RNA polymerase gene, partial cds", *NCBI*, 2 pages, Jul. 15, 2013.
GenBank Accession No. KC522085.1, "Pipistrellus bat coronavirus HKU5 isolate 28R RNA-dependent RNA polymerase gene, partial cds", *NCBI*, 2 pages, Jul. 15, 2013.
GenBank Accession No. KC522084.1, "Pipistrellus bat coronavirus HKU5 isolate 27R RNA-dependent RNA polymerase gene, partial cds", *NCBI*, 2 pages, Jul. 15, 2013.
GenBank Accession No. KC522083.1, "Pipistrellus bat coronavirus HKU5 isolate 26R RNA-dependent RNA polymerase gene, partial cds", *NCBI*, 2 pages, Jul. 15, 2013.
GenBank Accession No. KC522082.1, "Pipistrellus bat coronavirus HKU5 isolate 24R RNA-dependent RNA polymerase gene, partial cds", *NCBI*, 2 pages, Jul. 15, 2013.
GenBank Accession No. KC522081.1, "Pipistrellus bat coronavirus HKU5 isolate 22R RNA-dependent RNA polymerase gene, partial cds", *NCBI*, 2 pages, Jul. 15, 2013.
GenBank Accession No. KC522080.1, "Pipistrellus bat coronavirus HKU5 isolate 21R RNA-dependent RNA polymerase gene, partial cds", *NCBI*, 2 pages, Jul. 15, 2013.
GenBank Accession No. KC522079.1, "Pipistrellus bat coronavirus HKU5 isolate 20R RNA-dependent RNA polymerase gene, partial cds", *NCBI*, 2 pages, Jul. 15, 2013.
GenBank Accession No. KC522078.1, "Pipistrellus bat coronavirus HKU5 isolate 19R RNA-dependent RNA polymerase gene, partial cds", *NCBI*, 2 pages, Jul. 15, 2013.
GenBank Accession No. KC522077.1, "Pipistrellus bat coronavirus HKU5 isolate 18R RNA-dependent RNA polymerase gene, partial cds", *NCBI*, 2 pages, Jul. 15, 2013.
GenBank Accession No. KC522076.1, "Pipistrellus bat coronavirus HKU5 isolate 17R RNA-dependent RNA polymerase gene, partial cds", *NCBI*, 2 pages, Jul. 15, 2013.
GenBank Accession No. KC522075.1, "Pipistrellus bat coronavirus HKU5 isolate 16R RNA-dependent RNA polymerase gene, partial cds", *NCBI*, 2 pages, Jul. 15, 2013.
GenBank Accession No. KC522104.1, "Pipistrellus bat coronavirus HKU5 isolate 33S spike glycoprotein gene, complete cds", *NCBI*, 3 pages, Jul. 15, 2013.
GenBank Accession No. KC522103.1, "Pipistrellus bat coronavirus HKU5 isolate 32S spike glycoprotein gene, complete cds", *NCBI*, 3 pages, Jul. 15, 2013.
GenBank Accession No. KC522102.1, "Pipistrellus bat coronavirus HKU5 isolate 31S spike glycoprotein gene, complete cds", *NCBI*, 3 pages, Jul. 15, 2013.
GenBank Accession No. KC522101.1, "Pipistrellus bat coronavirus HKU5 isolate 30S spike glycoprotein gene, complete cds", *NCBI*, 3 pages, Jul. 15, 2013.
GenBank Accession No. KC522100.1, "Pipistrellus bat coronavirus HKU5 isolate 28S spike glycoprotein gene, complete cds", *NCBI*, 3 pages, Jul. 15, 2013.
GenBank Accession No. KC522099.1, "Pipistrellus bat coronavirus HKU5 isolate 27S spike glycoprotein gene, complete cds", *NCBI*, 3 pages, Jul. 15, 2013.

(56) References Cited

OTHER PUBLICATIONS

GenBank Accession No. KC522098.1, "Pipistrellus bat coronavirus HKU5 isolate 26S spike glycoprotein gene, complete cds", *NCBI*, 3 pages, Jul. 15, 2013.
GenBank Accession No. KC522097.1, "Pipistrellus bat coronavirus HKU5 isolate 24S spike glycoprotein gene, complete cds", *NCBI*, 3 pages, Jul. 15, 2013.
GenBank Accession No. KC522096.1, "Pipistrellus bat coronavirus HKU5 isolate 22S spike glycoprotein gene, complete cds", *NCBI*, 3 pages, Jul. 15, 2013.
GenBank Accession No. KC522095.1, "Pipistrellus bat coronavirus HKU5 isolate 21S spike glycoprotein gene, complete cds", *NCBI*, 3 pages, Jul. 15, 2013.
GenBank Accession No. KC522094.1, "Pipistrellus bat coronavirus HKU5 isolate 20S spike glycoprotein gene, complete cds", *NCBI*, 3 pages, Jul. 15, 2013.
GenBank Accession No. KC522093.1, "Pipistrellus bat coronavirus HKU5 isolate 19S spike glycoprotein gene, complete cds", *NCBI*, 3 pages, Jul. 15, 2013.
GenBank Accession No. KC522092.1, "Pipistrellus bat coronavirus HKU5 isolate 18S spike glycoprotein gene, complete cds", *NCBI*, 3 pages, Jul. 15, 2013.
GenBank Accession No. KC522091.1, "Pipistrellus bat coronavirus HKU5 isolate 17S spike glycoprotein gene, complete cds", *NCBI*, 3 pages, Jul. 15, 2013.
GenBank Accession No. KC522090.1, "Pipistrellus bat coronavirus HKU5 isolate 16S spike glycoprotein gene, complete cds", *NCBI*, 3 pages, Jul. 15, 2013.
GenBank Accession No. KC522119.1, "Pipistrellus bat coronavirus HKU5 isolate 33N nucleocapsid protein gene, complete cds", *NCBI*, 2 pages, Jul. 15, 2013.
GenBank Accession No. KC522118.1, "Pipistrellus bat coronavirus HKU5 isolate 32N nucleocapsid protein gene, complete cds", *NCBI*, 2 pages, Jul. 15, 2013.
GenBank Accession No. KC522117.1, "Pipistrellus bat coronavirus HKU5 isolate 31N nucleocapsid protein gene, complete cds", *NCBI*, 2 pages, Jul. 15, 2013.
GenBank Accession No. KC522116.1, "Pipistrellus bat coronavirus HKU5 isolate 30N nucleocapsid protein gene, complete cds", *NCBI*, 2 pages, Jul. 15, 2013.
GenBank Accession No. KC522115.1, "Pipistrellus bat coronavirus HKU5 isolate 28N nucleocapsid protein gene, complete cds", *NCBI*, 2 pages, Jul. 15, 2013.
GenBank Accession No. KC522114.1, "Pipistrellus bat coronavirus HKU5 isolate 27N nucleocapsid protein gene, complete cds", *NCBI*, 2 pages, Jul. 15, 2013.
GenBank Accession No. KC522113.1, "Pipistrellus bat coronavirus HKU5 isolate 26N nucleocapsid protein gene, complete cds", *NCBI*, 2 pages, Jul. 15, 2013.
GenBank Accession No. KC522112.1, "Pipistrellus bat coronavirus HKU5 isolate 24N nucleocapsid protein gene, complete cds", *NCBI*, 2 pages, Jul. 15, 2013.
GenBank Accession No. KC522111.1, "Pipistrellus bat coronavirus HKU5 isolate 22N nucleocapsid protein gene, complete cds", *NCBI*, 2 pages, Jul. 15, 2013.
GenBank Accession No. KC522110.1, "Pipistrellus bat coronavirus HKU5 isolate 21N nucleocapsid protein gene, complete cds", *NCBI*, 2 pages, Jul. 15, 2013.
GenBank Accession No. KC522109.1, "Pipistrellus bat coronavirus HKU5 isolate 20N nucleocapsid protein gene, complete cds", *NCBI*, 2 pages, Jul. 15, 2013.
GenBank Accession No. KC522108.1, "Pipistrellus bat coronavirus HKU5 isolate 19N nucleocapsid protein gene, complete cds", *NCBI*, 2 pages, Jul. 15, 2013.
GenBank Accession No. KC522107.1, "Pipistrellus bat coronavirus HKU5 isolate 18N nucleocapsid protein gene, complete cds", *NCBI*, 2 pages, Jul. 15, 2013.
GenBank Accession No. KC522106.1, "Pipistrellus bat coronavirus HKU5 isolate 17N nucleocapsid protein gene, complete cds", *NCBI*, 2 pages, Jul. 15, 2013.
GenBank Accession No. KC522105.1, "Pipistrellus bat coronavirus HKU5 isolate 16N nucleocapsid protein gene, complete cds", *NCBI*, 3 pages, Jul. 15, 2013.
GenBank Accession No. KC522048.1, "Tylonycteris bat coronavirus HKU4 isolate 15R RNA-dependent RNA polymerase gene, partial cds", *NCBI*, 2 pages, Jul. 15, 2013.
GenBank Accession No. KC522047.1, "Tylonycteris bat coronavirus HKU4 isolate 14R RNA-dependent RNA polymerase gene, partial cds", *NCBI*, 2 pages, Jul. 15, 2013.
GenBank Accession No. KC522046.1, "Tylonycteris bat coronavirus HKU4 isolate 12R RNA-dependent RNA polymerase gene, partial cds", *NCBI*, 2 pages, Jul. 15, 2013.
GenBank Accession No. KC522045.1, "Tylonycteris bat coronavirus HKU4 isolate 11R RNA-dependent RNA polymerase gene, partial cds", *NCBI*, 2 pages, Jul. 15, 2013.
GenBank Accession No. KC522044.1, "Tylonycteris bat coronavirus HKU4 isolate 10R RNA-dependent RNA polymerase gene, partial cds", *NCBI*, 2 pages, Jul. 15, 2013.
GenBank Accession No. KC522043.1, "Tylonycteris bat coronavirus HKU4 isolate 9R RNA-dependent RNA polymerase gene, partial cds", *NCBI*, 2 pages, Jul. 15, 2013.
GenBank Accession No. KC522042.1, "Tylonycteris bat coronavirus HKU4 isolate 8R RNA-dependent RNA polymerase gene, partial cds", *NCBI*, 2 pages, Jul. 15, 2013.
GenBank Accession No. KC522041.1, "Tylonycteris bat coronavirus HKU4 isolate 7R RNA-dependent RNA polymerase gene, partial cds", *NCBI*, 2 pages, Jul. 15, 2013.
GenBank Accession No. KC522040.1, "Tylonycteris bat coronavirus HKU4 isolate 6R RNA-dependent RNA polymerase gene, partial cds", *NCBI*, 2 pages, Jul. 15, 2013.
GenBank Accession No. KC522039.1, "Tylonycteris bat coronavirus HKU4 isolate 5R RNA-dependent RNA polymerase gene, partial cds", *NCBI*, 2 pages, Jul. 15, 2013.
GenBank Accession No. KC522038.1, "Tylonycteris bat coronavirus HKU4 isolate 4R RNA-dependent RNA polymerase gene, partial cds", *NCBI*, 2 pages, Jul. 15, 2013.
GenBank Accession No. KC522037.1, "Tylonycteris bat coronavirus HKU4 isolate 3R RNA-dependent RNA polymerase gene, partial cds", *NCBI2* pages, Jul. 15, 2013.
GenBank Accession No. KC522036.1, "Tylonycteris bat coronavirus HKU4 isolate 2R RNA-dependent RNA polymerase gene, partial cds", *NCBI*, 2 pages, Jul. 15, 2013.
GenBank Accession No. KC522061.1, "Tylonycteris bat coronavirus HKU4 isolate 15S spike glycoprotein gene, complete cds", *NCBI*, 3 pages, Jul. 15, 2013.
GenBank Accession No. KC522060.1, "Tylonycteris bat coronavirus HKU4 isolate 14S spike glycoprotein gene, complete cds", *NCBI*, 3 pages, Jul. 15, 2013.
GenBank Accession No. KC522059.1, "Tylonycteris bat coronavirus HKU4 isolate 12S spike glycoprotein gene, complete cds", *NCBI*, 3 pages, Jul. 15, 2013.
GenBank Accession No. KC522058.1, "Tylonycteris bat coronavirus HKU4 isolate 11S spike glycoprotein gene, complete cds", *NCBI*, 3 pages, Jul. 15, 2013.
GenBank Accession No. KC522057.1, "Tylonycteris bat coronavirus HKU4 isolate 10S spike glycoprotein gene, complete cds", *NCBI*, 3 pages, Jul. 15, 2013.
GenBank Accession No. KC522056.1, "Tylonycteris bat coronavirus HKU4 isolate 9S spike glycoprotein gene, complete cds", *NCBI*, 3 pages, Jul. 15, 2013.
GenBank Accession No. KC522055.1, "Tylonycteris bat coronavirus HKU4 isolate 8S spike glycoprotein gene, complete cds", *NCBI*, 3 pages, Jul. 15, 2013.
GenBank Accession No. KC522054.1, "Tylonycteris bat coronavirus HKU4 isolate 7S spike glycoprotein gene, complete cds", *NCBI*, 3 pages, Jul. 15, 2013.
GenBank Accession No. KC522053.1, "Tylonycteris bat coronavirus HKU4 isolate 6S spike glycoprotein gene, complete cds", *NCBI*, 3 pages, Jul. 15, 2013.
GenBank Accession No. KC522052.1, "Tylonycteris bat coronavirus HKU4 isolate 5S spike glycoprotein gene, complete cds", *NCBI*, 3 pages, Jul. 15, 2013.

(56) References Cited

OTHER PUBLICATIONS

GenBank Accession No. KC522051.1, "Tylonycteris bat coronavirus HKU4 isolate 4S spike glycoprotein gene, complete cds", *NCBI*, 3 pages, Jul. 15, 2013.
GenBank Accession No. KC522050.1, "Tylonycteris bat coronavirus HKU4 isolate 3S spike glycoprotein gene, complete cds", *NCBI*, 3 pages, Jul. 15, 2013.
GenBank Accession No. KC522049.1, "Tylonycteris bat coronavirus HKU4 isolate 2S spike glycoprotein gene, complete cds", *NCBI*, 3 pages, Jul. 15, 2013.
GenBank Accession No. KC522074.1, "Tylonycteris bat coronavirus HKU4 isolate 15N nucleocapsid protein gene, complete cds", *NCBI*, 2 pages, Jul. 15, 2013.
GenBank Accession No. KC522073.1, "Tylonycteris bat coronavirus HKU4 isolate 14N nucleocapsid protein gene, complete cds", *NCBI*, 2 pages, Jul. 15, 2013.
GenBank Accession No. KC522072.1, "Tylonycteris bat coronavirus HKU4 isolate 12N nucleocapsid protein gene, complete cds", *NCBI*, 2 pages, Jul. 15, 2013.
GenBank Accession No. KC522071.1, "Tylonycteris bat coronavirus HKU4 isolate 11N nucleocapsid protein gene, complete cds", *NCBI*, 2 pages, Jul. 15, 2013.
GenBank Accession No. KC522070.1, "Tylonycteris bat coronavirus HKU4 isolate 10N nucleocapsid protein gene, complete cds", *NCBI*, 2 pages, Jul. 15, 2013.
GenBank Accession No. KC522069.1, "Tylonycteris bat coronavirus HKU4 isolate 9N nucleocapsid protein gene, complete cds", *NCBI*, 2 pages, Jul. 15, 2013.
GenBank Accession No. KC522068.1, "Tylonycteris bat coronavirus HKU4 isolate 8N nucleocapsid protein gene, complete cds", *NCBI*, 2 pages, Jul. 15, 2013.
GenBank Accession No. KC522067.1, "Tylonycteris bat coronavirus HKU4 isolate 7N nucleocapsid protein gene, complete cds", *NCBI*, 2 pages, Jul. 15, 2013.
GenBank Accession No. KC522066.1, "Tylonycteris bat coronavirus HKU4 isolate 6N nucleocapsid protein gene, complete cds", *NCBI*, 2 pages, Jul. 15, 2013.
GenBank Accession No. KC522065.1, "Tylonycteris bat coronavirus HKU4 isolate 5N nucleocapsid protein gene, complete cds", *NCBI*, 2 pages, Jul. 15, 2013.
GenBank Accession No. KC522064.1, "Tylonycteris bat coronavirus HKU4 isolate 4N nucleocapsid protein gene, complete cds", *NCBI*, 2 pages, Jul. 15 2013.
GenBank Accession No. KC522063.1, "Tylonycteris bat coronavirus HKU4 isolate 3N nucleocapsid protein gene, complete cds", *NCBI*, 2 pages, Jul. 15, 2013.
GenBank Accession No. KC522062.1, "Tylonycteris bat coronavirus HKU4 isolate 2N nucleocapsid protein gene, complete cds", *NCBI*, 2 pages, Jul. 15, 2013.
GenBank Accession No. NC_007025, "Feline coronavirus, complete genome", *NCBI*, 13 pages, Dec. 1, 2009.
GenBank Accession No. NC_002306, "Feline infectious peritonitis virus, complete genome", *NCBI*, 12 pages, Dec. 13, 2013.
GenBank Accession No. DQ811789.2, "TGEV virulent Purdue, complete genome", *NCBI*, 12 pages, Apr. 29, 2011.
GenBank Accession No. DQ811786.2, "TGEV Miller M60, complete genome", *NCBI*, 12 pages, Apr. 29, 2011.
GenBank Accession No. DQ811788.1, "TGEV Purdue P115, complete genome", *NCBI*, 11 pages, Jul. 14, 2016.
GenBank Accession No. DQ811785.1, "TGEV Miller M6, complete genome", *NCBI*, 11 pages, Jul. 14, 2016.
GenBank Accession No. X52157.1, "Coronavirus TGEV mRNA for nucleoprotein, 5' region", *NCBI*, 1 pages, Jul. 26, 2016.
GenBank Accession No. AJ011482.1, "Porcine transmissible gastroenteritis virus minigenome", *NCBI*, 5 pages, Nov. 14, 2006.
GenBank Accession No. KC962433.1, "Transmissible gastroenteritis virus isolate TGEV-HX, complete genome", *NCBI*, 11 pages, Apr. 1, 2015.
GenBank Accession No. AJ271965.2, "Transmissible gastroenteritis virus complete genome, genomic RNA", *NCBI*, 13 pages, Apr. 15, 2005.
GenBank Accession No. JQ693060.1, "Transmissible gastroenteritis virus isolate KT3 nucleocapsid protein (N) gene, complete cds", *NCBI*, 2 pages, Mar. 22, 2013.
GenBank Accession No. KC609371.1, "Transmissible gastroenteritis virus isolate ZH spike protein mRNA, complete cds", *NCBI*, 3 pages, May 21, 2013.
GenBank Accession No. JQ693059.1, "Transmissible gastroenteritis virus isolate KT2 nucleocapsid protein (N) gene, complete cds", *NCBI*, 2 pages, Mar. 22, 2013.
GenBank Accession No. JQ693058.1, "Transmissible gastroenteritis virus isolate DAE nucleocapsid protein (N) gene, complete cds", *NCBI*, 2 pages, Mar. 22, 2013.
GenBank Accession No. JQ693057.1, "Transmissible gastroenteritis virus isolate 133 nucleocapsid protein (N) gene, complete cds", *NCBI*, 2 pages, Mar. 22, 2013.
GenBank Accession No. JQ693052.1, "Transmissible gastroenteritis virus isolate KT3 spike glycoprotein (S) gene, complete cds", *NCBI*, 3 pages, Mar. 22, 2013.
GenBank Accession No. JQ693051.1, "Transmissible gastroenteritis virus isolate KT2 spike glycoprotein (S) gene, complete cds", *NCBI*, 3 pages, Mar. 22, 2013.
GenBank Accession No. JQ693050.1, "Transmissible gastroenteritis virus isolate DAE spike glycoprotein (S) gene, complete cds", *NCBI*, 3 pages, Mar. 22, 2013.
GenBank Accession No. NC_001961.1, "Porcine respiratory and reproductive syndrome virus, complete genome", *NCBI*, 11 pages, Nov. 2, 2012.
GenBank Accession No. DQ811787, "PRCV ISU-1, complete genome", *NCBI*, 11 pages, Jul. 14, 2016.
GenBank Accession No. NC_010437, "Bat coronavirus 1A, complete genome", *NCBI*, 12 pages, Mar. 28, 2016.
GenBank Accession No. NC_010436, "Bat coronavirus 1B, complete genome", *NCBI*, 13 pages, Apr. 23, 2008.
GenBank Accession No. NC_010438, "Bat coronavirus HKU8, complete genome", *NCBI*, 13 pages, Mar. 28, 2016.
GenBank Accession No. DQ648858, "Bat coronavirus (BtCoV/512/2005) ORF1, spike protein, putative ORF3, envelope protein, matrix protein, and nucleocapsid protein genes, complete cds", *NCBI*, 11 pages, Jul. 19, 2006.
GenBank Accession No. NC_003436, "Porcine epidemic diarrhea virus, complete genome", *NCBI*, 12 pages, Feb. 10, 2015.
GenBank Accession No. DQ355224.1, "Porcine epidemic diarrhea virus strain CH/S nucleocapsid protein (N) gene, complete cds", *NCBI*, 2 pages, Feb. 1, 2006.
GenBank Accession No. DQ355223.1, "Porcine epidemic diarrhea virus strain S nucleocapsid protein (N) gene, complete cds", *NCBI*, 2 pages, Feb. 1, 2006.
GenBank Accession No. DQ355221.1, "Porcine epidemic diarrhea virus strain CV777 nucleocapsid protein (N) gene, complete cds", *NCBI*, 2 pages, Feb. 1, 2006.
GenBank Accession No. JN601062.1, "Porcine epidemic diarrhea virus strain CH/GXNN/2011 N protein (N) gene, complete cds", *NCBI*, 2 pages, Jun. 3, 2013.
GenBank Accession No. JN601061.1, "Porcine epidemic diarrhea virus strain CH/SDRZ-2/2011 N protein (N) gene, complete cds", *NCBI*, 2 pages, Jun. 3, 2013.
GenBank Accession No. JN601060.1, "Porcine epidemic diarrhea virus strain CH/SDRZ-1/2011 N protein (N) gene, complete cds", *NCBI*, 2 pages, Jun. 3, 2013.
GenBank Accession No. JN601059.1, "Porcine epidemic diarrhea virus strain CH/HLJHG/2011 N protein (N) gene, complete cds", *NCBI*, 2 pages, Jun. 3, 2013.
GenBank Accession No. JN601058.1, "Porcine epidemic diarrhea virus strain CH/GDQY-3/2011 N protein (N) gene, complete cds", *NCBI*, 2 pages, Jun. 3, 2013.
GenBank Accession No. JN601057.1, "Porcine epidemic diarrhea virus strain CH/GDQY-1/2011 N protein (N) gene, complete cds", *NCBI*, 2 pages, Jun. 3, 2013.

(56) References Cited

OTHER PUBLICATIONS

GenBank Accession No. JN601056.1, "Porcine epidemic diarrhea virus strain CH/GDQY-1/2011 N protein (N) gene, complete cds", *NCBI*, 2 pages, Jun. 3, 2013.
GenBank Accession No. JN601055.1, "Porcine epidemic diarrhea virus strain CH/FJND/2011 N protein (N) gene, complete cds", *NCBI*, 2 pages, Jun. 3, 2013.
GenBank Accession No. JN601054.1, "Porcine epidemic diarrhea virus strain CH/BJYQ-2/2011 N protein (N) gene, complete cds", *NCBI*, 2 pages, Jun. 3, 2013.
GenBank Accession No. JN601053.1, "Porcine epidemic diarrhea virus strain CH/BJYQ-1/2011 N protein (N) gene, complete cds", *NCBI*, 2 pages, Jun. 3, 2013.
GenBank Accession No. JN601052.1, "Porcine epidemic diarrhea virus strain CH/HNZZ/2011 N protein (N) gene, complete cds", *NCBI*, 2 pages, Jun. 3, 2013.
GenBank Accession No. JN400902.1, "Porcine epidemic diarrhea virus strain CH/HBQX/10 membrane glycoprotein (M) gene, complete cds", *NCBI*, 3 pages, Apr. 3, 2013.
GenBank Accession No. JN547395.1, "Porcine epidemic diarrhea virus strain CH/HBQX/10 non-structural protein gene, complete cds", *NCBI*, 2 pages, Apr. 3, 2013.
GenBank Accession No. FJ687473.1, "Porcine epidemic diarrhea virus isolate CPF1074 membrane protein (M) gene, complete cds", *NCBI*, 2 pages, Apr. 6, 2011.
GenBank Accession No. FJ687472.1, "Porcine epidemic diarrhea virus isolate PFF1051 membrane protein (M) gene, complete cds", *NCBI*, 2 pages, Apr. 6, 2011.
GenBank Accession No. FJ687471.1, "Porcine epidemic diarrhea virus isolate CPF531 membrane protein (M) gene, complete cds", *NCBI*, 2 pages, Apr. 6, 2011.
GenBank Accession No. FJ687470.1, "Porcine epidemic diarrhea virus isolate PFF514 membrane protein (M) gene, complete cds", *NCBI*, 2 pages, Apr. 6, 2011.
GenBank Accession No. FJ687469.1, "Porcine epidemic diarrhea virus isolate PFF513 membrane protein (M) gene, complete cds", *NCBI*, 2 pages, Apr. 6, 2011.
GenBank Accession No. FJ687468.1, "Porcine epidemic diarrhea virus isolate PFF381 membrane protein (M) gene, complete cds", *NCBI*, 2 pages, Apr. 6, 2011.
GenBank Accession No. FJ687467.1, "Porcine epidemic diarrhea virus isolate CPF299 membrane protein (M) gene, complete cds", *NCBI*, 2 pages, Apr. 6, 2011.
GenBank Accession No. FJ687466.1, "Porcine epidemic diarrhea virus isolate PFF285 membrane protein (M) gene, complete cds", *NCBI*, 2 pages, Apr. 6, 2011.
GenBank Accession No. FJ687465.1, "Porcine epidemic diarrhea virus isolate CPF259 membrane protein (M) gene, complete cds", *NCBI*, 2 pages, Apr. 6, 2011.
GenBank Accession No. FJ687464.1, "Porcine epidemic diarrhea virus isolate BIF256 membrane protein (M) gene, complete cds", *NCBI*, 2 pages, Apr. 6, 2011.
GenBank Accession No. FJ687463.1, "Porcine epidemic diarrhea virus isolate CPF193 membrane protein (M) gene, complete cds", *NCBI*, 2 pages, Apr. 6, 2011.
GenBank Accession No. FJ687462.1, "Porcine epidemic diarrhea virus isolate PFF188 membrane protein (M) gene, complete cds", *NCBI*, 2 pages, Apr. 6, 2011.
GenBank Accession No. FJ687461.1, "Porcine epidemic diarrhea virus isolate VF131 membrane protein (M) gene, complete cds", *NCBI*, 2 pages, Apr. 6, 2011.
GenBank Accession No. FJ687460.1, "Porcine epidemic diarrhea virus isolate BIF118 membrane protein (M) gene, complete cds", *NCBI*, 2 pages, Apr. 6, 2011.
GenBank Accession No. FJ687459.1, "Porcine epidemic diarrhea virus isolate MF78 membrane protein (M) gene, complete cds", *NCBI*, 2 pages, Apr. 6, 2011.
GenBank Accession No. FJ687458.1, "Porcine epidemic diarrhea virus isolate V25010 membrane protein (M) gene, complete cds", *NCBI*, 2 pages, Apr. 6, 2011.
GenBank Accession No. FJ687457.1, "Porcine epidemic diarrhea virus isolate M2366 membrane protein (M) gene, complete cds", *NCBI*, 2 pages, Apr. 6, 2011.
GenBank Accession No. FJ687456.1, "Porcine epidemic diarrhea virus isolate M2227 membrane protein (M) gene, complete cds", *NCBI*, 2 pages, Apr. 6, 2011.
GenBank Accession No. FJ687455.1, "Porcine epidemic diarrhea virus isolate M1763 membrane protein (M) gene, complete cds", *NCBI*, 2 pages, Apr. 6, 2011.
GenBank Accession No. FJ687454.1, "Porcine epidemic diarrhea virus isolate e1697 membrane protein (M) gene, complete cds", *NCBI*, 2 pages, Apr. 6, 2011.
GenBank Accession No. FJ687453, "Porcine epidemic diarrhea virus isolate e1642 membrane protein (M) gene, complete cds", *NCBI*, 2 pages, Apr. 6, 2011.
GenBank Accession No. FJ687452.1, "Porcine epidemic diarrhea virus isolate M1595 membrane protein (M) gene, complete cds", *NCBI*, 2 pages, Apr. 6, 2011.
GenBank Accession No. FJ687451.1, "Porcine epidemic diarrhea virus isolate BI1108 membrane protein (M) gene, complete cds", *NCBI*, 2 pages, Apr. 6, 2011.
GenBank Accession No. FJ687450.1, "Porcine epidemic diarrhea virus isolate BI981 membrane protein (M) gene, complete cds", *NCBI*, 2 pages, Apr. 6, 2011.
GenBank Accession No. FJ687449.1, "Porcine epidemic diarrhea virus isolate BI976 membrane protein (M) gene, complete cds", *NCBI*, 2 pages, Apr. 6, 2011.
GenBank Accession No. AF500215.1, "Porcine epidemic diarrhea virus spike protein (Spk1) gene, complete cds", *NCBI*, 3 pages, Aug. 23, 2005.
GenBank Accession No. KF476061.1, "Porcine epidemic diarrhea virus isolate CHHEB ORF3 protein (ORF3) gene, complete cds", *NCBI*, 2 pages, May 5, 2014.
GenBank Accession No. KF476060.1, "Porcine epidemic diarrhea virus isolate CHZHZ-04 putative ORF3 protein (ORF3) gene, complete cds", *NCBI*, 2 pages, May 5, 2014.
GenBank Accession No. KF476059.1, "Porcine epidemic diarrhea virus isolate CHJCH ORF3 protein (ORF3) gene, complete cds", *NCBI*, 2 pages, May 5, 2014.
GenBank Accession No. KF476058.1, "Porcine epidemic diarrhea virus isolate CHXIP-03 putative ORF3 protein (ORF3) gene, complete cds", *NCBI*, 2 pages, May 5, 2014.
GenBank Accession No. KF476057.1, "Porcine epidemic diarrhea virus isolate CHLSHAN ORF3 protein (ORF3) gene, complete cds", *NCBI*, 2 pages, May 5, 2014.
GenBank Accession No. KF476056.1, "Porcine epidemic diarrhea virus isolate CHFH putative ORF3 protein (ORF3) gene, complete cds", *NCBI*, 2 pages, May 5, 2014.
GenBank Accession No. KF476055.1, "Porcine epidemic diarrhea virus isolate CHLH ORF3 protein (ORF3) gene, complete cds", *NCBI*, 2 pages, May 5, 2014.
GenBank Accession No. KF476054.1, "Porcine epidemic diarrhea virus isolate CHFCH-01 ORF3 protein (ORF3) gene, complete cds", *NCBI*, 2 pages, May 5, 2014.
GenBank Accession No. KF476053.1, "Porcine epidemic diarrhea virus isolate CHLY-09 ORF3 protein (ORF3) gene, complete cds", *NCBI*, 2 pages, May 5, 2014.
GenBank Accession No. KF476052.1, "Porcine epidemic diarrhea virus isolate CHXIP-01 ORF3 protein (ORF3) gene, complete cds", *NCBI*, 2 pages, May 5, 2014.
GenBank Accession No. KF476051.1, "Porcine epidemic diarrhea virus isolate CHKF-01 ORF3 protein (ORF3) gene, complete cds", *NCBI*, 2 pages, May 5, 2014.
GenBank Accession No. KF476050.1, "Porcine epidemic diarrhea virus isolate CHQX-02 ORF3 protein (ORF3) gene, complete cds", *NCBI*, 2 pages, May 5, 2014.
GenBank Accession No. KF476049.1, "Porcine epidemic diarrhea virus isolate CHXY-02 ORF3 protein (ORF3) gene, complete cds", *NCBI*, 2 pages, May 5, 2014.
GenBank Accession No. KF476048.1, "Porcine epidemic diarrhea virus isolate CHYF-01 ORF3 protein (ORF3) gene, complete cds", *NCBI*, 2 pages, May 5, 2014.

(56) References Cited

OTHER PUBLICATIONS

GenBank Accession No. KF177258.1, "Porcine epidemic diarrhea virus isolate YJ7C spike protein (S) gene, complete cds", *NCBI*, 3 pages, Sep. 18, 2013.
GenBank Accession No. KF177257.1, "Porcine epidemic diarrhea virus isolate YJ3F spike protein (S) gene, complete cds", *NCBI*, 3 pages, Sep. 18, 2013.
GenBank Accession No. KF177256.1, "Porcine epidemic diarrhea virus isolate JY7C spike protein (S) gene, complete cds", *NCBI*, 3 pages, Sep. 18, 2013.
GenBank Accession No. KF177255.1, "Porcine epidemic diarrhea virus isolate JY6C spike protein (S) gene, complete cds", *NCBI*, 3 pages, Sep. 18, 2013.
GenBank Accession No. NC_002645, "Human coronavirus 229E, complete genome", *NCBI*, 12 pages, Apr. 28, 20710.
GenBank Accession No. NC_005831, "Human coronavirus NL63, complete genome", *NCBI*, 11 pages, Mar. 29, 2016.
GenBank Accession No. EF203066, "Bat coronavirus HKU2 strain HKU2/HK/298/2006, complete genome", *NCBI*, 12 pages, Oct. 9, 2007.
GenBank Accession No. EF203067.1, "Bat coronavirus HKU2 strain HKU2/HK/33/2006, complete genome", *NCBI*, 12 pages, Oct. 9, 2007.
GenBank Accession No. EF203065, "Bat coronavirus HKU2 strain HKU2/HK/46/2006, complete genome", *NCBI*, 12 pages, Oct. 9, 2007.
GenBank Accession No. EF203064, "Bat coronavirus HKU2 strain HKU2/GD/430/2006, complete genome", *NCBI*, 12 pages, Oct. 9, 2007.
GenBank Accession No. DQ339101, "Human coronavirus HKU1 strain N5P8 genotype A/B recombinant, complete genome", *NCBI*, 12 pages, Jun. 30, 2006.
GenBank Accession No. NC_001846, "Mouse hepatitis virus strain MHV-A59 C12 mutant, complete genome", *NCBI*, 12 pages, Mar. 29, 2016.
GenBank Accession No. NC_007732, "Porcine hemagglutinating encephalomyelitis virus, complete genome", *NCBI*, 13 pages, Dec. 1, 2009.
GenBank Accession No. NC_005147, "Human coronavirus OC43, complete genome", *NCBI*, 13 pages, Dec. 13, 2013.
GenBank Accession No. NC_003045, "Bovine coronavirus, complete genome", *NCBI*, 16 pages, Feb. 10, 2015.
GenBank Accession No. EF065514, "Bat coronavirus HKU9-2, complete genome", *NCBI*, 11 pages, Feb. 7, 2007.
GenBank Accession No. NC_009021, "Bat coronavirus HKU9-1, complete genome", *NCBI*, 12 pages, Dec. 8, 2008.
GenBank Accession No. EF065515, "Bat coronavirus HKU9-3, complete genome", *NCBI*, 11 pages, Feb. 7, 2007.
GenBank Accession No. EF065516, "Bat coronavirus HKU9-4, complete genome", *NCBI*, 11 pages, Feb. 7, 2007.
GenBank Accession No. DQ001339, "Avian infectious bronchitis virus isolate IBV-p65, complete genome", *NCBI*, 11 pages, Oct. 17, 2005.
Akerström et al. "Protein G: a powerful tool for binding and detection of monoclonal and polyclonal antibodies", *J Immunol* 1985; 135:2589-2592.
Chen et al. "Boosting with recombinant vacccinia increases HPV-16 E7-specific T cell precursor frequencies of HPV-16 E7-expressing DNA vaccines", *Vaccine*, 18(19):2015-2022, Apr. 3, 2000 (Abstract Only).
Gonzalo et al. "Enhanced CD8+ T cell response to HIV-1 env by combined immunization with influenza and vaccinia virus recombinants", *Vaccine*, 17(7-8):887-892, Feb. 26, 1999 (Abstract Only).
Hanke et al. "Enhancement of MHC class I-restricted peptide-specific T cell induction by a DNA prime/MVA boost vaccination regime", *Vaccine*, 16(5):439-445, Mar. 1998 (Abstract Only).
Huse et al. "Generation of a large combinatorial library of the immunoglobulin repertoire in phage lambda", *Science*, Dec. 8, 1989, vol. 246, Issue 4935, pp. 1275-1281 (Abstract Only).
Kohler and Milstein, "Continuous cultures of fused cells secreting antibody of predefined specificity", *Nature*, vol. 256:494-497, Aug. 7, 1975.
Kronvall et al. "A Surface Component in Group A, C, and G Streptococci with Non-Immune Reactivity for Immunoglobulin G", *J. Immunol.* 111:1401-1406 (1973).
Maddox et al. "Elevated Serum Levels in Human Pregnancy of a Molecule Immunochemically Similar to Eosinophil Granule Major Basic Protein", *J. Exp. Med.* 158:1211-1226 (Oct. 1983).
Pancholi et al. "DNA Prime-Canarypox Boost with Polycistronic Hepatitis C Virus (HCV) Genes Generates Potent Immune Responses to HCV Structural and Nonstructural Proteins", *J. Infect. Dis.* 182:18-27, 2000.
Walker et al. "Interaction of human IgG chimeric antibodies with the human FcRI and FcRII receptors: requirements for antibody-mediated host cell-target cell interaction", *Molec. Immunol.* Apr. 1989; 26(4):403-411 (Abstract Only).
International Preliminary Report on Patentability Corresponding to International Application No. PCT/US2015/021773; dated Sep. 29, 2016; 8 pages.

A.

B.

- nsp5, S and M common to MA 15
- Identifies mutation spectra for cross-species transmission

*Sequencing in progress

Recombinant S Gene Constructs

MERS-CoV Spike

BtCoV HKU4.2 Spike

Boundaries of each antigen in the Chimera Mix

HKU 4.2 Spike aa 1-371

MERSCoV RBD aa 367-588

HKU4.2 Spike aa 593-983

BtCoV HKU 5.5 Spike aa 984-1353

Ectodomain | RBD | S1/S2 | S2/Tm
1    371   367-588    730

Chimeric Antigen 2C

BtCoV HKU 5 Spike

A.

BtSARS.HKU3 genomes 1-3
BtSARS.Rm1
BtCoV.279.2005
BtCoV.273.2005
BtSARS.RP3
SARS-CoV reps from All phases/civets/dogs Subgroup 2b

B.

Mock | CHIMERA S | SARS CoV S | Urbani S

Mock | CHIMERA S | SARS CoV S | Urbani S

α Chimera S        α SARSCoV S

C. Recombinant S Gene Constructs

SARS-CoV (Urbani)*

BtCoV/ HKU3*

BtCoV HKU 3 Spike | SARS-CoV RBD | BtCoV HKU3 Spike | BtCoV 279 Spike
Ectodomain | RBD | S1/S2 | S2/Tm   Chimera S BtCoV/279/04-S

| Virus | Nucleotide Change | Affected Gene | Amino Acid Change |
|---|---|---|---|
| HKU3-SRBD-MAv | C10334T | nsp5 | Silent |
| | T10846C | nsp5 | Silent |
| | C23304T | Spike | P611S |
| | A24966G | Spike | I1165V |
| | 26397_del_12nt_26398 | Membrane (M) | Deletes 4 aa (3DNGT6) |
| | 27661^T^27663 | ORF7b | Truncates protein at 23 aa (last 10 aa are altered) |

METHODS AND COMPOSITIONS FOR CHIMERIC CORONAVIRUS SPIKE PROTEINS

STATEMENT OF PRIORITY

This application is a 35 U.S.C. §371 national phase application of International Application Serial No. PCT/US2015/021773, filed Mar. 20, 2015, which claims the benefit, under 35 U.S.C. § 119(e), of U.S. Provisional Application Ser. No. 61/968,279, filed Mar. 20, 2014, the entire content of each of which is incorporated by reference herein.

STATEMENT OF FEDERAL SUPPORT

This invention was made with government support under Grant No. U54AI057157 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-672_ST25.txt, 90,897 bytes in size, generated on Dec. 9, 2016 and filed via EFS-Web, is provided in lieu of a paper copy. This Sequence Listing is hereby incorporated by reference into the specification for its disclosures.

FIELD OF THE INVENTION

The present invention relates to methods and compositions comprising a chimeric coronavirus spike protein for treating and/or preventing a disease or disorder caused by a coronavirus infection.

BACKGROUND OF THE INVENTION

Updated approaches are needed to rapidly respond to new emerging diseases, especially early in the epidemic when prompt public health intervention strategies can limit mortality and epidemic spread. In particular, emerging respiratory coronaviruses offer a considerable threat to the health of global populations and the economy. Coronaviruses (CoVs) constitute a group of phylogenetically diverse enveloped viruses that encode the largest plus strand RNA genomes and replicate efficiently in most mammals. Human CoV (HCoVs-229E, OC43, NL63, and HKU1) infections typically result in mild to severe upper and lower respiratory tract disease. Severe Acute Respiratory Syndrome Coronavirus (SARS-CoV) emerged in 2002-2003 causing acute respiratory distress syndrome (ARDS) with 10% mortality overall and up to 50% mortality in aged individuals. Middle Eastern Respiratory Syndrome Coronavirus (MERS-CoV) emerged in the Middle East in April of 2012, manifesting as severe pneumonia, acute respiratory distress syndrome (ARDS) and acute renal failure. The virus is still circulating and has been shown to have a mortality rate of ~49%. Platforms for generating reagents and therapeutics are needed to detect and control the emergence of new strains, especially early in an outbreak prior to the development of type specific serologic reagents and therapeutics.

The present invention overcomes previous shortcomings in the art by providing methods and compositions comprising a chimeric coronavirus spike protein for treating/and or preventing diseases and disorders caused by infection by a coronavirus.

SUMMARY OF THE INVENTION

In one aspect, the present invention provides a chimeric coronavirus spike protein comprising, in orientation from amino to carboxy terminus: a) a first region comprising a portion of a coronavirus spike protein ectodomain that precedes the receptor binding domain (RBD) as located in a nonchimeric coronavirus spike protein, of a first coronavirus; b) a second region comprising a coronavirus spike protein receptor binding domain (RBD) of a second coronavirus that is different from said first coronavirus; c) a third region comprising a portion of a coronavirus spike protein S1 domain as located in a nonchimeric coronavirus spike protein immediately downstream of the RBD, contiguous with a portion comprising a coronavirus spike protein S2 domain as located immediately upstream of a fusion protein domain in a nonchimeric coronavirus spike protein, wherein said third region is of said first coronavirus; and d) a fourth region comprising a portion of a coronavirus spike protein from the start of the fusion protein domain through the carboxy terminal end as located in a nonchimeric coronavirus spike protein of a third coronavirus that is different from said first coronavirus and said second coronavirus.

In further aspects, the present invention further provides an isolated nucleic acid molecule encoding the chimeric coronavirus spike protein of this invention, as well as a vector comprising the isolated nucleic acid molecule. Also provided are compositions comprising the chimeric coronavirus spike proteins, isolated nucleic acid molecules and/or vectors of this invention in a pharmaceutically acceptable carrier.

In further aspects, the present invention provides a method of producing an immune response to a coronavirus in a subject, treating a coronavirus infection in a subject, preventing a disease or disorder caused by coronavirus infection in a subject and/or protecting a subject from the effects of coronavirus infection, comprising administering to the subject an effective amount of the chimeric coronavirus spike protein, the isolated nucleic acid molecule the vector and/or the composition of this invention, or any combination thereof, thereby producing an immune response to a coronavirus in the subject, treating a coronavirus infection in the subject, preventing a disease or disorder caused by coronavirus infection in the subject and/or protecting the subject from the effects of coronavirus infection.

In further aspects, the present invention provides a method of identifying a coronavirus spike protein for administration to elicit an immune response to coronavirus in a subject infected by a coronavirus and/or a subject at risk of coronavirus infection and/or to a subject for whom eliciting an immune response to a coronavirus is needed or desired, comprising: a) contacting a sample obtained from a subject infected with a coronavirus with a panel of proteins comprising: 1) one or more chimeric coronavirus spike proteins from a subgroup 2c coronavirus, 2) one or more chimeric coronavirus spike proteins from a subgroup 2b coronavirus, 3) one or more spike proteins from a subgroup 2a coronavirus, 4) one or more chimeric coronavirus spike proteins from a subgroup 2d coronavirus, 5) one or more chimeric coronavirus spike proteins from a subgroup 1a coronavirus, 6) one or more chimeric coronavirus spike proteins from a subgroup 1b coronavirus, and 7) any combination of (1) through (6) above, under conditions whereby an antigen/ antibody complex can form; and b) detecting formation of an antigen/antibody complex, whereby detection of formation of the antigen/antibody complex comprising the chimeric coronavirus spike protein(s) of any of (1)-(6) identifies the presence of antibodies to a spike protein of the coronavirus that is infecting the subject of (a), thereby identifying a coronavirus spike protein for administration to the subject of (a) and/or to a subject infected with a coronavirus and/or to a subject at risk of coronavirus infection and/or to a subject for whom eliciting an immune response to a coronavirus is needed or desired.

Also provided herein is a method of identifying an antibody that neutralizes a coronavirus infecting a subject, comprising: a) isolating a coronavirus from a sample of a subject infected with a coronavirus and/or suspected of being infected with a coronavirus; b) contacting the coronavirus of (a) with a panel of antibodies comprising: 1) an antibody reactive with a chimeric coronavirus spike protein from a subgroup 2c coronavirus, 2) an antibody reactive with a chimeric coronavirus spike protein from a subgroup 2b coronavirus, 3) an antibody reactive with a chimeric coronavirus spike protein from a subgroup 2a coronavirus, 4) an antibody reactive with a chimeric coronavirus spike protein from a subgroup 2d coronavirus, 5) an antibody reactive with a chimeric coronavirus spike protein from a subgroup 1a coronavirus, 6) an antibody reactive with a chimeric coronavirus spike protein from a subgroup 1b coronavirus, and 7) any combination of (1) through (6) above, to form respective coronavirus/antibody compositions, each comprising a respective antibody of the panel; c) contacting each of the respective coronavirus/antibody compositions of (b) with cells susceptible to coronavirus infection under conditions whereby coronavirus infection can occur; and d) detecting the presence or absence of infection of the cells, whereby absence of detection of infection of the cells contacted with any of the coronavirus/antibody compositions of (b) identifies the antibody of that coronavirus/antibody composition as an antibody that neutralizes the coronavirus infecting the subject.

The foregoing and other objects and aspects of the present invention are explained in detail in the specification set forth below.

Panel C. Western blot from independent experiments showing expression of SARS-CoV S protein from VRP 3526 S and VRP 3000 S vaccines in Vero cells. Lower panel indicates actin.

Figure 11:
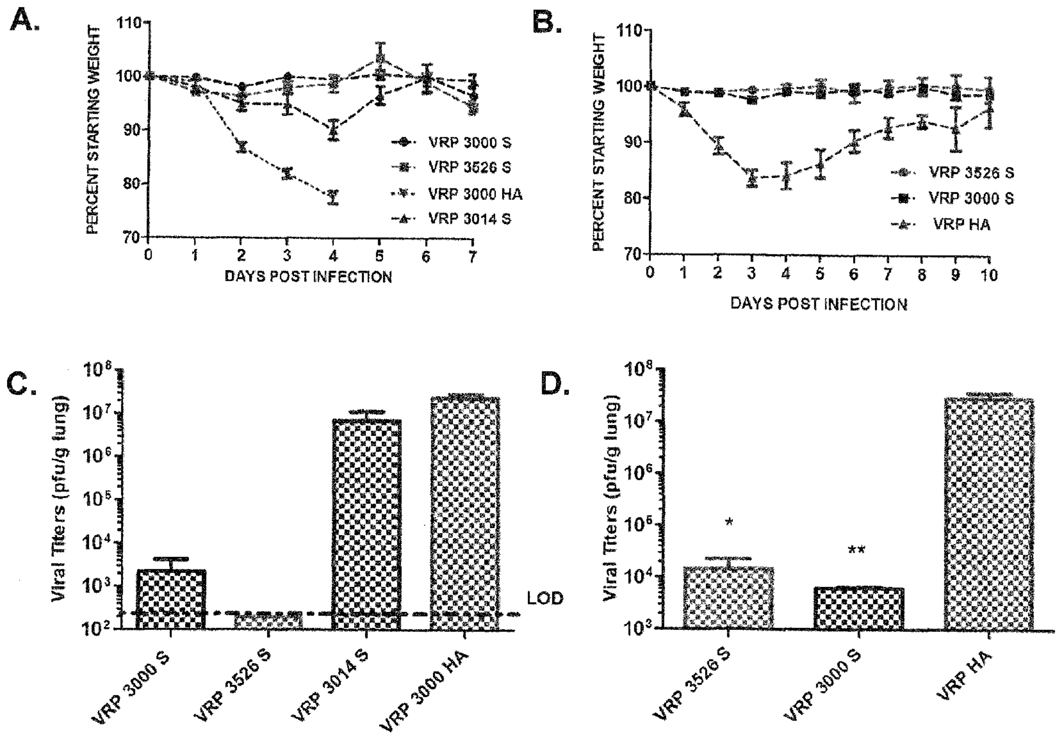

FIG. 11. Young adult mice are protected from homologous (MA15) and heterologous (MA 15 GD03S) SARS-CoV challenge by VRP 3526 S vaccine. Panels A & B. Percent weight loss of young adult mice immunized with indicated vaccines, and challenged with 105 pfu of rMA15 (homologous) and rMA15-GD03S (heterologous) respectively. Panels C&D. Lung titers on 2 DPI infection determined by plaque assay Vero cells from experiments in Panel A and B respectively. Error bars indicate SEM. * indicates ($p<0.05$ in Mann-Whitney Test).

Figure 12:
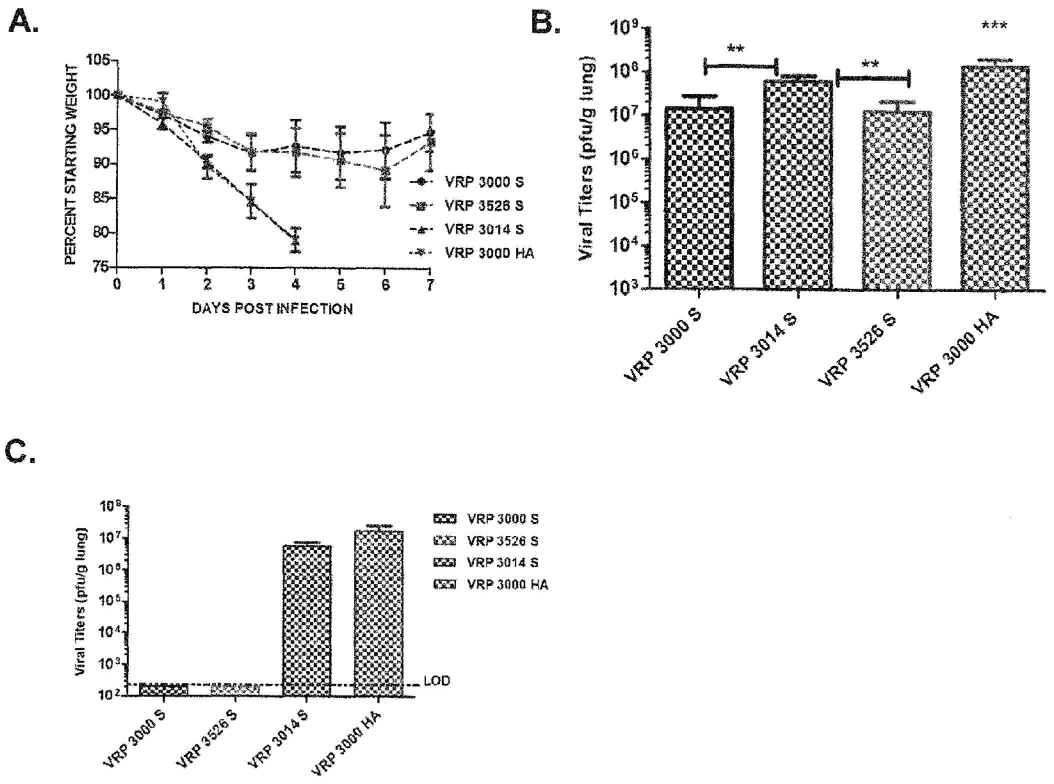

FIG. 12. Aged mice are protected from homologous (MA15) SARS-CoV challenge by VRP 3526 S vaccine. Panel A. Percent weight loss of one year old mice immunized with S protein based vaccines from three different coats, and challenged with 105 pfu of rMA15. Panel B and C. Lung titers on 2 DPI (Panel B), and 4 DPI (Panel C) determined by plaque assay Vero cells. Error bars indicate SEM. Significance as determined by Mann-Whitney test ($p<0.05$, indicated by asterisk).

Figure 13:
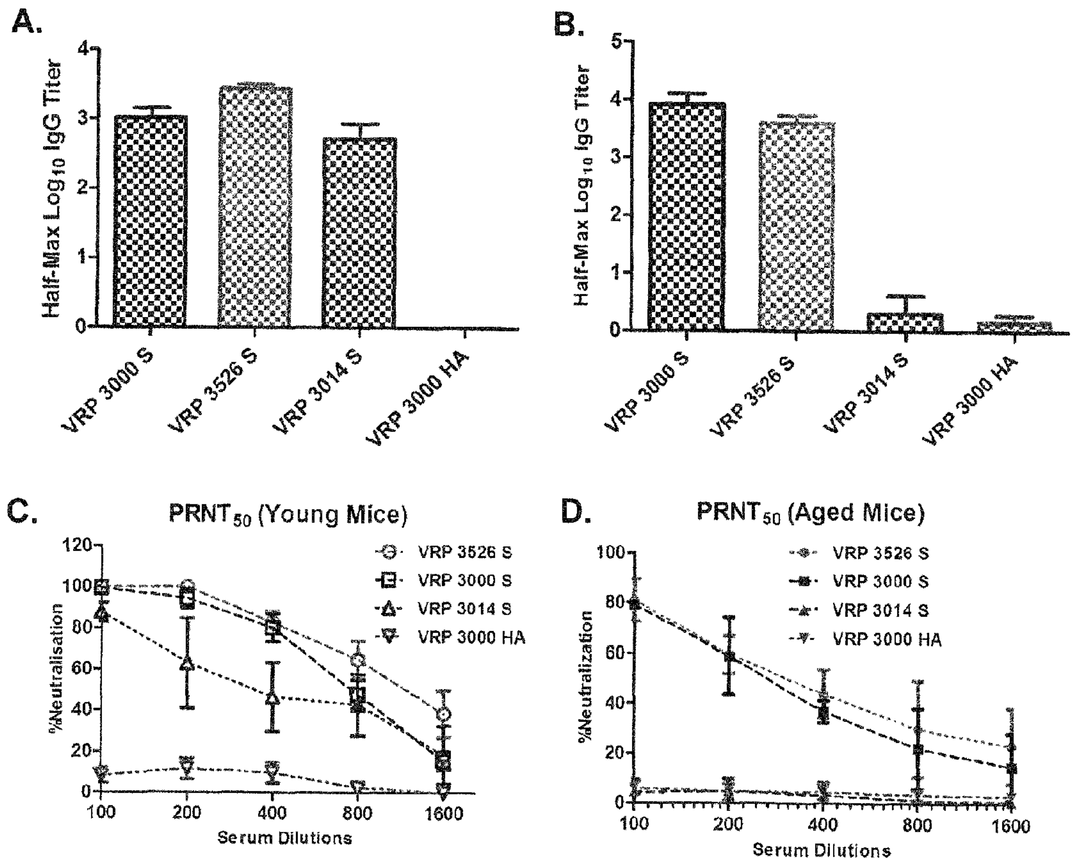

FIG. 13. VRP 3526 elicits high Antibody response in young and aged animals. Panels A and B. ELISA results showing IgG titers to S protein, elicited in young mice (Panel A) and aged mice (Panel B) by indicated vaccine groups. Panels C and D. Neutralization potential (to SARS-CoV) of antibodies elicited by indicated vaccine groups in young mice (Panel C), and aged mice (Panel D), as measured by $PRNT_{50}$ assay. Error bars indicate SD.

Figure 14:
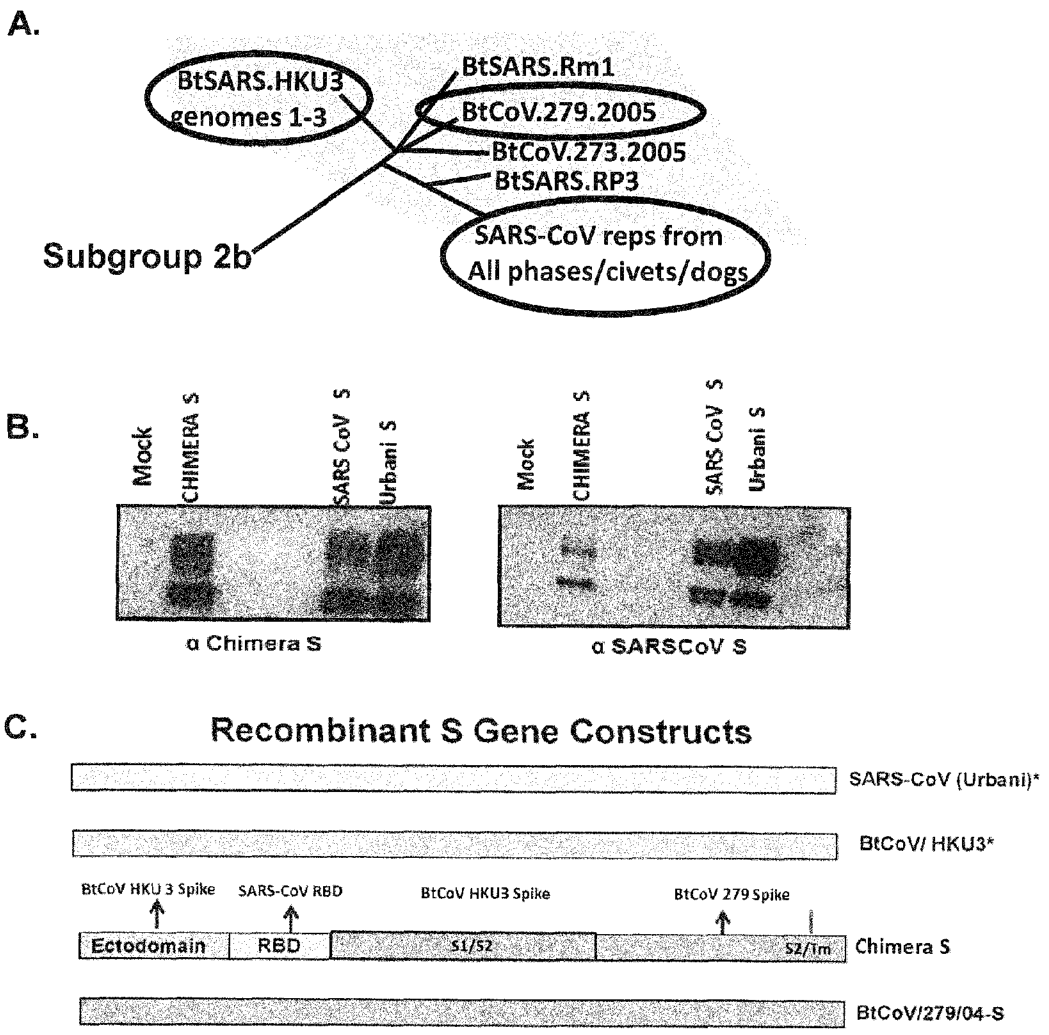

FIG. 14. Design of a Chimeric Spike based CoV Vaccine. Panel A. Phylogenetic tree showing Coronaviruses in subgroup 2b. The circles represent three viruses from which specific regions of S proteins are combined to form the chimeric spike. Panel B. Western blots showing that serum raised to the Chimera S or SARS-CoV Urbani S recognize the Chimeric Spike due to overlapping epitopes. Panel C. Design of the Chimeric Spike antigen utilizing portions of SARS-COV, BtCoV HKU3 and BtCoV 279 Spike. The Chimera S contains the following epitopes from N terminus: a portion of ectodomain from BtCoV HKU3; a portion of Receptor Binding Domain (RBD) from SARS-CoV; a region from S1/S2 from BtCoV HKU3; followed by a region containing S2/Tm from the BtCoV 279 Spike.

Figure 15:
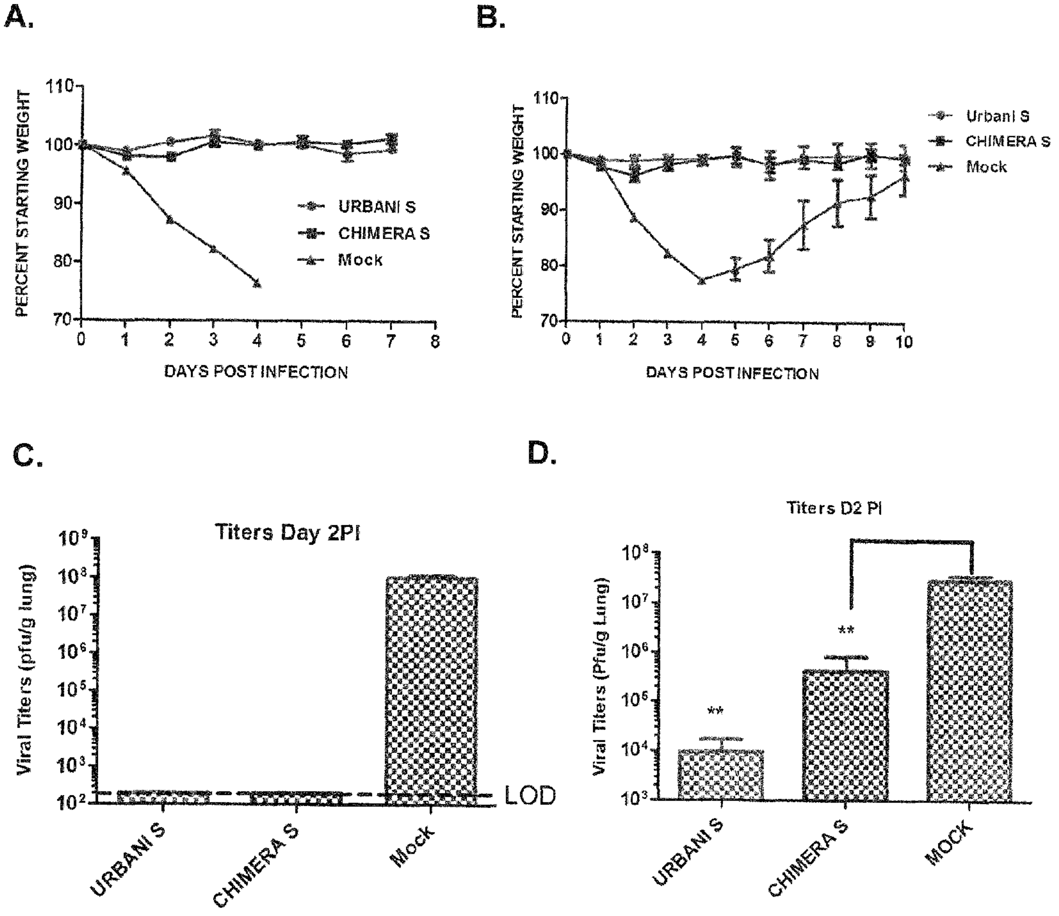

FIG. 15. Chimera S Vaccine Protects from Homologous and Heterologous SARS-CoV Challenge. Panels A & B. Percent weight loss of young adult mice immunized with S protein based or Chimera S vaccine and challenged with $10^5$ pfu of rMA15 (homologous) and rMA15-GD03S (heterologous) respectively. Panels C & D. Lung titers on 2 DPI infection determined by plaque assay Vero cells from experiments in Panel A and B respectively. Error bars indicate SEM. * indicates ($p<0.05$ in Mann-Whitney Test).

Figure 16:
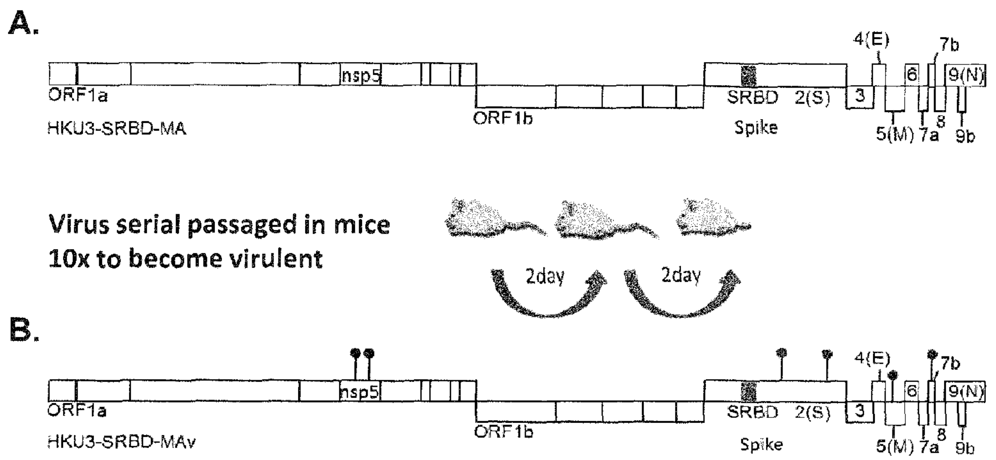

FIG. 16. Generation and Mouse Adaptation of a lethal Zoonotic Challenge Virus (BtCoV HKU3) from subgroup 2b. Panel A. Schematic of chimeric HKU3 virus (HKU3-SRBD-MA) containing the Receptor binding domain (green color) from SARS-CoV S protein. The Open Reading Frames are Indicated. The asterisk indicates Y436H mutation which enhances replication in mice. HKU3-SRBD-MA was serially passaged in 20 week old BALB/c mice (schematic below) at 2 day intervals to create a lethal challenge virus. Panel B. Mouse adaptation leads to mutations in nsp5, Spike, Membrane and ORF 7b. The mutations are indicated by lollipops, and the table shows the exact nucleotide and amino acid mutations are indicated in the table.

Figure 17:
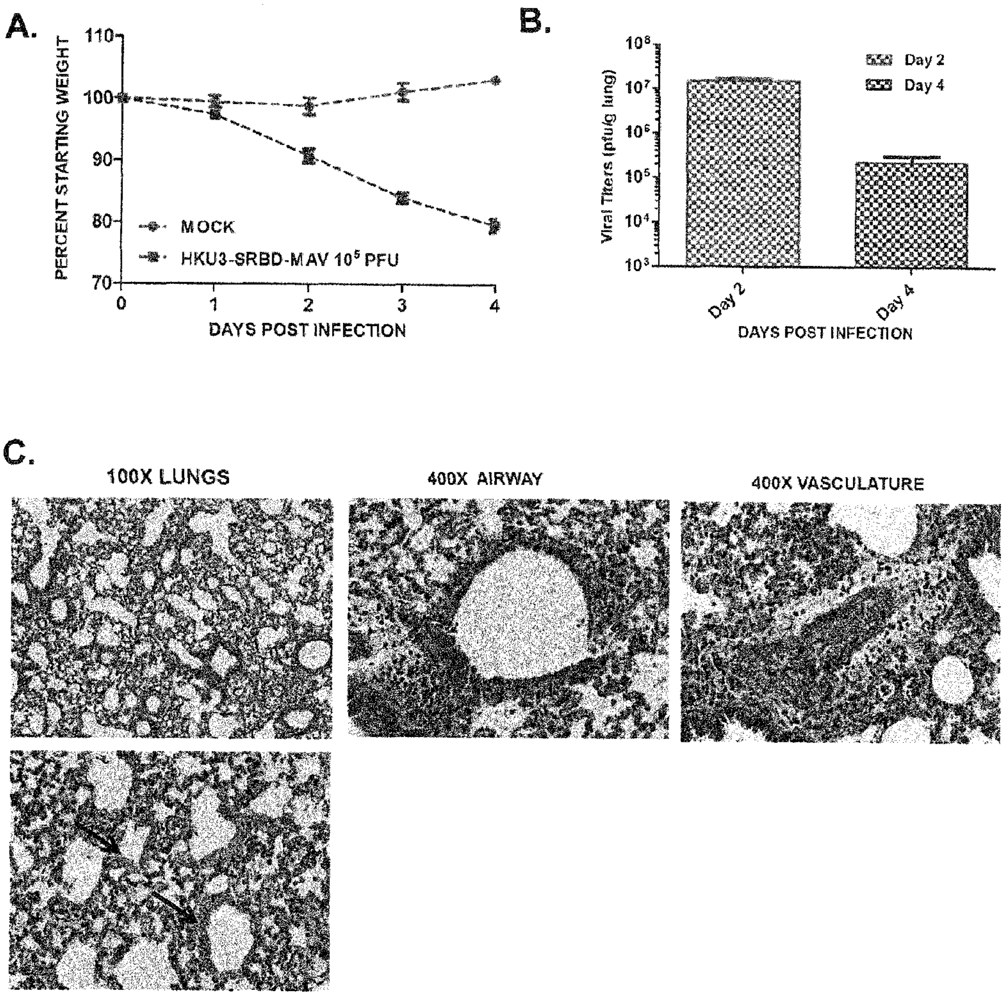

FIG. 17. HKU-3-SRBD-MAv causes severe respiratory disease in 20 wk old Balb/c mice culminating in lethality. Panel A. Percent weight loss of 20 wk old Balb/c mice infected with $10^5$ pfu of HKU3-SRBD-$MA_V$, through 4 days post infection. Note that the infected mice lose 20% of their body weight 4 days post infection. Panel B. Viral titers in lungs of mice at Day 2 and 4 post infection. Panel C. Histopathology of H&E stained lung sections at day 4 P.I. showing denuded airways, perivascular cuffing and formation of hyaline membranes (black arrow), which are markers of severe lung disease.

Figure 18:
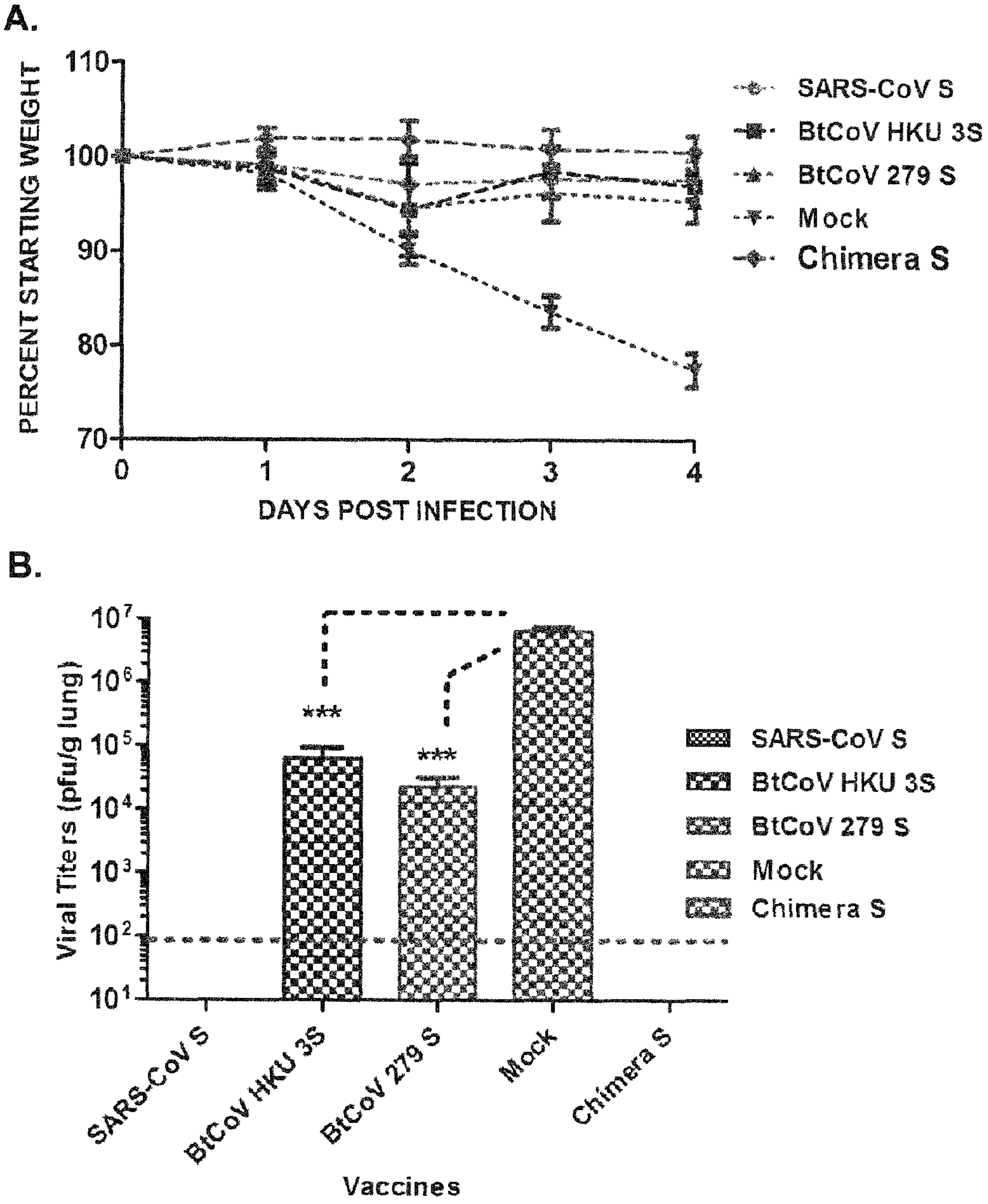

FIG. 18. Chimera S vaccine protects mice from HKU3-SRBD-MAv Challenge. Panel A. Percent weight loss of 20 wk old Balb/C mice immunized with SARS CoV S, BtCoV HKU3S, BtCoV 279S, Chimera S or mock vaccinated and challenged with $10^5$ pfu of HKU3-SRBD-MAv. Panel B. Lung titers on 2 DPI infection determined by plaque assay Vero cells Error bars indicate SEM. * indicates ($p<0.05$ in Mann-Whitney Test).

DETAILED DESCRIPTION OF THE INVENTION

The present invention is based on the production and development of a chimeric coronavirus spike protein which induces a neutralizing immune response to coronavirus, for use for example, in the treatment and/or prevention of a disease or disorder caused by infection by a variety of different coronavirus strains.

Thus, in one aspect, the present invention provides a chimeric coronavirus spike protein comprising, in orientation from amino to carboxy terminus: a) a first region comprising a portion of a coronavirus spike protein ectodomain that precedes the receptor binding domain (RBD) as located in a nonchimeric coronavirus spike protein, of a first coronavirus; b) a second region comprising a coronavirus spike protein receptor binding domain (RBD) of a second coronavirus that is different from said first coronavirus; c) a third region comprising a portion of a coronavirus spike protein 51 domain as located in a nonchimeric coronavirus spike protein immediately downstream of the RBD, contiguous with a portion comprising a coronavirus spike protein S2 domain as located immediately upstream of a fusion protein domain in a nonchimeric coronavirus spike protein, wherein said third region is of said first coronavirus; and d) a fourth region comprising a portion of a coronavirus spike protein from the start of the fusion protein domain through the carboxy terminal end as located in a nonchimeric coronavirus spike protein of a third coronavirus that is different from said first coronavirus and said second coronavirus.

By "orientation from amino to carboxy terminus" it is meant that the regions of the chimeric coronavirus spike protein are present from left to right in the same orientation as the amino terminus and carboxy terminus of a protein. This term is intended to describe orientation only and does not mean that the first region as described in the chimeric coronavirus structural protein is present at the exact amino terminus in all embodiments although that could be the case in some embodiments. Similarly this term does not mean that the fourth region as described in the chimeric coronavirus structural protein is present at the exact carboxy terminus in all embodiments although that could be the case in some embodiments.

Figure 1:
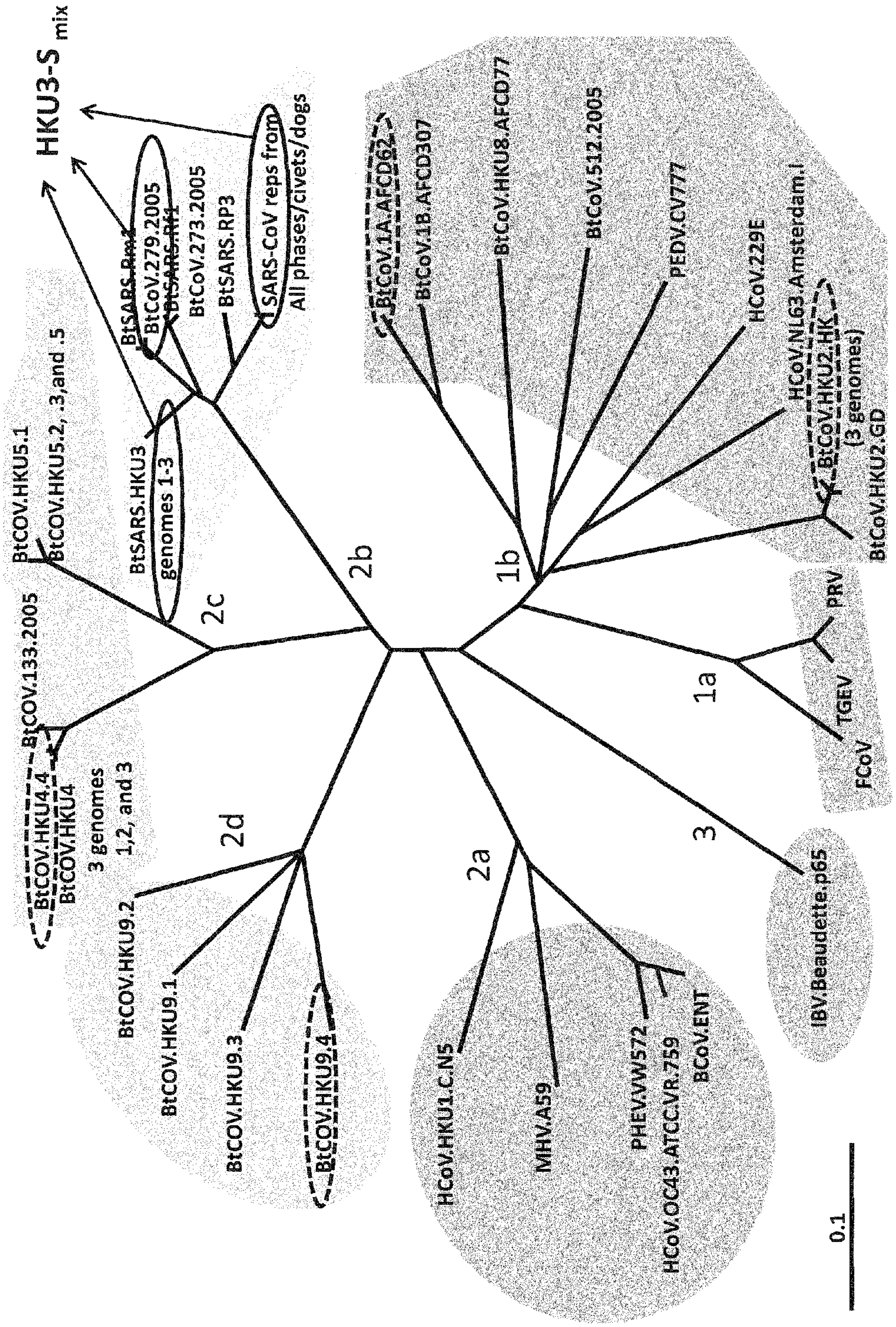
FIG. 1. Phylogenetic tree of the coronaviruses. The chimeric spike antigen HKU3-Smix belongs to subgroup 2b, and the antigenic components of the chimeric antigen are derived from BtCoV HKU 3S, SARS CoV S, and BtCoV 279 S, all of which are circled. The other S antigens representing other subgroups of CoVs are indicated in dashed circles as controls.
Figure 2:
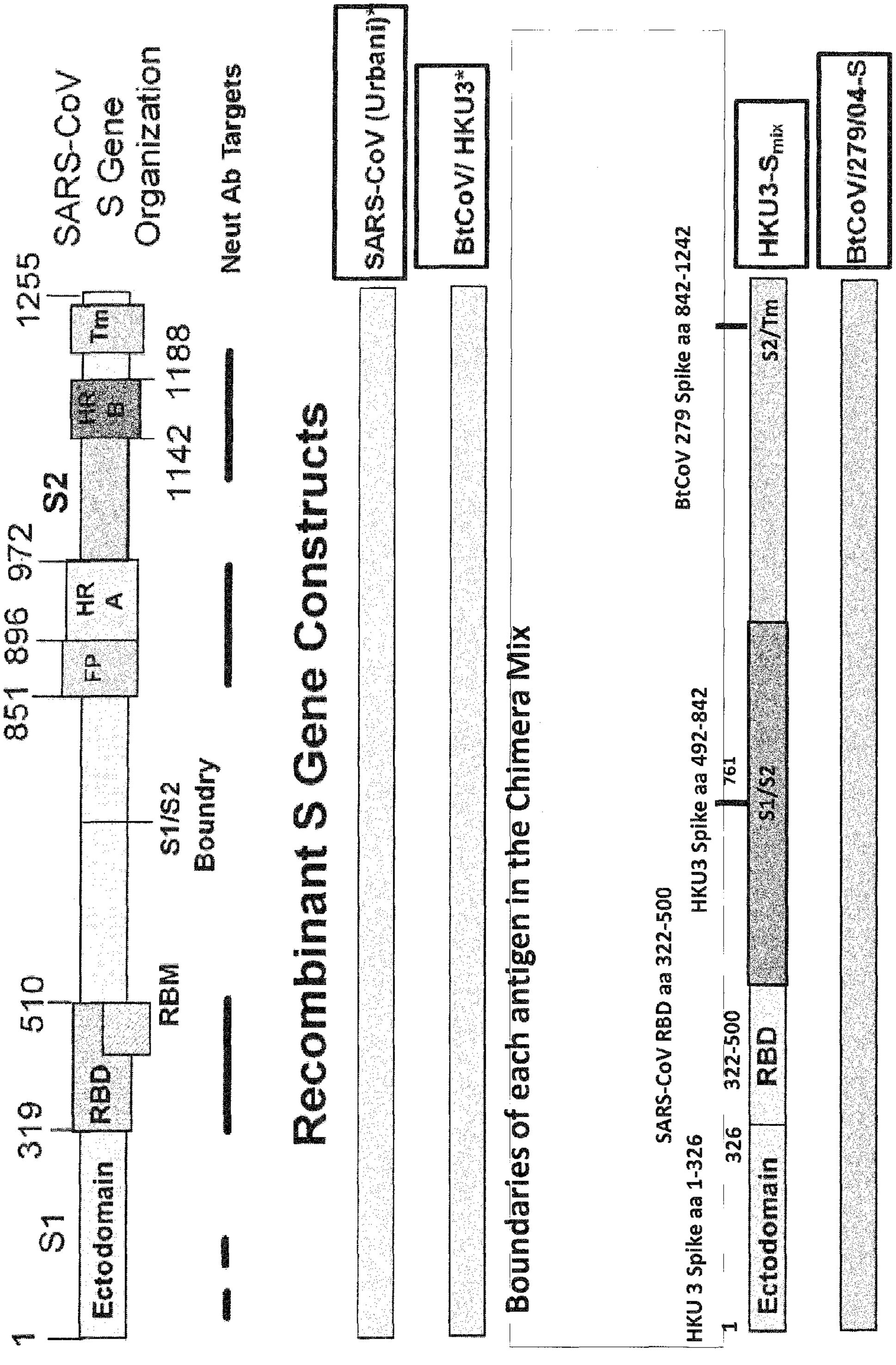
FIG. 2. Design of the chimeric spike antigen. The chimeric spike antigen HKU3-Smix has components from HKU3 S, SARS CoV S RBD, and BtCoV 279S. The specific amino acid residues adopted from each of the spike proteins are indicated in the figure. The S1/S2 boundary is indicated (761aa). S2/Tm domain is indicated (1194aa). The top panel represents the spike protein organization in the SARS-CoV Spike, showing the spread of the neutralizing epitope across various domains of the SARS-CoV spike protein.
Figure 3:
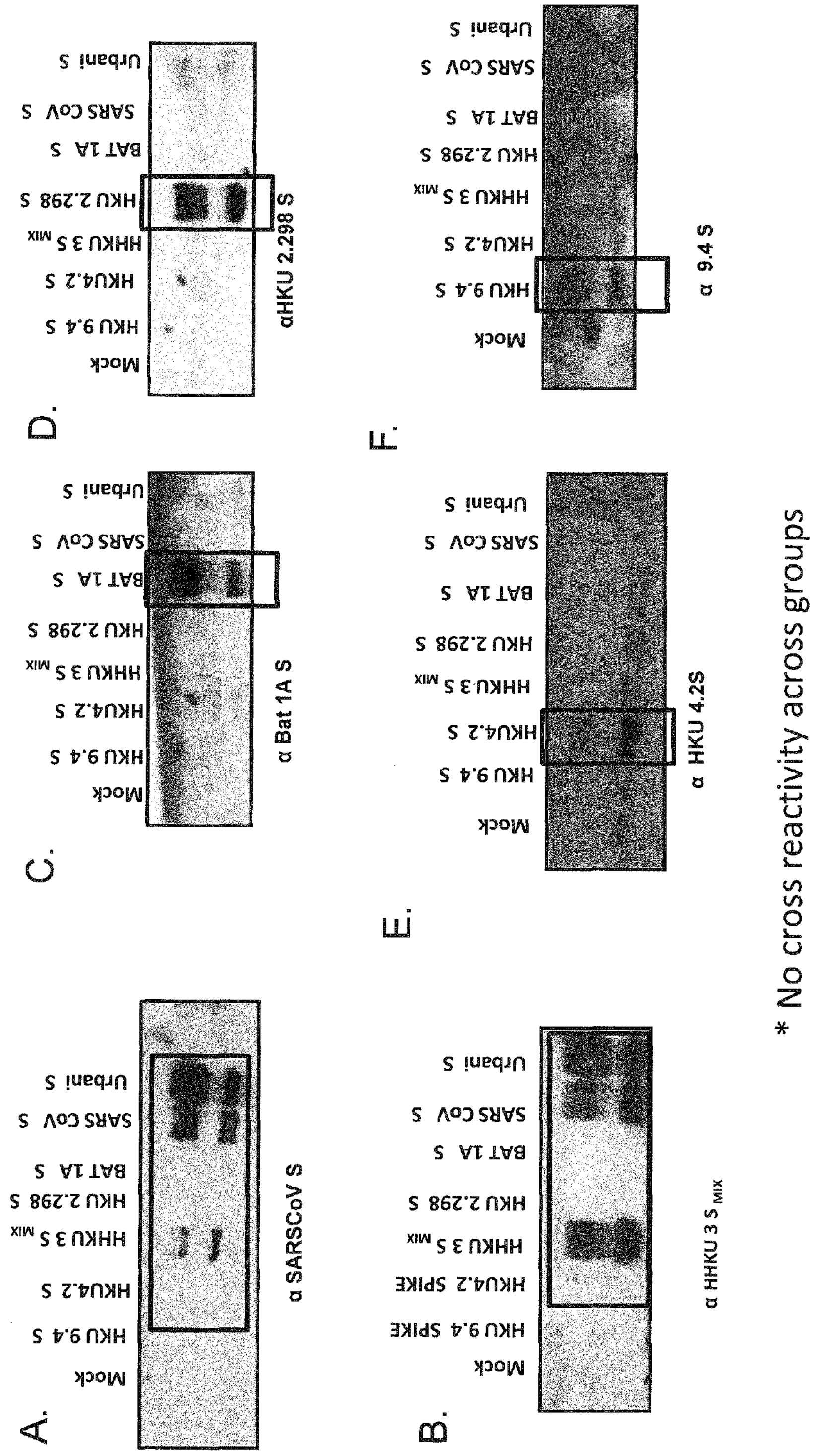
FIG. 3. Cross reactivity of antisera to chimeric spike antigen, with spike proteins from different CoVs. Mouse antisera to chimeric spike antigen (HKU 3 $S_{MIX}$), SARS S, BAT 1A S, HKU2.298 S, HKU 4.2 S, and HKU9.4S were analyzed for their cross reactivity with these antigens. Antisera to chimeric spike antigen recognizes SARS S (Panel B) and vice versa (Panel A). Note that there is no cross reactivity between S proteins of other subgroups.
Figure 4:
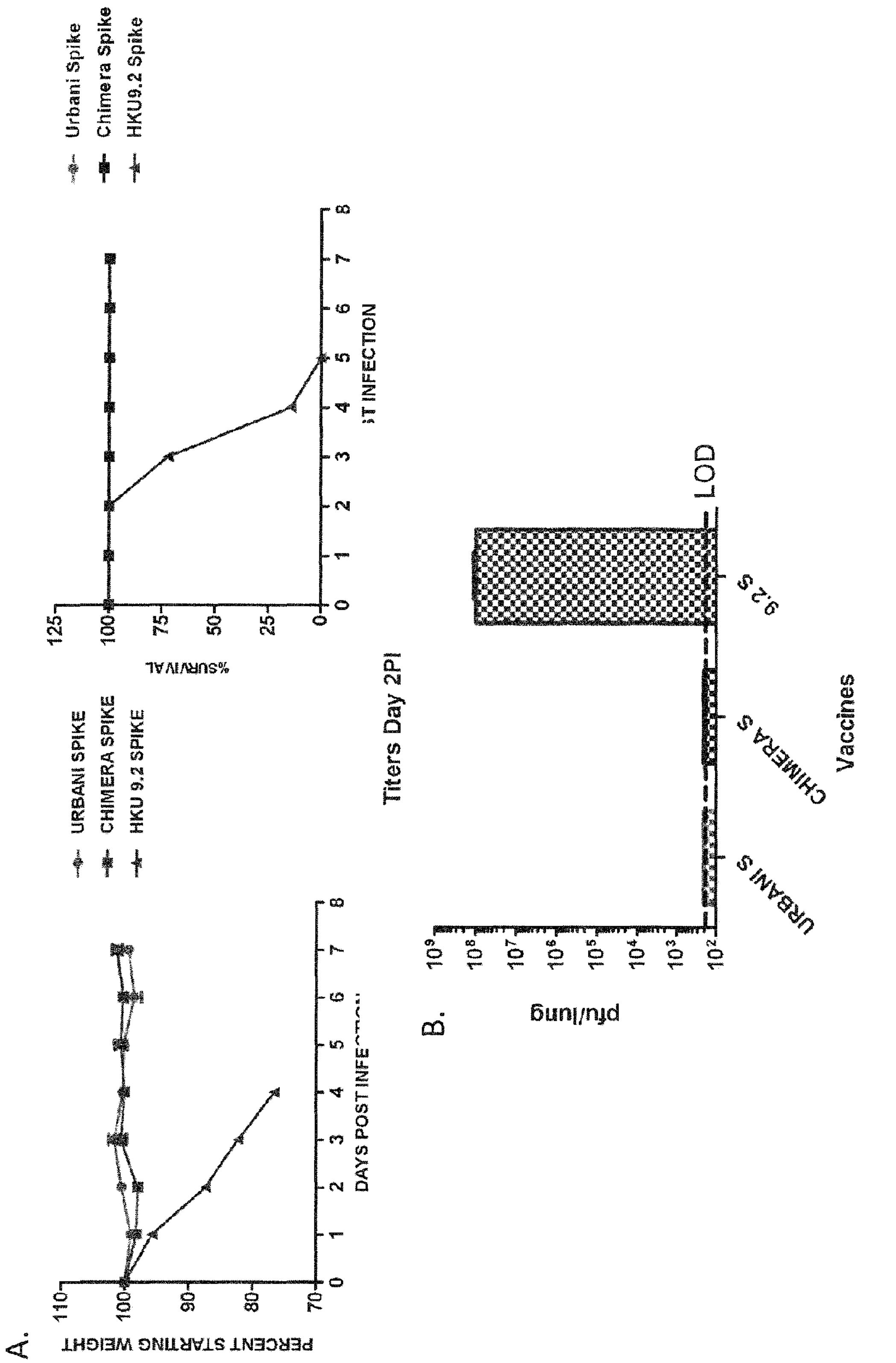
FIG. 4. Chimeric antigen HKU 3 $S_{MIX}$ protects against lethal SARS CoV challenge. Panel A. Percent weight loss of young Balb/C mice immunized with chimeric Antigen HKU 3 $S_{MIX}$, SARS S and HKU9.4S (negative control) and challenged with lethal dose of mouse adapted SARS CoV (MA 15 virus). Mice immunized with chimeric antigen, SARS S show no weight loss. Panel B. Lung titers on Day 2 post infection of the same groups of mice shown above. Note that there is no virus detected in groups of mice vaccinated with HKU 3 $S_{MIX}$ and SARS S.
Figure 5:
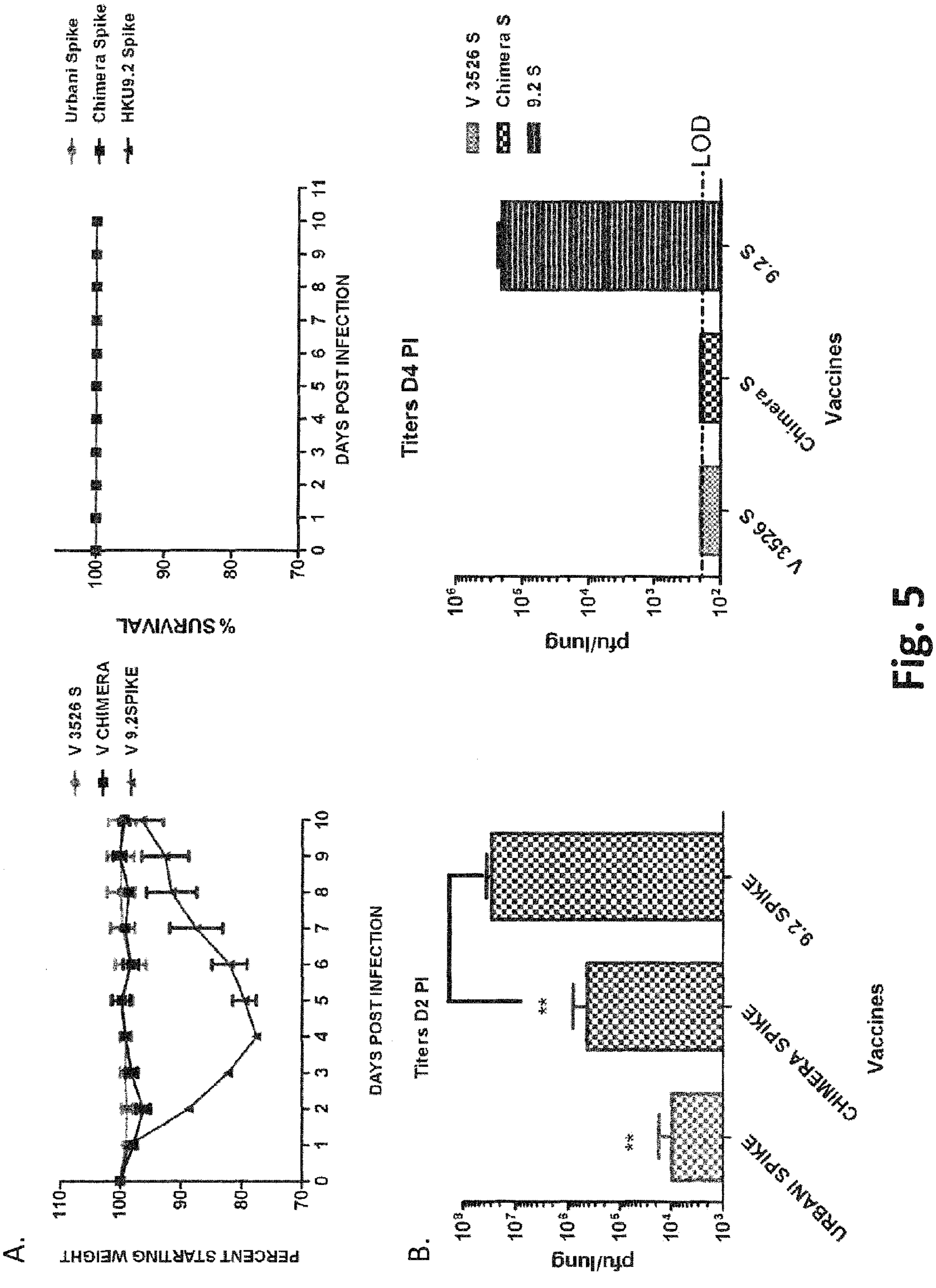
FIG. 5. Chimeric antigen HKU 3 $S_{MIX}$ protects against lethal SARS CoV heterologous challenge. Panel A. Percent weight loss of young Balb/C mice immunized with chimeric spike antigen HKU 3 $S_{MIX}$, SARS S and HKU9.4S (negative control) and challenged with lethal dose of heterologous mouse adapted SARS CoV (GD03 MA virus). Mice immunized with chimeric spike antigen, SARS S show no weight loss. Panel B. Lung titers on Day 2 post infection of the same groups of mice shown above. Viral replication is reduced on D2 and no virus is detected in groups of mice vaccinated with HKU 3 $S_{MIX\ and}$ SARS S.
Figure 6:
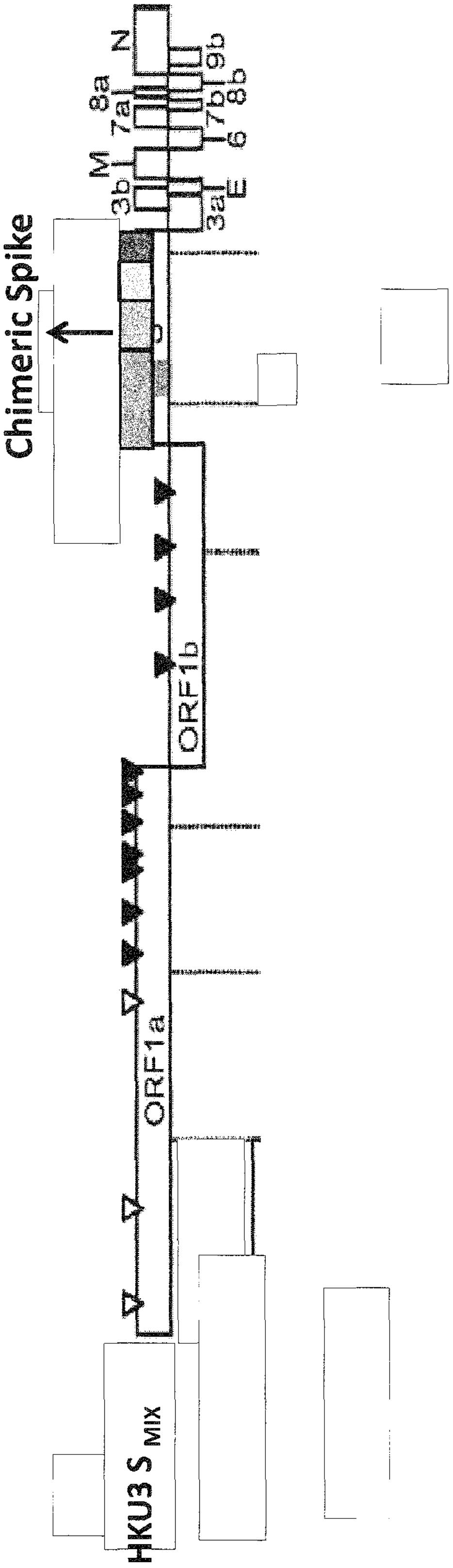
FIG. 6. Schematic of the HKU2 virus with the chimeric antigen HKU 3 $S_{MIX}$. Panel A. The HKU3 virus which has the chimeric antigen HKU 3 $S_{MIX}$ is shown. The open reading frames are indicated. Panel B. Growth curve of HKU 3 virus with the chimeric spike antigen HKU 3 $S_{MIX}$. The HKU3 virus which has the chimeric spike antigen HKU 3 $S_{MIX}$ grows similar to SARS CoV in Vero cells.
Figure 6:
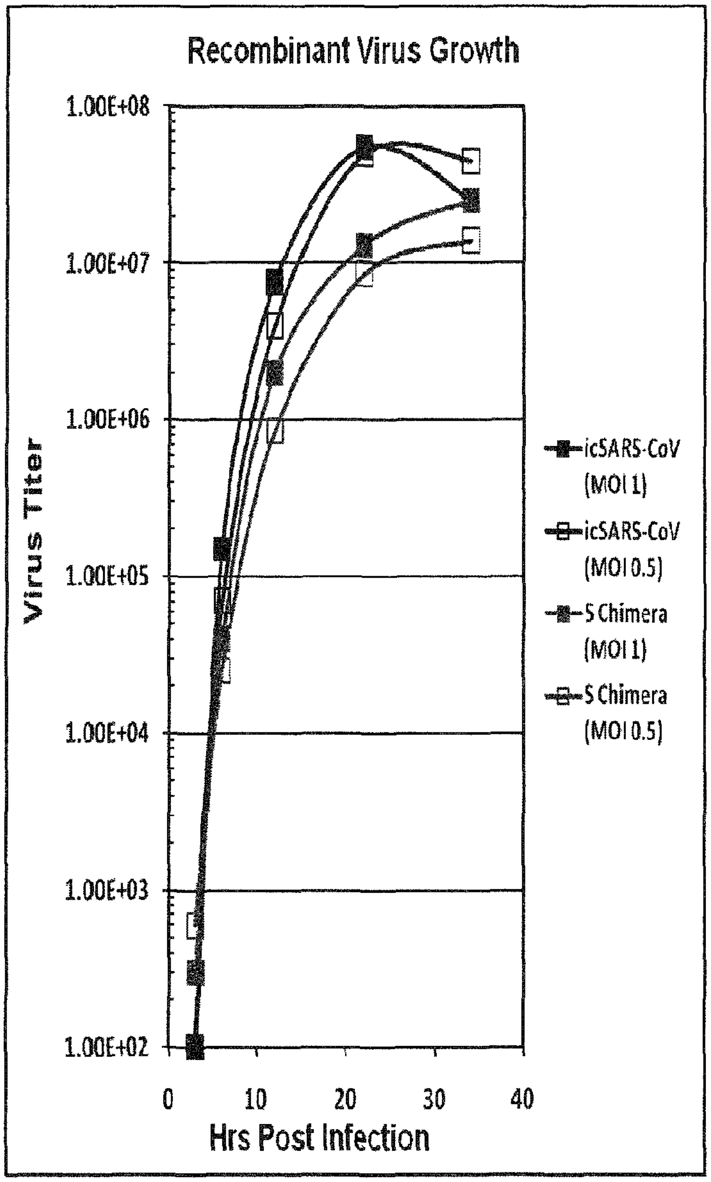
Figure 7:
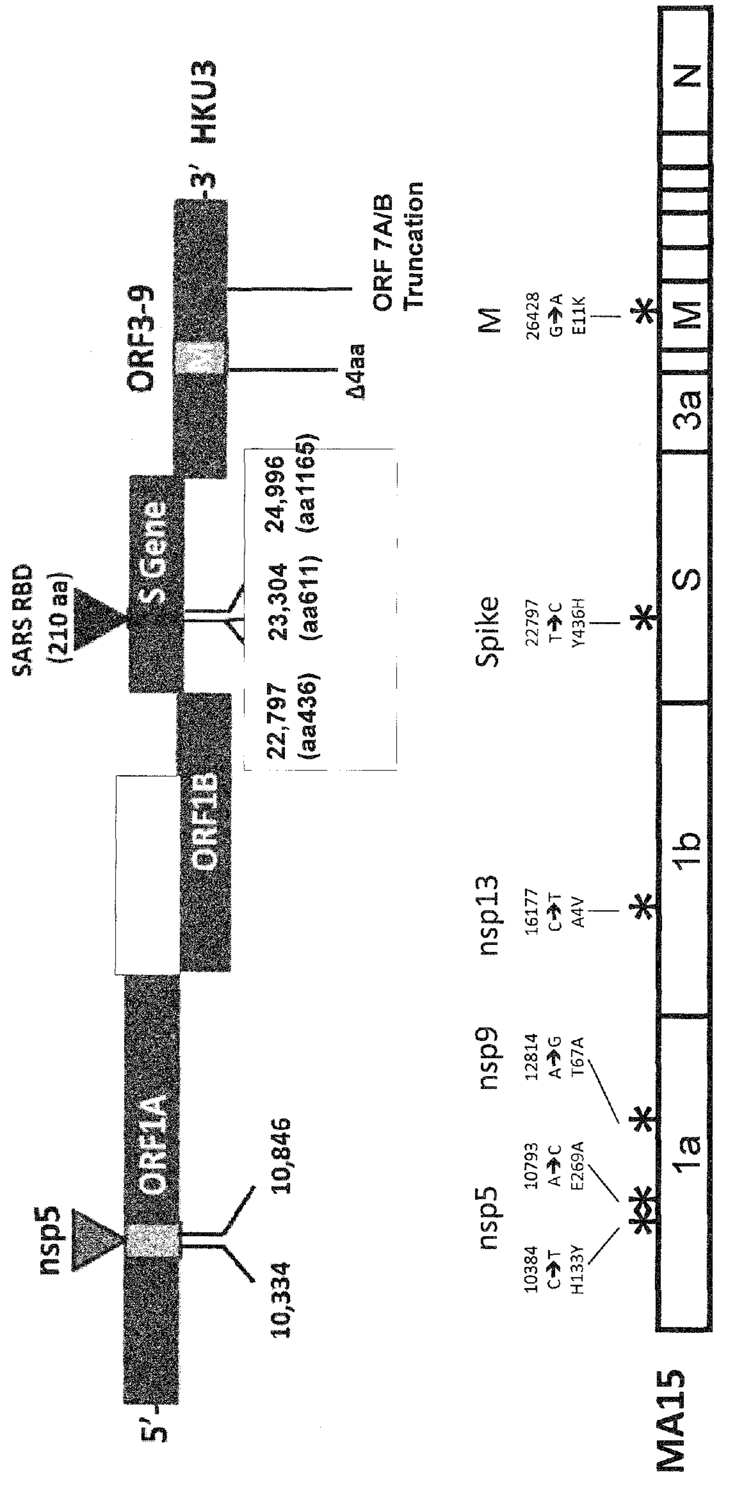
FIG. 7. Schematic of the BAT-SRBDMAv. This virus has the HKU3 backbone, with the spike protein containing a chimera of HKU3 spike and receptor binding domain from SARS-CoV spike 210aa. This virus was created by serial passage of the parent virus in 20 week old Balb/C mice, resulting in virulent phenotype. The amino acid mutations essential for mouse adaptation are indicated and for comparison, the mouse adapted SARS-CoV is shown with the mouse adapted mutations.
Figure 8:
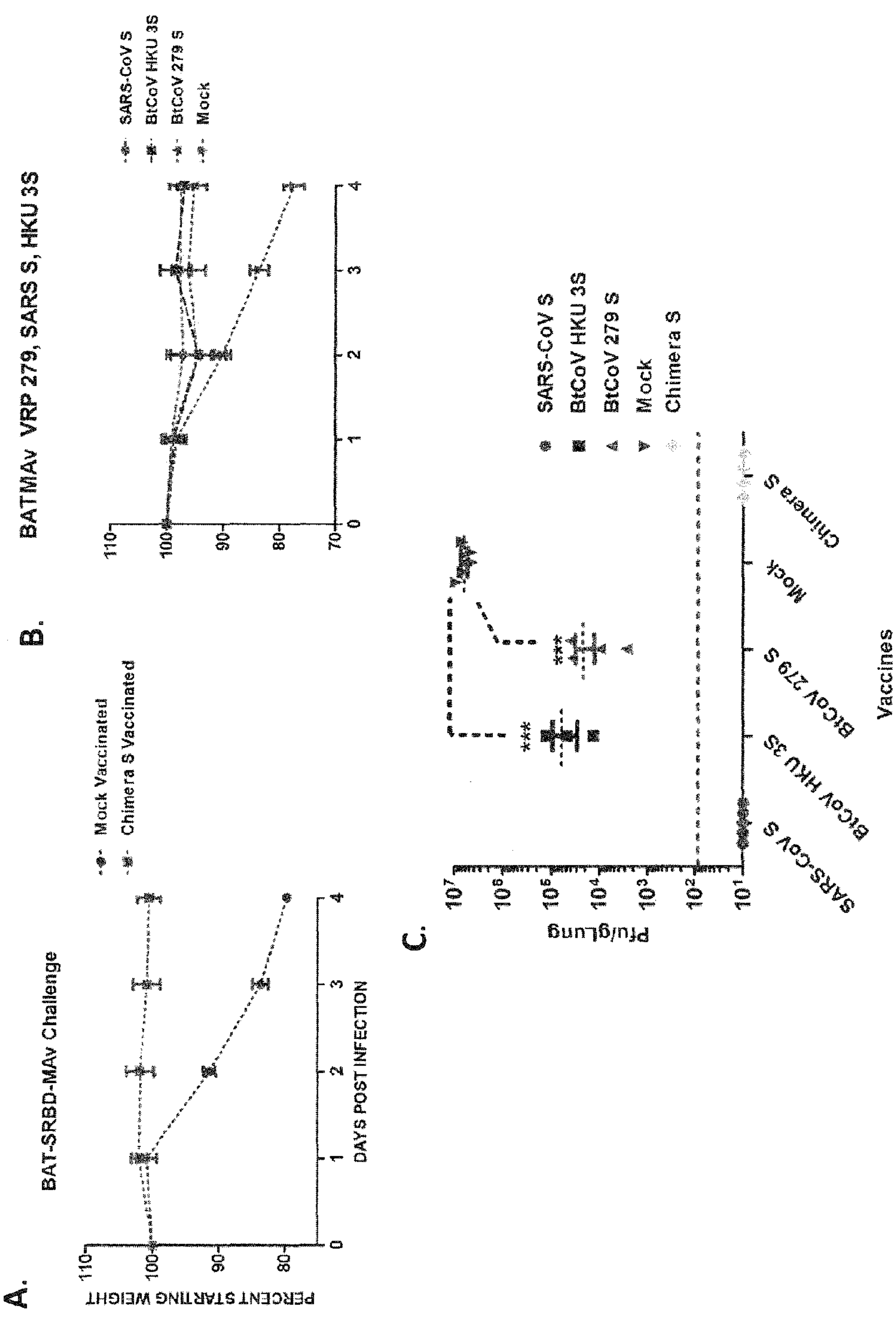
FIG. 8. Chimeric spike antigen HKU 3 S ma protects against lethal challenge with BAT-SRBD-Mav when compared. Panels A and B. Percent weight loss of young Balb/C mice immunized with chimeric antigen HKU 3 S ma, SARS S, BtCoV 279 S, and BtCoV HKU S and challenged with lethal dose of heterologous mouse adapted BAT-SRBD-MAv. Mice immunized with chimeric antigen, SARS S show no weight loss, whereas there is about 3-5% weight loss with HKU3 S and BtCoV 279 S. Panel C. Lung titers on Day 2 post infection of the same groups of mice shown above. Viral replication is reduced on D2 in BtCoV 279 S and HKU3 S group, but no virus is detected in groups of mice vaccinated with HKU 3 $S_{MIX\ and}$ SARS S.
Figure 9:
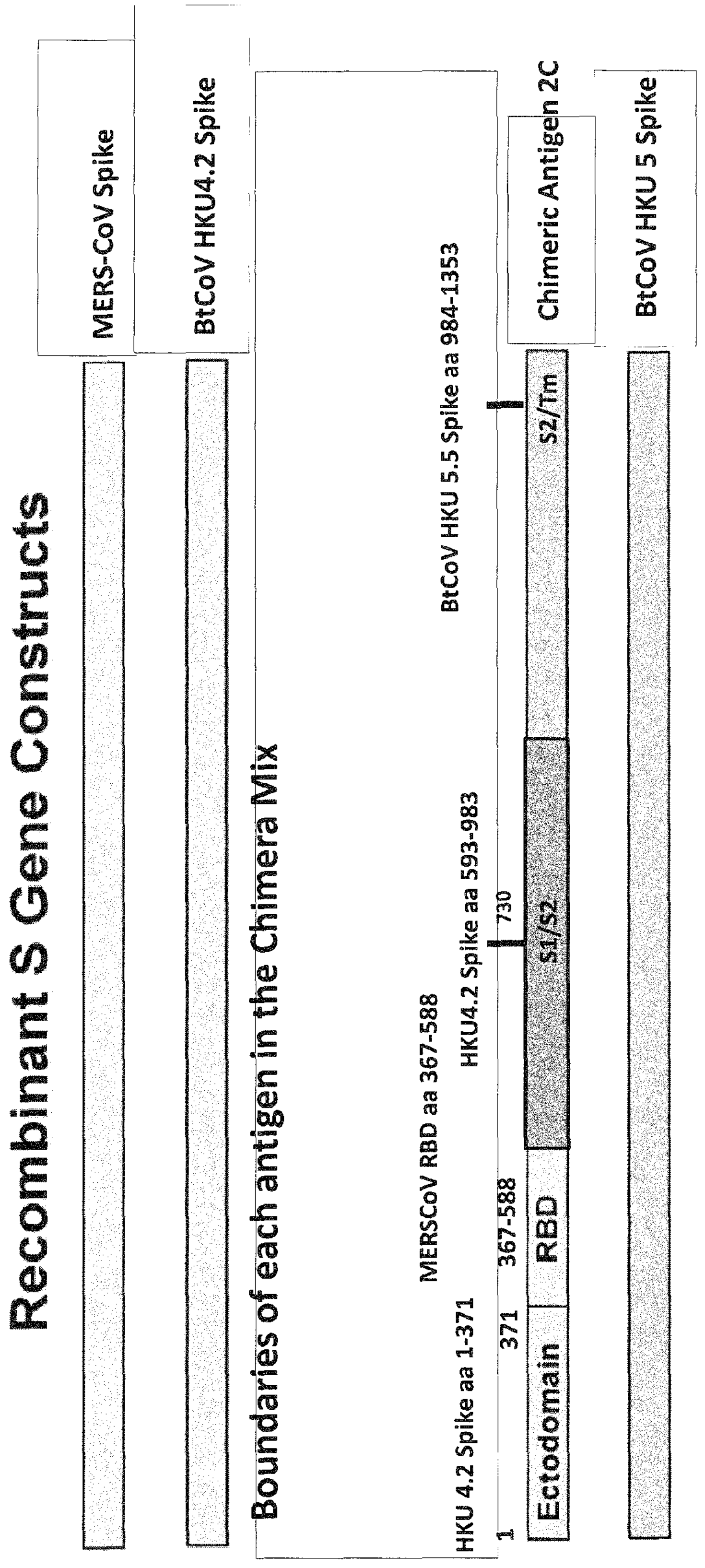
FIG. 9. Design of the chimeric spike antigen for subgroup 2c. The chimeric spike antigen 2c has components from HKU4.2 S, MERS-CoV S RBD, and BtCoV 5.5S. The specific amino acid residues adopted from each of the spike proteins are indicated. S1/S2 boundary is indicated (730aa). S2/Tm domain is indicated (~1190aa).
Figure 10:
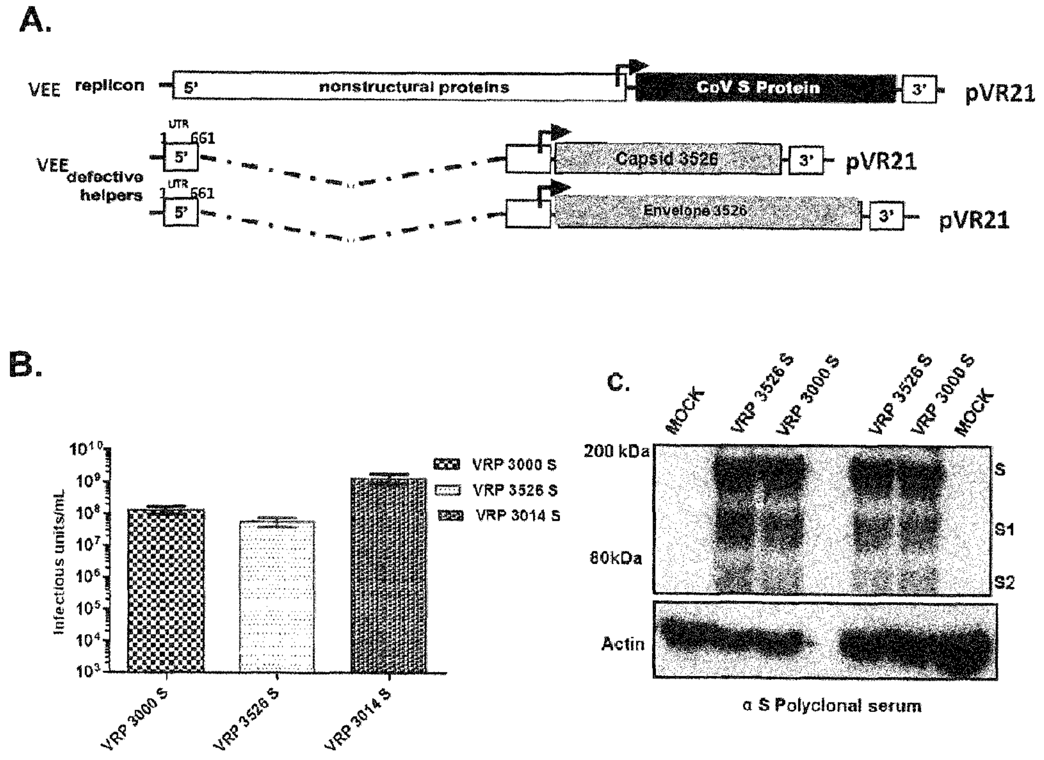
FIG. 10. Characterization of VRP 3526 Platform. Panel A. VEE 3526 replicon CoV S protein expression construct. The capsid and E glycoprotein genes from Venezuelan equine encephalitis virus are replaced with the Coronavirus Spike Protein gene S. The VEE capsid and E glycoproteins are supplied in separate constructs. When cells are transfected with all three constructs, VEE replicons encoding CoV S are formed. Panel B. Titers of S protein vaccines from all three different coats determined on BHK cells by an IFA assay.

Representative nonlimiting examples of a chimeric coronavirus spike protein of this invention are shown in FIGS. 2 and 9, each of which show a schematic of a subgroup b coronavirus spike protein and a subgroup c coronavirus spike protein, respectively with the regions described above shown in their locations in a nonchimeric (e.g., wild type) coronavirus spike protein.

The chimeric coronavirus spike protein of this invention can be produced by combining domains or portions of coronavirus spike proteins as described above from subgroup 1a coronaviruses, subgroup 1b coronaviruses, subgroup 2a coronaviruses, subgroup 2b coronaviruses, subgroup 2c coronaviruses, or subgroup 2d coronaviruses. As one nonlimiting example, the present invention provides a chimeric subgroup 2b coronavirus spike protein comprising, in orientation from amino to carboxy terminus: a) a first region comprising amino acids 1-325 of a spike protein of a first subgroup 2b coronavirus; b) a second region comprising amino acids 322-500 of a spike protein of a second subgroup 2b coronavirus; c) a third region comprising amino acids 488-842 of a spike protein of said first subgroup 2b coronavirus; and) a fourth region comprising amino acids 842-1241 of a spike protein of a third subgroup 2b coronavirus. The amino acid sequence of the chimeric coronavirus spike protein of this example is shown below, with these four regions identified (first and third regions from said first subgroup 2b coronavirus shown in bold; second region from said second subgroup 2b coronavirus shown with underline; and fourth region from said third subgroup 2b coronavirus shown in italics).

(SEQ ID NO: 1)

1 MKILIFAFLA NLAKAQEGCG IISRKPQPKM AQVSSSRRGV YYNDDIFRSD VLHLTQDYFL

61 PFDSNLTQYF SLNVDSDRYT YFDNPILDFG DGVYFAATEK SNVIRGWIFG SSFDNTTQSA

121 VIVNNSTHII IRVCNFNLCK EPMYTVSRGT QQNAWVYQSA FNCTYDRVEK SFQLDTTPKT

181 GNFKDLREYV FKNRDGFLSV YQTYTAVNLP RGLPTGFSVL KPILKLPFGI NITSYRVVMA

241 MFSQTTSNFL PESAAYYVGN LKYSTFMLRF NENGTITDAV DCSQNPLAEL KCTIKNFNVD

301 KGIYQTSNFR VSPTQEVIRF PNITNLCPFG EVFNATKFPS VYAWERKKIS NCVADYSVLY

361 NSTFFSTFKC YGVSATKLND LCFSNVYADS FVVKGDDVRQ IAPGQTGVIA DYNYKLPDDF

421 MGCVLAWNTR NIDATSTGNY NYKYRYLRHG KLRPFERDIS NVPFSPDGKP CTPPALNCYW

481 PLNDYGFYTT TGIGYQPYRV VVLSFELLNA PATVCGPKLS TDLVKNQCVN FNFNGLKGTG

541 VITSSSKRFQ SFQQFGRDTS DFTDSVRDPQ TLEILDISPC SFGGVSVITP GTNASSEVAV

601 LYQDVNCTDV PTAIRADQLT PAWRVYSTGV NVFQTQAGCL IGAEHVNASY ECDIPIGAGI

661 CASYHTASVL RSTGQKSIVA YTMSLGAENS IAYANNSIAI PTNFSISVTT EVMPVSMAKT

721 AVDCTMYICG DSLECSNLLL QYGSFCTQLN RALTGIAIEQ DKNTQEVFAQ VKQMYKTPAI

781 KDFGGFNFSQ ILPDPSKPTK RSFIEDLLFN KVTLADAGFM KQYGDCLGDV SARDLICAQK

841 FNGLTVLPPL LTDEMVAAY*T AALVSGTATA GWTFGAGSAL QIPFAMQMAY RFNGIGVTQN*

901 *VLYENQKQIA NQFNKAISQI QESLTTTSTA LGKLQDVVND NAQALNTLVK QLSSNFGAIS*

961 *SVLNDILSRL DKVEAEVQID RLITGRLQSL QTYVTQQLIR AAEIRASANL AATKMSECVL*

1021 *GQSKRVDFCG KGYHLMSFPQ AAPHGVVFLH VTYVPSQERN FTTAPAICHE GKAYFPREGV*

1081 *FVSNGTSWFI TQRNFYSPQI ITTDNTFVAG NCDVVIGIIN NTVYDPLQPE LDSFKEELDK*

1141 *YFKNHTSPDV DLGDISGINA SVVNIQKEID RLNEVAKNLN ESLIDLQELG KYEQYIKWPW*

1201 *YVWLGFIAGL IAIVMVTILL CCMTSCCSCL KGACSCGSCC KFDEDDSEPV LKGVKLHYT*

The exemplary chimeric coronavirus spike protein shown above was produced from the following three subgroup 2b coronaviruses:

Bat SARS CoV-HKU3 spike protein (GenBank® Accession No. ACJ60694.1) (first coronavirus) (SEQ ID NO:2)

1 MKILIFAFLA NLAKAQEGCG IISRKPQPKM AQVSSSRRGV YYNDDIFRSD VLHLTQDYFL

61 PFDSNLTQYF SLNVDSDRYT YFDNPILDFG DGVYFAATEK SNVIRGWIFG SSFDNTTQSA

121 VIVNNSTHII IRVCNFNLCK EPMYTVSRGT QQNAWVYQSA FNCTYDRVEK SFQLDTTPKT

181 GNFKDLREYV FKNRDGFLSV YQTYTAVNLP RGLPTGFSVL KPILKLPFGI NITSYRVVMA

241 MFSQTTSNFL PESAAYYVGN LKYSTFMLRF NENGTITDAV DCSQNPLAEL KCTIKNFNVD

301 KGIYQTSNFR VSPTQEVIRF PNITNRCPFD KVFNATRFPN VYAWERTKIS DCVADYTVLY

-continued

361 NSTSFSTFKC YGVSPSKLID LCFTSVYADT FLIRSSEVRQ VAPGETGVIA DYNYKLPDDF

421 TGCVIAWNTA KHDTGNYYYR SHRKTKLKPF ERDLSSDDGN GVYTLSTYDF NPNVPVAYQA

481 TRVVVLSFEL LNAPATVCGP KLSTELVKNQ CVNFNFNGLK GTGVLTSSSK RFQSFQQFGR

541 DTSDFTDSVR DPQTLEILDI SPCSFGGVSV ITPGTNASSE VAVLYQDVNC TDVPTAIRAD

601 QLTPAMRVYS TGVNVFQTQA GCLIGAEHVN ASYECDIPIG AGICASYHTA SVLRSTGQKS

661 IVAYTMSLGA ENSIAYANNS IAIPTNFSIS VTTEVMPVSM AKTAVDCTMY ICGDSLECSN

721 LLLQYGSFCT QLNRALTGIA IEQDKNTQEV FAQVKQMYKT PAIKDFGGFN FSQILPDPSK

781 PTKRSFIEDL LFNKVTLADA GFMKQYGDCL GDVSARDLIC AQKFNGLTVL PPLLTDEMVA

841 AYTAALVSGT ATAGWTFGAG AALQIPFAMQ MAYRFNGIGV TQNVLYENQK LIANQFNSAI

901 GKIQESLSST ASALGKLQDV VNQNAQALNT LVKQLSSNFG AISSVLNDIL SRLDKVEAEV

961 QIDRLITGRL QSLQTYVTQQ LIRAAEIRAS ANLAATKMSE CVLGQSKRVD FCGKGYHLMS

1021 FPQSAPHGVV FLHVTYVPSQ EKNFTTAPAI CHEGKAYFPR EGVFVSNGTS WFITQRNFYS

1081 PQLITTDNTF VSGNCDVVIG IINNTVYDPL QPELDSFKEE LDKYFKNHTS PDVDLGDISG

1141 INASVVNIQK EIDRLNEVAK NLNESLIDLQ ELGKYEQYIK WPWYVWLGFI AGLIAIVMVT

1201 ILLCCMTSCC SCLKGACSCG SCCKFDEDDS EPVLKGVKLH YT

SARS CoV Urbani spike protein (Accession No. AAP13441.1) (second coronavirus) (SEQ ID NO:3)

1 MFIFLLFLTL TSGSDLDRCT TFDDVQAPNY TQHTSSMRGV YYPDEIFRSD TLYLTQDLFL

61 PFYSNVTGFH TINHTFGNPV IPFKDGIYFA ATEKSNVVRG WVFGSTMNNK SQSVIIINNS

121 TNVVIRACNF ELCDNPFFAV SKPMGTQTHT MIFDNAFNCT FEYISDAFSL DVSEKSGNFK

181 HLREFVFKNK DGFLYVYKGY QPIDVVRDLP SGFNTLKPIF KLPLGINITN FRAILTAFSP

241 AQDIWGTSAA AYFVGYLKPT TFMLKYDENG TITDAVDCSQ NPLAELKCSV KSFEIDKGIY

301 QTSNFRVVPS GDVVRFPNIT NLCPFGEVFN ATKFPSVYAW ERKKISNCVA DYSVLYNSTF

361 FSTFKCYGVS ATKLNDLCFS NVYADSFVVK GDDVRQIAPG QTGVIADYNY KLPDDFMGCV

421 LAWNTRNIDA TSTGNYNYKY RYLRHGKLRP FERDISNVPF SPDGKPCTPP ALNCYWPLND

481 YGFYTTTGIG YQPYRVVVLS FELLNAPATV CGPKLSTDLI KNQCVNFNFN GLTGTGVLTP

541 SSKRFQPFQQ FGRDVSDFTD SVRDPKTSEI LDISPCSFGG VSVITPGTNA SSEVAVLYQD

601 VNCTDVSTAI HADQLTPAWR IYSTGNNVFQ TQAGCLIGAE HVDTSYECDI PIGAGICASY

661 HTVSLLRSTS QKSIVAYTMS LGADSSIAYS NNTIAIPTNF SISITTEVMP VSMAKTSVDC

721 NMYICGDSTE CANLLLQYGS FCTQLNRALS GIAAEQDRNT REVFAQVKQM YKTPTLKYFG

781 GFNFSQILPD PLKPTKRSFI EDLLFNKVTL ADAGFMKQYG ECLGDINARD LICAQKFNGL

841 TVLPPLLTDD MIAAYTAALV SGTATAGWTF GAGAALQIPF AMQMAYRFNG IGVTQNVLYE

901 NQKQIANQFN KAISQIQESL TTTSTALGKL QDVVNQNAQA LNTLVKQLSS NFGAISSVLN

961 DILSRLDKVE AEVQIDRLIT GRLQSLQTYV TQQLIRAAEI RASANLAATK MSECVLGQSK

1021 RVDFCGKGYH LMSFPQAAPH GVVFLHVTYV PSQERNFTTA PAICHEGKAY FPREGVFVFN

1081 GTSWFITQRN FFSPQIITTD NTFVSGNCDV VIGIINNTVY DPLQPELDSF KEELDKYFKN

1141 HTSPDVDLGD ISGINASVVN IQKEIDRLNE VAKNLNESLI DLQELGKYEQ YIKWPWYVWL

1201 GFIAGLIAIV MVTILLCCMT SCCSCLKGAC SCGSCCKFDE DDSEPVLKGV KLHYT

Bt SARS CoV 279/2005 spike protein (Accession No. ABG47069) (third coronavirus) (SEQ ID NO:4)

```
   1 MKVLIFALLF SLAKAQEGCG IISRKPQPKM EKVSSSRRGV YYNDDIFRSD VLHLTQDYFL
  61 PFDSNLTQYF SLNIDSNKYT YFDNPILDFG DGVYFAATEK SNVIRGWIFG SSFDNTTQSA
 121 IIVNNSTHII IRVCNFNLCK EPMYTVSKGT QQSSWVYQSA FNCTYDRVEK SFQLDTAPKT
 181 GNFKDLREYV FKNRDGFLSV YQTYTAVNLP RGFPAGFSVL RPILKLPFGI NITSYRVVMT
 241 MFSQFNSNFL PESAAYYVGN LKYTTFMLSF NENGTITDAV DCSQNPLAEL KCTIKNFNVS
 301 KGIYQTSNFR VTPTQEVVRF PNITNRCPFD KVFNASRFPN VYAWERTKIS DCVADYTVLY
 361 NSTSFSTFKC YGVSPSKLID LCFTSVYADT FLIRSSEVRQ VAPGETGVIA DYNYKLPDDF
 421 TGCVIAWNTA QQDQGQYYYR SYRKEKLKPF ERDLSSDENG VYTLSTYDFY PSIPVEYQAT
 481 RVVVLSFELL NAPATVCGPK LSTQLVKNQC VNFNFNGLRG TGVLTTSSKR FQSFQQFGRD
 541 TSDFTDSVRD PQTLEILDIS PCSFGGVSVI TPGTNASSEV AVLYQDVNCT DVPTSIHADQ
 601 LTPAWRVYST GVNVFQTQAG CLIGAEHVNA SYECDIPIGA GICASYHTAS VLRSTGQKSI
 661 VAYTMSLGAE NSIAYANNSI AIPTNFSISV TTEVMPVSIA KTSVDCTMYI CGDSLECSNL
 721 LLQYGSFCTQ LNRALTGIAI EQDKNTQEVF AQVKQMYKTP AIKDFGGFNF SQILPDPSKP
 781 TKRSFIEDLL FNKVTLADAG FMKQYGECLG DISARDLICA QKFNGLTVLP PLLTDEMIAA
 841 YTAALVSGTA TAGWTFGAGS ALQIPFAMQM AYRFNGIGVT QNVLYENQKQ IANQFNKAIS
 901 QIQESLTTTS TALGKLQDVV NDNAQALNTL VKQLSSNFGA ISSVLNDILS RLDEVEAEVQ
 961 IDRLITGRLQ SLQTYVTQQL IRAAEIRASA NLAATKMSEC VLGQSKRVDF CGKGYHLMSF
1021 PQAAPHGVVF LHVTYVPSQE RNFTTAPAIC HEGKAYFPRE GVFVSNGTSW FITQRNFYSP
1081 QIITTDNTFV AGNCDVVIGI INNTVYDPLQ PELDSFKEEL DKYFKNHTSP DVDLGDISGI
1141 NASVVNIQKE IDRLNEVAKN LNESLIDLQE LGKYEQYIKW PWYVWLGFIA GLIAIVMVTI
1201 LLCCMTSCCS CLKGACSCGS CCKFDEDDSE PVLKGVKLHY T
```

It is to be understood that this example is not intended to be limiting and any of these three subgroup 2b coronaviruses can be combined with any other subgroup 2b coronavirus in any combination of first coronavirus, second coronavirus and third coronavirus, provided that they are all different from one another.

Furthermore, the length in amino acid residues of the respective regions of the chimeric subgroup 2b coronavirus spike protein can vary. For example, the first region can comprise amino acid 1 through amino acid 320, amino acid 1 through amino acid 321, amino acid 1 through amino acid 322, amino acid 1 through amino acid 323, amino acid 1 through amino acid 324, amino acid 1 through amino acid 325, amino acid 1 through amino acid 326, amino acid 1 through amino acid 327, amino acid 1 through amino acid 328, amino acid 1 through amino acid 329 or amino acid 1 through amino acid 330 of a subgroup 2b coronavirus spike protein, which is a first coronavirus Amino acid numbering is based on the numbering of amino acid residues in a subgroup 2b coronavirus spike protein, representative examples of which are provided herein.

For the second region of the chimeric subgroup 2b coronavirus spike protein of this invention, the amino end of the second region can begin at amino acid 315, 316, 317, 318, 319, 320, 321, 322, 323, 324, 325, 326, 327, 328, 329 or 330 of a subgroup 2b coronavirus spike protein and be contiguous through amino acid 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524 or 525 of a subgroup 2b coronavirus spike protein of a second coronavirus that is different from the first coronavirus.

For the third region of the chimeric subgroup 2b coronavirus spike protein of this invention, the amino end of the third region can begin at amino acid 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509 or 510 of a subgroup 2b coronavirus spike protein and be contiguous through amino acid 825, 826, 827, 828, 829, 830, 831, 832, 833, 834, 835, 836, 837, 838, 839, 840, 841, 842, 843, 844, 845, 846, 847, 848, 849 or 850 of a subgroup 2b coronavirus spike protein. As noted above, the third region of the chimeric coronavirus spike protein is from the coronavirus that is the first coronavirus.

For the fourth region of the chimeric subgroup 2b coronavirus spike protein of this invention, the amino end of the fourth region can begin at amino acid 825, 826, 827, 828, 829, 830, 831, 832, 833, 834, 835, 836, 837, 838, 839, 840, 841, 843, 844, 845, 846, 847, 848, 849 or 850 of a subgroup 2b coronavirus spike protein and be contiguous through amino acid 1225, 1226, 1227, 1228, 1229, 1230, 1231, 1232, 1233, 1234, 1235, 1236, 1237, 1238, 1240, 1241, 1242 or the final amino acid at the carboxy terminus of a subgroup 2b coronavirus spike protein. As noted above the fourth region of the chimeric coronavirus spike protein is from a third coronavirus that is different from the first coronavirus and the second coronavirus used to produce the chimeric coronavirus spike protein.

As a further nonlimiting example, the present invention provides a chimeric subgroup 2c coronavirus spike protein comprising, in orientation from amino to carboxy terminus: a) a first region comprising amino acids 1-371 of a spike protein of a first subgroup 2c coronavirus; b) a second region comprising amino acids 367-588 of a spike protein of a second subgroup 2c coronavirus; c) a third region comprising amino acids 594-983 of the spike protein of said first subgroup 2c coronavirus; and) a fourth region comprising amino acids 986-1357 of a spike protein of a third subgroup 2c coronavirus. The amino acid sequence of the chimeric coronavirus spike protein of this example is shown below, with these four regions identified (first and third regions from said first subgroup 2c coronavirus shown in bold; second region from said second subgroup 2c coronavirus shown with underline; and fourth region from said third subgroup 2c coronavirus shown in italics).

(SEQ ID NO: 5)

1 MTLLMCLLMS LLIFVRGCDS QFVDMSPASN TSECLESQVD AAAFSKLMWP YPIDPSKVDG

61 IIYPLGRTYS NITLAYTGLF PLQGDLGSQY LYSVSHAVGH DGDPTKAYIS NYSLLVNDFD

121 NGFVVRIGAA ANSTGTIVIS PSVNTKIKKA YPAFILGSSL TNTSAGQPLY ANYSLTIIPD

181 GCGTVLHAFY CILKPRTVNR CPSGTGYVSY FIYETVHNDC QSTINRNASL NSFKSFFDLV

241 NCTFFNSWDI TADETKEWFG ITQDTQGVHL YSSRKGDLYG GNMFRFATLP VYEGIKYYTV

301 IPRSFRSKAN KREAWAAFYV YKLHQLTYLL DFSVDGYIRR AIDCGHDDLS QLHCSYTSFE

361 VDTGVYSVSS YEAKPSGSVV EQAEGVECDF SPLLSGTPPQ VYNFKRLVFT NCNYNLTKLL

421 SLFSVNDFTC SQISPAAIAS NCYSSLILDY FSYPLSMKSD LSVSSAGPIS QFNYKQSFSN

481 PTCLILATVP HNLTTITKPL KYSYINKCSR LLSDDRTEVP QLVNANQYSP CVSIVPSTVW

541 EDGDYYRKQL SPLEGGGWLV ASGSTVAMTE QLQMGFGITV QYGTDTNSVC PKLDLGDSLT

601 ITNRLGKCVD YSLYGVTGRG VFQNCTAVGV KQQRFVYDSF DNLVGYYSDD GNYYCVRPCV

661 SVPVSVIYDK STNLHATLFG SVACEHVTTM MSQFSRLTQS NLRRRDSNIP LQTAVGCVIG

721 LSNNSLVVSD CKLPLGQSLC AVPPVSTFRS YSASQFQLAV LNYTSPIVVT PINSSGFTAA

781 IPTNFSFSVT QEYIETSIQK VTVDCKQYVC NGFTRCEKLL VEYGQFCSKI NQALHGANLR

841 QDESVYSLYS NIKTTSTQTL EYGLNGDFNL TLLQVPQIGG SSSSYRSAIE DLLFDKVTIA

901 DPGYMQGYDD CMKQGPQSAR DLICAQYVSG YKVLPPLYDP NMEAAYTSSL LGSIAGAGWT

961 AGLSSFAAIP FAQSMFYRLN GVG*ITQQVLS ENQKIIANKF NQALGAMQTG FTTTNLAFNK*

1021 *VQDAVNANAM ALSKLAAELS NTFGAISSSI SDILARLDTV EQEAQIDRLI NGRLTSLNAF*

1081 *VAQQLVRTEA AARSAQLAQD KVNECVKSQS KRNGFCGTGT HIVSFAINAP NGLYFFHVGY*

1141 *QPTSHVNATA AYGLCNTENP PKCIAPIDGY FVLNQTTSTA RSSGDQHWYY TGSSFFHPEP*

1201 *ITEANSKYVS MDVKFENLTN KLPPPLLSNS TDLDFKDELE EFFKNVSSQG PNFQEISKIN*

1261 *TTLLNLNTEL MVLSEVVKQL NESYIDLKEL GNYTFYQKWP WYIWLGFIAG LVALALCVFF*

1321 *ILCCTGCGTS CLGKLKCNRC CDSYDEYEVE KIHVH*

The exemplary chimeric coronavirus spike protein shown above was produced from the following three subgroup 2c coronaviruses:

Bat CoV HKU4-2 spike protein (Accession No. ABN10848.1) (SEQ ID NO:6)

1 MTLLMCLLMS LLIFVRGCDS QFVDMSPASN TSECLESQVD AAAFSKLMWP YPIDPSKVDG

61 IIYPLGRTYS NITLAYTGLF PLQGDLGSQY LYSVSHAVGH DGDPTKAYIS NYSLLVNDFD

121 NGFVVRIGAA ANSTGTIVIS PSVNTKIKKA YPAFILGSSL TNTSAGQPLY ANYSLTIIPD

181 GCGTVLHAFY CILKPRTVNR CPSGTGYVSY FIYETVHNDC QSTINRNASL NSFKSFFDLV

241 NCTFFNSWDI TADETKEWFG ITQDTQGVHL YSSRKGDLYG GNMFRFATLP VYEGIKYYTV

301 IPRSFRSKAN KREAWAAFYV YKLHQLTYLL DFSVDGYIRR AIDCGHDDLS QLHCSYTSFE

361 VDTGVYSVSS YEASATGTFI EQPNATECDF SPMLTGVAPQ VYNFKRLVFS NCNYNLTKLL

-continued

421 SLFAVDEFSC NGISPDAIAR GCYSTLTVDY FAYPLSMKSY IRPGSAGNIP LYNYKQSFAN

481 PTCRVMASVL ANVTITKPHA YGYISKCSRL TGANQDVETP LYINPGEYSI CRDFSPGGFS

541 EDGQVFKRTL TQFEGGGLLI GVGTRVPMTD NLQMSFIISV QYGTGTDSVC PMLDLGDSLT

601 ITNRLGKCVD YSLYGVTGRG VFQNCTAVGV KQQRFVYDSF DNLVGYYSDD GNYYCVRPCV

661 SVPVSVIYDK STNLHATLFG SVACEHVTTM MSQFSRLTQS NLRRRDSNIP LQTAVGCVIG

721 LSNNSLVVSD CKLPLGQSLC AVPPVSTFRS YSASQFQLAV LNYTSPIVVT PINSSGFTAA

781 IPTNFSFSVT QEYIETSIQK VTVDCKQYVC NGFTRCEKLL VEYGQFCSKI NQALHGANLR

841 QDESVYSLYS NIKTTSTQTL EYGLNGDFNL TLLQVPQIGG SSSSYRSAIE DLLFDKVTIA

901 DPGYMQGYDD CMKQGPQSAR DLICAQYVSG YKVLPPLYDP NMEAAYTSSL LGSIAGAGWT

961 AGLSSFAAIP FAQSMFYRLN GVGITQQVLS ENQKLIANKF NQALGAMQTG FTTSNLAFSK

1021 VQDAVNANAQ ALSKLASELS NTFGAISSSI SDILARLDTV EQDAQIDRLI NGRLTSLNAF

1081 VSQQLVRSET AARSAQLASD KVNECVKSQS KRNGFCGSGT HIVSFVVNAP NGFYFFHVGY

1141 VPTNYTNVTA AYGLCNNNNP PLCIAPIDGY FITNQTTTYS VDTEWYYTGS SFYKPEPITQ

1201 ANSRYVSSDV KFDKLENNLP PPLLENSTDV DFKDELEEFF KNVTSHGPNF AEISKINTTL

1261 LDLSDEMAML QEVVKQLNDS YIDLKELGNY TYYNKWPWYV WLGFIAGLVA LLLCVFFLLC

1321 CTGCGTSCLG KMKCKNCCDS YEEYDVEKIH VH

MERS-CoV spike protein (GenBank Accession No. AFS88936.1) (SEQ ID NO:7)

1 MIHSVFLLMF LLTPTESYVD VGPDSVKSAC IEVDIQQTFF DKTWPRPIDV SKADGIIYPQ

61 GRTYSNITIT YQGLFPYQGD HGDMYVYSAG HATGTTPQKL FVANYSQDVK QFANGFVVRI

121 GAAANSTGTV IISPSTSATI RKIYPAFMLG SSVGNFSDGK MGRFFNHTLV LLPDGCGTLL

181 RAFYCILEPR SGNHCPAGNS YTSFATYHTP ATDCSDGNYN RNASLNSFKE YFNLRNCTFM

241 YTYNITEDEI LEWFGITQTA QGVHLFSSRY VDLYGGNMFQ FATLPVYDTI KYYSIIPHSI

301 RSIQSDRKAW AAFYVYKLQP LTFLLDFSVD GYIRRAIDCG FNDLSQLHCS YESFDVESGV

361 YSVSSFEAKP SGSVVEQAEG VECDFSPLLS GTPPQVYNFK RLVFTNCNYN LTKLLSLFSV

421 NDFTCSQISP AAIASNCYSS LILDYFSYPL SMKSDLSVSS AGPISQFNYK QSFSNPTCLI

481 LATVPHNLTT ITKPLKYSYI NKCSRLLSDD RTEVPQLVNA NQYSPCVSIV PSTVWEDGDY

541 YRKQLSPLEG GGWLVASGST VAMMEQLQMG FGITVQYGTD TNSVCPKLEF ANDTKIASQL

601 GNCVEYSLYG VSGRGVFQNC TAVGVRQQRF VYDAYQNLVG YYSDDGNYYC LRACVSVPVS

661 VIYDKETKTH ATLFGSVACE HISSTMSQYS RSTRSMLKRR DSTYGPLQTP VGCVLGLVNS

721 SLFVEDCKLP LGQSLCALPD TPSTLTPRSV RSVPGEMRLA SIAFNHPIQV DQLNSSYFKL

781 SIPTNFSFGV TQEYIQTTIQ KVTVDCKQYV CNGFQKCEQL LREYGQFCSK INQALHGANL

841 RQDDSVRNLF ASVKSSQSSP IIPGFGGDFN LTLLEPVSIS TGSRSARSAI EDLLFDKVTI

901 ADPGYMQGYD DCMQQGPASA RDLICAQYVA GYKVLPPLMD VNMEAAYTSS LLGSIAGVGW

961 TAGLSSFAAI PFAQSIFYRL NGVGITQQVL SENQKLIANK FNQALGAMQT GFTTTNEAFQ

1021 KVQDAVNNNA QALSKLASEL SNTFGAISAS IGDIIQRLDV LEQDAQIDRL INGRLTTLNA

1081 FVAQQLVRSE SAALSAQLAK DKVNECVKAQ SKRSGFCGQG THIVSFVVNA PNGLYFMHVG

1141 YYPSNHIEVV SAYGLCDAAN PTNCIAPVNG YFIKTNNTRI VDEWSYTGSS FYAPEPITSL

1201 NTKYVAPQVT YQNISTNLPP PLLGNSTGID FQDELDEFFK NVSTSIPNFG SLTQINTTLL

-continued

1261 DLTYEMLSLQ QVVKALNESY IDLKELGNYT YYNKWPWYIW LGFIAGLVAL ALCVFFILCC

1321 TGCGTNCMGK LKCNRCCDRY EEYDLEPHKV HVH

Bat CoV HKU5-5 spike protein (GenBank Accession No. ABN10902.1) (SEQ ID NO:8)

1 MIRSVLVLMC SLTFIGNRTS CQSVDIGTPV TGSCLRSQVR PEYFDIVHNT WPMPIDTSKA

61 EGVIYPNGKS YSNISLTYTG LYPKAKDLGK QYLFSDGHSA PNQLNDLFVS NYSAQVESFD

121 DGFVVRIGAA SNKTGTTVIS QTTFKPIKKI YPGFMLGHAV GNYTPTNITG RYLNHTLVIL

181 PDGCGTLVHA FYCILQPRTQ ANCPGASSFT SVTLWDTPAT DCAPSGVYNS LANLNAFKLY

241 FDLINCTFRY NYTITEDENA EWFGITQDTQ GVHLYSSRKE NVFRNNMFHF ATLPVYQKIL

301 YYTVIPRSIR SPFNDRKAWA AFYIYKLHPL TYLLNFDVEG YITKAVDCGY DDFAQLQCSY

361 ENFDVETGVY SVSSFEASPR GEFIEQATTQ ECDFTPMLTG TPPPIYDFKR LVFTNCNYNL

421 TKLLSLFQVS EFSCHQVSPS SLATGCYSSL TVDYFAYSTD MSSYLQPGSA GEIVQFNYKQ

481 DFSNPTCRVL ATVPTNLTTI TKSSNYVHLT ECYKSTAYGK NYLYNAPGGY TPCLSLASRG

541 FTTNRQSHSL ELPDGYLVTT GSVYPVNGNL QMAFIISVQY GTDTNSVCPM QALRNDTSIE

601 DKLDVCVEYS LHGITGRGVF HNCTSVGLRN QRFVYDTFDN LVGYHSDNGN YYCVRPCVSV

661 PVSVIYDKAS NSHATLFGSV ACSHVTTMMS QFSRMTKTNL PARTTPGPLQ TTVGCAMGFI

721 NSSMVVDECQ LPLGQSLCAI PPTTSTRFRR ATSIPDVFQI ATLNFTSPLT LAPINSTGFV

781 VAVPTNFTFG VTQEFIETTI QKITVDCKQY VCNGFKKCED LLKEYGQFCS KINQALHGAN

841 LRQDESIANL FSSIKTQNTQ PLQAGLNGDF NLTMLQIPQV TTGERKYRST IEDLLFNKVT

901 IADPGYMQGY DECMQQGPQS ARDLICAQYV AGYKVLPPLY DPYMEAAYTS SLLGSIAGAS

961 WTAGLSSFAA IPFAQSIFYR LNGVGITQQV LSENQKIIAN KFNQALGAMQ TGFTTTNLAF

1021 NKVQDAVNAN AMALSKLAAE LSNTFGAISS SISDILARLD TVEQEAQIDR LINGRLTSLN

1081 AFVAQQLVRT EAAARSAQLA QDKVNECVKS QSKRNGFCGT GTHIVSFAIN APNGLYFFHV

1141 GYQPTSHVNA TAAYGLCNTE NPPKCIAPID GYFVLNQTTS TARSSGDQHW YYTGSSFFHP

1201 EPITEANSKY VSMDVEEENL TNKLPPPLLS NSTDLDFKDE LEEFFKNVSS QGPNFQEISK

1261 INTTLLNLNT ELMVLSEVVK QLNESYIDLK ELGNYTFYQK WPWYIWLGFI AGLVALALCV

1321 FFILCCTGCG TSCLGKLKCN RCCDSYDEYE VEKIHVH

It is to be understood that this example is not intended to be limiting and any of these three subgroup 2c coronaviruses can be combined with any other subgroup 2c coronavirus in any combination of first coronavirus, second coronavirus and third coronavirus, provided that they are all different from one another.

Furthermore, the length in amino acid residues of the respective regions of the chimeric subgroup 2c coronavirus spike protein can vary. For example, the first region can comprise amino acid 1 through amino acid 365, amino acid 1 through amino acid 366, amino acid 1 through amino acid 367, amino acid 1 through amino acid 368, amino acid 1 through amino acid 369, amino acid 1 through amino acid 370, amino acid 1 through amino acid 371, amino acid 1 through amino acid 372, amino acid 1 through amino acid 373, amino acid 1 through amino acid 374 or amino acid 1 through amino acid 375 of a subgroup 2c coronavirus spike protein, which is a first coronavirus Amino acid numbering is based on the numbering of amino acid residues in a subgroup 2c coronavirus spike protein, representative examples of which are provided herein.

For the second region of the chimeric subgroup 2c coronavirus spike protein of this invention, the amino end of the second region can begin at amino acid 350, 351, 352, 353, 354, 355, 356, 357, 358, 359, 360, 361, 362, 363, 364, 365, 366, 367, 368, 369, 370, 371, 372, 373, 374 or 375 of a subgroup 2c coronavirus spike protein and be contiguous through amino acid 575, 576, 577, 578, 579, 580, 581, 582, 583, 584, 585, 586, 587, 588, 589, 590, 591, 592, 593, 594, 595, 596, 597, 598, 599 or 600 of a subgroup 2c coronavirus spike protein of a second coronavirus that is different from the first coronavirus.

For the third region of the chimeric subgroup 2c coronavirus spike protein of this invention, the amino end of the third region can begin at amino acid 580, 581, 582, 583, 584, 585, 586, 587, 588, 589, 590, 591, 592, 593, 594, 595, 596, 597, 598, 599 or 600 of a subgroup 2c coronavirus spike protein and be contiguous through amino acid 975, 976, 977, 978, 979, 980, 981, 982, 983, 984, 985, 986, 987, 988, 989, 990, 991, 992, 993, 994, 995, 996, 997, 998, 999 or 1000 of a subgroup 2c coronavirus spike protein. As noted above, the third region of the chimeric coronavirus spike protein is from the subgroup 2c coronavirus that is the first coronavirus.

For the fourth region of the chimeric subgroup 2c coronavirus spike protein of this invention, the amino end of the fourth region can begin at amino acid 975, 976, 977, 978, 979, 980, 981, 982, 983, 984, 985, 986, 987, 988, 989, 990, 991, 992, 993, 994, 995, 996, 997, 998, 999 or 1000 of a subgroup 2c coronavirus spike protein and be contiguous through amino acid 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370 or the final amino acid at the carboxy terminus of a subgroup 2c coronavirus spike protein. As noted above the fourth region of the chimeric coronavirus spike protein is from a third subgroup 2c coronavirus that is different from the first subgroup 2c coronavirus and the second subgroup 2c coronavirus used to produce this chimeric coronavirus spike protein.

Although the examples set forth above describe a chimeric spike protein produced from subgroup 2b coronaviruses and a chimeric spike protein produced from subgroup 2c coronaviruses, it is to be understood that a chimeric coronavirus spike protein of this invention can be made from any combination of three different coronaviruses from any subgroup, including subgroup 1a, subgroup 1b, subgroup 2a, subgroup 2d and subgroup 3 in addition to subgroup 2b and subgroup 2c. The same arrangement of the first, second, third and fourth regions as described above would be applicable to a chimeric coronavirus spike protein of any subgroup and the same variability with regard to the amino acids that define the beginning and end of each of these four regions would be applicable to a chimeric coronavirus spike protein of any subgroup.

Furthermore, the chimeric coronavirus spike proteins produced from the respective coronavirus subgroups 1a, 1b, 2a, 2b, 2c, 2d and 3 can be included in the methods and compositions of this invention in any combination and/or in any ratio relative to one another, as would be well understood to one of ordinary skill in the art.

Nonlimiting examples of subgroup 2b coronaviruses that can be used to produce the chimeric coronavirus spike protein of this invention include Bat SARS CoV (GenBank Accession No. FJ211859), SARS CoV (GenBank Accession No. FJ211860), BtSARS.HKU3.1 (GenBank Accession No. DQ022305), BtSARS.HKU3.2 (GenBank Accession No. DQ084199), BtSARS.HKU3.3 (GenBank Accession No. DQ084200), BtSARS.Rm1 (GenBank Accession No. DQ412043), BtCoV.279.2005 (GenBank Accession No. DQ648857), BtSARS.Rf1 (GenBank Accession No. DQ412042), BtCoV.273.2005 (GenBank Accession No. DQ648856), BtSARS.Rp3 (GenBank Accession No. DQ071615), SARS CoV.A022 (GenBank Accession No. AY686863), SARSCoV.CUHK-W1 (GenBank Accession No. AY278554), SARSCoV.GDO1 (GenBank Accession No. AY278489), SARSCoV.HC.SZ.61.03 (GenBank Accession No. AY515512), SARSCoV.SZ16 (GenBank Accession No. AY304488), SARSCoV.Urbani (GenBank Accession No. AY278741), SARSCoV.civet010 (GenBank Accession No. AY572035), and SARSCoV.MA.15 (GenBank Accession No. DQ497008), Rs SHC014 (GenBank® Accession No. KC881005), Rs3367 (GenBank® Accession No. KC881006), WiV1 S (GenBank® Accession No. KC881007) as well as any other subgroup 2b coronavirus now known (e.g., as can be found in the GenBank® Database) or later identified, and any combination thereof.

Nonlimiting examples of subgroup 2c coronaviruses that can be used to produce the chimeric coronavirus capsid protein of this invention include: Middle East respiratory syndrome coronavirus isolate Riyadh_2_2012 (GenBank Accession No. KF600652.1), Middle East respiratory syndrome coronavirus isolate Al-Hasa_18_2013 (GenBank Accession No. KF600651.1), Middle East respiratory syndrome coronavirus isolate Al-Hasa_17_2013 (GenBank Accession No. KF600647.1), Middle East respiratory syndrome coronavirus isolate Al-Hasa_15_2013 (GenBank Accession No. KF600645.1), Middle East respiratory syndrome coronavirus isolate Al-Hasa_16_2013 (GenBank Accession No. KF600644.1), Middle East respiratory syndrome coronavirus isolate Al-Hasa_21_2013 (GenBank Accession No. KF600634), Middle East respiratory syndrome coronavirus isolate Al-Hasa_19_2013 (GenBank Accession No. KF600632), Middle East respiratory syndrome coronavirus isolate Buraidah_1_2013 (GenBank Accession No. KF600630.1), Middle East respiratory syndrome coronavirus isolate Hafr-Al-Batin_1_2013 (GenBank Accession No. KF600628.1), Middle East respiratory syndrome coronavirus isolate Al-Hasa_12_2013 (GenBank Accession No. KF600627.1), Middle East respiratory syndrome coronavirus isolate Bisha_1_2012 (GenBank Accession No. KF600620.1), Middle East respiratory syndrome coronavirus isolate Riyadh_3_2013 (GenBank Accession No. KF600613.1), Middle East respiratory syndrome coronavirus isolate Riyadh_1_2012 (GenBank Accession No. KF600612.1), Middle East respiratory syndrome coronavirus isolate Al-Hasa_3_2013 (GenBank Accession No. KF186565.1), Middle East respiratory syndrome coronavirus isolate Al-Hasa_1_2013 (GenBank Accession No. KF186567.1), Middle East respiratory syndrome coronavirus isolate Al-Hasa_2_2013 (GenBank Accession No. KF186566.1), Middle East respiratory syndrome coronavirus isolate Al-Hasa_4_2013 (GenBank Accession No. KF186564.1), Middle East respiratory syndrome coronavirus (GenBank Accession No. KF192507.1), Betacoronavirus England 1-N1 (GenBank Accession No. NC_019843), MERS-CoV_SA-N1 (GenBank Accession No. KC667074), following isolates of Middle East Respiratory Syndrome Coronavirus (GenBank Accession No: KF600656.1, GenBank Accession No: KF600655.1, GenBank Accession No: KF600654.1, GenBank Accession No: KF600649.1, GenBank Accession No: KF600648.1, GenBank Accession No: KF600646.1, GenBank Accession No: KF600643.1, GenBank Accession No: KF600642.1, GenBank Accession No: KF600640.1, GenBank Accession No: KF600639.1, GenBank Accession No: KF600638.1, GenBank Accession No: KF600637.1, GenBank Accession No: KF600636.1, GenBank Accession No: KF600635.1, GenBank Accession No: KF600631.1, GenBank Accession No: KF600626.1, GenBank Accession No: KF600625.1, GenBank Accession No: KF600624.1, GenBank Accession No: KF600623.1, GenBank Accession No: KF600622.1, GenBank Accession No: KF600621.1, GenBank Accession No: KF600619.1, GenBank Accession No: KF600618.1, GenBank Accession No: KF600616.1, GenBank Accession No: KF600615.1, GenBank Accession No: KF600614.1, GenBank Accession No: KF600641.1, GenBank Accession No: KF600633.1, GenBank Accession No: KF600629.1, GenBank Accession No: KF600617.1), Coronavirus Neoromicia/PML-PHE1/RSA/2011 GenBank Accession: KC869678.2, Bat Coronavirus Taper/CII_KSA_287/Bisha/Saudi Arabia/GenBank Accession No: KF493885.1, Bat coronavirus Rhhar/CII_KSA_003/Bisha/Saudi Arabia/2013 GenBank Accession No: KF493888.1, Bat coronavirus Pikuh/CII_KSA_001/Riyadh/Saudi Arabia/2013 GenBank Accession No: KF493887.1, Bat coronavirus Rhhar/CII_KSA_002/Bisha/Saudi Arabia/2013 GenBank Accession No: KF493886.1, Bat Coronavirus Rhhar/

CII_KSA_004/Bisha/Saudi Arabia/2013 GenBank Accession No: KF493884.1, BtCoV.HKU4.2 (GenBank Accession No. EF065506), BtCoV.HKU4.1 (GenBank Accession No. NC_009019), BtCoV.HKU4.3 (GenBank Accession No. EF065507), BtCoV.HKU4.4 (GenBank Accession No. EF065508), BtCoV 133.2005 (GenBank Accession No. NC 008315), BtCoV.HKU5.5 (GenBank Accession No. EF065512); BtCoV.HKU5.1 (GenBank Accession No. NC_009020), BtCoV.HKU5.2 (GenBank Accession No. EF065510), BtCoV.HKU5.3 (GenBank Accession No. EF065511), human betacoronavirus 2c Jordan-N3/2012 (GenBank Accession No. KC776174.1; human betacoronavirus 2c EMC/2012 (GenBank Accession No. JX869059.2), Pipistrellus bat coronavirus HKU5 isolates (GenBank Accession No:KC522089.1, GenBank Accession No:KC522088.1, GenBank Accession No:KC522087.1, GenBank Accession No:KC522086.1, GenBank Accession No:KC522085.1, GenBank Accession No: KC522084.1, GenBank Accession No:KC522083.1, GenBank Accession No:KC522082.1, GenBank Accession No:KC522081.1, GenBank Accession No:KC522080.1, GenBank Accession No:KC522079.1, GenBank Accession No:KC522078.1, GenBank Accession No: KC522077.1, GenBank Accession No:KC522076.1, GenBank Accession No:KC522075.1, GenBank Accession No:KC522104.1, GenBank Accession No:KC522104.1, GenBank Accession No:KC522103.1, GenBank Accession No:KC522102.1, GenBank Accession No: KC522101.1, GenBank Accession No:KC522100.1, GenBank Accession No:KC522099.1, GenBank Accession No:KC522098.1, GenBank Accession No:KC522097.1, GenBank Accession No:KC522096.1, GenBank Accession No:KC522095.1, GenBank Accession No: KC522094.1, GenBank Accession No:KC522093.1, GenBank Accession No:KC522092.1, GenBank Accession No:KC522091.1, GenBank Accession No:KC522090.1, GenBank Accession No:KC522119.1 GenBank Accession No:KC522118.1 GenBank Accession No: KC522117.1 GenBank Accession No:KC522116.1 GenBank Accession No:KC522115.1 GenBank Accession No:KC522114.1 GenBank Accession No:KC522113.1 GenBank Accession No:KC522112.1 GenBank Accession No:KC522111.1 GenBank Accession No: KC522110.1 GenBank Accession No:KC522109.1 GenBank Accession No:KC522108.1, GenBank Accession No:KC522107.1, GenBank Accession No:KC522106.1, GenBank Accession No:KC522105.1) Pipistrellus bat coronavirus HKU4 isolates (GenBank Accession No:KC522048.1, GenBank Accession No:KC522047.1, GenBank Accession No:KC522046.1, GenBank Accession No:KC522045.1, GenBank Accession No: KC522044.1, GenBank Accession No:KC522043.1, GenBank Accession No:KC522042.1, GenBank Accession No:KC522041.1, GenBank Accession No:KC522040.1 GenBank Accession No:KC522039.1, GenBank Accession No:KC522038.1, GenBank Accession No:KC522037.1, GenBank Accession No:KC522036.1, GenBank Accession No:KC522048.1 GenBank Accession No:KC522047.1 GenBank Accession No:KC522046.1 GenBank Accession No:KC522045.1 GenBank Accession No:KC522044.1 GenBank Accession No:KC522043.1 GenBank Accession No:KC522042.1 GenBank Accession No:KC522041.1 GenBank Accession No:KC522040.1, GenBank Accession No:KC522039.1 GenBank Accession No:KC522038.1 GenBank Accession No:KC522037.1 GenBank Accession No:KC522036.1, GenBank Accession No:KC522061.1 GenBank Accession No:KC522060.1 GenBank Accession No:KC522059.1 GenBank Accession No:KC522058.1 GenBank Accession No:KC522057.1 GenBank Accession No:KC522056.1 GenBank Accession No:KC522055.1 GenBank Accession No:KC522054.1 GenBank Accession No:KC522053.1 GenBank Accession No:KC522052.1 GenBank Accession No:KC522051.1 GenBank Accession No:KC522050.1 GenBank Accession No:KC522049.1 GenBank Accession No:KC522074.1, GenBank Accession No:KC522073.1 GenBank Accession No:KC522072.1 GenBank Accession No:KC522071.1 GenBank Accession No:KC522070.1 GenBank Accession No:KC522069.1 GenBank Accession No:KC522068.1 GenBank Accession No:KC522067.1, GenBank Accession No:KC522066.1 GenBank Accession No:KC522065.1 GenBank Accession No:KC522064.1, GenBank Accession No:KC522063.1, or GenBank Accession No:KC522062.1, as well as any other subgroup 2b coronavirus now known (e.g., as can be found in the GenBank® Database) or later identified, and any combination thereof.

Nonlimiting examples of a subgroup 1a coronavirus of this invention include FCov.FIPV.79.1146.VR.2202 (GenBank Accession No. NV_007025), transmissible gastroenteritis virus (TGEV) (GenBank Accession No. NC_002306; GenBank Accession No. Q811789.2; GenBank Accession No. DQ811786.2; GenBank Accession No. DQ811788.1; GenBank Accession No. DQ811785.1; GenBank Accession No. X52157.1; GenBank Accession No. AJ011482.1; GenBank Accession No. KC962433.1; GenBank Accession No. AJ271965.2; GenBank Accession No. JQ693060.1; GenBank Accession No. KC609371.1; GenBank Accession No. JQ693060.1; GenBank Accession No. JQ693059.1; GenBank Accession No. JQ693058.1; GenBank Accession No. JQ693057.1; GenBank Accession No. JQ693052.1; GenBank Accession No. JQ693051.1; GenBank Accession No. JQ693050.1), porcine reproductive and respiratory syndrome virus (PRRSV) (GenBank Accession No. NC_001961.1; GenBank Accession No. DQ811787), as well as any other subgroup 1a coronavirus now known (e.g., as can be found in the GenBank® Database) or later identified, and any combination thereof.

Nonlimiting examples of a subgroup 1b coronavirus of this invention include BtCoV.1A.AFCD62 (GenBank Accession No. NC_010437), BtCoV.1B.AFCD307 (GenBank Accession No. NC_010436), BtCov.HKU8.AFCD77 (GenBank Accession No. NC_010438), BtCoV.512.2005 (GenBank Accession No. DQ648858), porcine epidemic diarrhea virus PEDV.CV777 (GenBank Accession No. NC_003436, GenBank Accession No. DQ355224.1, GenBank Accession No. DQ355223.1, GenBank Accession No. DQ355221.1, GenBank Accession No. JN601062.1, GenBank Accession No. N601061.1, GenBank Accession No. JN601060.1, GenBank Accession No. JN601059.1, GenBank Accession No. JN601058.1, GenBank Accession No. JN601057.1, GenBank Accession No. JN601056.1, GenBank Accession No. JN601055.1, GenBank Accession No. JN601054.1, GenBank Accession No. JN601053.1, GenBank Accession No. JN601052.1, GenBank Accession No. JN400902.1, GenBank Accession No. JN547395.1, GenBank Accession No. FJ687473.1, GenBank Accession No. FJ687472.1, GenBank Accession No. FJ687471.1, GenBank Accession No. FJ687470.1, GenBank Accession No. FJ687469.1, GenBank Accession No. FJ687468.1, GenBank Accession No. FJ687467.1, GenBank Accession No. FJ687466.1, GenBank Accession No. FJ687465.1, GenBank Accession No. FJ687464.1, GenBank Accession No. FJ687463.1, GenBank Accession No. FJ687462.1, GenBank Accession No. FJ687461.1, GenBank Accession No. FJ687460.1, GenBank Accession No. FJ687459.1, GenBank Accession No. FJ687458.1, GenBank Accession No.

FJ687457.1, GenBank Accession No. FJ687456.1, GenBank Accession No. FJ687455.1, GenBank Accession No. FJ687454.1, GenBank Accession No. FJ687453 GenBank Accession No. FJ687452.1, GenBank Accession No. FJ687451.1, GenBank Accession No. FJ687450.1, GenBank Accession No. FJ687449.1, GenBank Accession No. AF500215.1, GenBank Accession No. KF476061.1, GenBank Accession No. KF476060.1, GenBank Accession No. KF476059.1, GenBank Accession No. KF476058.1, GenBank Accession No. KF476057.1, GenBank Accession No. KF476056.1, GenBank Accession No. KF476055.1, GenBank Accession No. KF476054.1, GenBank Accession No. KF476053.1, GenBank Accession No. KF476052.1, GenBank Accession No. KF476051.1, GenBank Accession No. KF476050.1, GenBank Accession No. KF476049.1, GenBank Accession No. KF476048.1, GenBank Accession No. KF177258.1, GenBank Accession No. KF177257.1, GenBank Accession No. KF177256.1, GenBank Accession No. KF177255.1), HCoV.229E (GenBank Accession No. NC_002645), HCoV.NL63.Amsterdam.I (GenBank Accession No. NC_005831), BtCoV.HKU2.HK.298.2006 (GenBank Accession No. EF203066), BtCoV.HKU2.HK.33.2006 (GenBank Accession No. EF203067), BtCoV.HKU2.HK.46.2006 (GenBank Accession No. EF203065), BtCoV.HKU2.GD.430.2006 (GenBank Accession No. EF203064), as well as any other subgroup 1b coronavirus now known (e.g., as can be found in the GenBank® Database) or later identified, and any combination thereof.

Nonlimiting examples of a subgroup 2a coronavirus of this invention include HCoV.HKU1.C.N5 (GenBank Accession No. DQ339101), MHV.A59 (GenBank Accession No. NC 001846), PHEV.VW572 (GenBank Accession No. NC 007732), HCoV.OC43.ATCC.VR.759 (GenBank Accession No. NC_005147), bovine enteric coronavirus (BCoV.ENT) (GenBank Accession No. NC_003045), as well as any other subgroup 2a coronavirus now known (e.g., as can be found in the GenBank® Database) or later identified, and any combination thereof.

Nonlimiting examples of a subgroup 2d coronavirus of this invention include BtCoV.HKU9.2 (GenBank Accession No. EF065514), BtCoV.HKU9.1 (GenBank Accession No. NC_009021), BtCoV.HkU9.3 (GenBank Accession No. EF065515), BtCoV.HKU9.4 (GenBank Accession No. EF065516), as well as any other subgroup 2d coronavirus now known (e.g., as can be found in the GenBank® Database) or later identified, and any combination thereof.

Nonlimiting examples of a subgroup 3 coronavirus of this invention include Nonlimiting examples of a subgroup 3 coronavirus of this invention include IBV.Beaudette.IBV.p65 (GenBank Accession No. DQ001339), as well as any other subgroup 3 coronavirus now known (e.g., as can be found in the GenBank® Database) or later identified, and any combination thereof.

The present invention further provides an isolated nucleic acid molecule encoding the chimeric coronavirus spike protein of this invention. In some embodiments, a nucleic acid molecule of this invention can be a cDNA. Also provided is a vector (e.g., a viral or bacterial vector), plasmid or other nucleic acid construct comprising the isolated nucleic acid molecule of this invention.

Further provided herein is a Venezuelan equine encephalitis replicon particle (VRP) comprising the isolated nucleic acid molecule encoding the chimeric coronavirus spike protein of this invention.

In addition, the present invention provides a virus like particle (VLP) comprising the chimeric coronavirus spike protein of any of this invention and a matrix protein of any virus that can form a VLP.

The present invention also provides a coronavirus particle comprising the chimeric coronavirus spike protein of this invention.

Also provided are cells (e.g., isolated cells) comprising the vectors, nucleic acid molecules, VLPs, VRPs, and/or coronavirus particles of the invention.

Additionally provided herein is a population of any of the VLPs, VRPs and for coronavirus particles of this invention, as well as a population of virus particles that are used as viral vectors encoding the chimeric coronavirus spike protein of this invention.

The chimeric coronavirus spike proteins of this invention can be produced as recombinant proteins, e.g., in a eukaryotic cell system for recombination protein production.

The invention also provides immunogenic compositions comprising the cells, vectors, nucleic acid molecules, VLPs, VRPs, coronavirus particles and/or populations of the invention. The composition can further comprise a pharmaceutically acceptable carrier.

The present invention further provides a method of producing an immune response to a coronavirus in a subject, comprising administering to the subject an effective amount of a chimeric coronavirus spike protein, a nucleic acid molecule, a vector, a VRP, a VLP, a coronavirus particle, population and/or a composition of this invention, including any combination thereof, thereby producing an immune response to a coronavirus in the subject.

In further embodiments, the present invention provides a method of treating a coronavirus infection in a subject in need thereof, comprising administering to the subject an effective amount of a chimeric coronavirus spike protein, a nucleic acid molecule, a vector, a VRP, a VLP, a coronavirus particle, population and/or a composition of this invention, including any combination thereof, thereby treating a coronavirus infection in the subject.

Additionally provided herein is a method of preventing a disease or disorder caused by a coronavirus infection in a subject, comprising administering to the subject an effective amount of a chimeric coronavirus spike protein, a nucleic acid molecule, a vector, a VRP, a VLP, a coronavirus particle, population and/or a composition of this invention, including any combination thereof, thereby preventing a disease or disorder caused by a coronavirus infection in the subject.

Furthermore the present invention provides a method of protecting a subject from the effects of coronavirus infection, comprising administering to the subject an effective amount of a chimeric coronavirus spike protein, a nucleic acid molecule, a vector, a VRP, a VLP, a coronavirus particle, population and/or a composition of this invention, including any combination thereof, thereby protecting the subject from the effects of coronavirus infection.

The chimeric coronavirus spike proteins of this invention can be used to immunize a subject against infection by a newly emerging coronavirus, as well as treat a subject infected with a newly emerging coronavirus. For example, the chimeric subgroup 2b coronavirus spike proteins of this invention can be used to immunize against and/or treat infection by bat SARS CoV like virus strains such as Rs SHC014 (GenBank® Accession No. KC881005), Rs3367 (GenBank® Accession No. KC881006) and/or WiV1 S (GenBank® Accession No. KC881007).

In yet further embodiments, the present invention provides a method of identifying a coronavirus spike protein for administration to elicit an immune response to coronavirus in a subject infected by a coronavirus and/or a subject at risk of coronavirus infection and/or to a subject for whom eliciting an immune response to a coronavirus is needed or desired, comprising: a) contacting a sample obtained from a subject infected with a coronavirus with a panel of proteins comprising: 1) one or more chimeric coronavirus spike proteins from a subgroup 2c coronavirus, 2) one or more chimeric coronavirus spike proteins from a subgroup 2b coronavirus, 3) one or more spike proteins from a subgroup 2a coronavirus, 4) one or more chimeric coronavirus spike proteins from a subgroup 2d coronavirus, 5) one or more chimeric coronavirus spike proteins from a subgroup 1a coronavirus, 6) one or more chimeric coronavirus spike proteins from a subgroup 1b coronavirus, 7) one or more chimeric coronavirus spike proteins from a subgroup 3 coronavirus and 8) any combination of (1) through (7) above, under conditions whereby an antigen/antibody complex can form; and b) detecting formation of an antigen/antibody complex, whereby detection of formation of the antigen/antibody complex comprising the chimeric coronavirus spike protein(s) of any of (1)-(6) identifies the presence of antibodies to a spike protein of the coronavirus that is infecting the subject of (a), thereby identifying a coronavirus spike protein for administration to the subject of (a) and/or to a subject infected with a coronavirus and/or to a subject at risk of coronavirus infection and/or to a subject for whom eliciting an immune response to a coronavirus is needed or desired.

In some embodiments, the method set forth above can further comprise the step of administering the coronavirus spike protein identified according to the method to the subject of (a) and/or to a subject at risk of coronavirus infection and/or to a subject infected with a coronavirus and/or to a subject for whom eliciting an immune response to a coronavirus is needed or desired.

A method is also provided herein of identifying an antibody that neutralizes a coronavirus infecting a subject, comprising: a) isolating a coronavirus from a sample of a subject infected with a coronavirus and/or suspected of being infected with a coronavirus; b) contacting the coronavirus of (a) with a panel of antibodies comprising: 1) an antibody reactive with a chimeric coronavirus spike protein from a subgroup 2c coronavirus, 2) an antibody reactive with a chimeric coronavirus spike protein from a subgroup 2b coronavirus, 3) an antibody reactive with a chimeric coronavirus spike protein from a subgroup 2a coronavirus, 4) an antibody reactive with a chimeric coronavirus spike protein from a subgroup 2d coronavirus, 5) an antibody reactive with a chimeric coronavirus spike protein from a subgroup 1a coronavirus, 6) an antibody reactive with a chimeric coronavirus spike protein from a subgroup 1b coronavirus, 7) an antibody reactive with a chimeric coronavirus spike protein from a subgroup 3 coronavirus, and 8) any combination of (1) through (7) above, to form respective coronavirus/antibody compositions, each comprising a respective antibody of the panel; c) contacting each of the respective coronavirus/antibody compositions of (b) with cells susceptible to coronavirus infection under conditions whereby coronavirus infection can occur; and d) detecting the presence or absence of infection of the cells, whereby absence of detection of infection of the cells contacted with any of the coronavirus/antibody compositions of (b) identifies the antibody of that coronavirus/antibody composition as an antibody that neutralizes the coronavirus infecting the subject.

In some embodiments, the method set fort above can further comprise the step of administering the antibody identified according to the method to the subject of (a) and/or to a subject infected with a coronavirus and/or to a subject at risk of coronavirus infection and/or to a subject for whom eliciting an immune response to a coronavirus is needed or desired.

As used herein, "a" or "an" or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz,* 537 F.2d 549, 551-52, 190 USPQ 461, 463 (CCPA 1976) (emphasis in the original); see also MPEP §2111.03.

A "sample" or "biological sample" of this invention can be any biological material, such as a biological fluid, an extract from a cell, an extracellular matrix isolated from a cell, a cell (in solution or bound to a solid support), a tissue, a tissue homogenate, and the like as are well known in the art.

In the methods of this invention in which formation of an antigen/antibody complex is detected, a variety of assays can be employed for such detection. For example, various immunoassays can be used to detect antibodies or proteins (antigens) of this invention. Such immunoassays typically involve the measurement of antigen/antibody complex formation between a protein or peptide (i.e., an antigen) and its specific antibody.

The immunoassays of the invention can be either competitive or noncompetitive and both types of assays are well-known and well-developed in the art. In competitive binding assays, antigen or antibody competes with a detectably labeled antigen or antibody for specific binding to a capture site bound to a solid surface. The concentration of labeled antigen or antibody bound to the capture agent is inversely proportional to the amount of free antigen or antibody present in the sample.

Noncompetitive assays of this invention can be, for example, sandwich assays, in which, for example, the antigen is bound between two antibodies. One of the antibodies is used as a capture agent and is bound to a solid surface. The other antibody is labeled and is used to measure or detect the resultant antigen/antibody complex by e.g., visual or instrument means. A number of combinations of antibody and labeled antibody can be used, as are well known in the art. In some embodiments, the antigen/antibody complex can be detected by other proteins capable of specifically binding human immunoglobulin constant regions, such as protein A, protein L or protein G. These proteins are normal constituents of the cell walls of streptococcal bacteria. They exhibit a strong nonimmunogenic reactivity with immunoglobulin constant regions from a variety of species. (See, e.g., Kronval et al. *J. Immunol.* 111:1401-1406 (1973); Akerstrom et al. *J. Immunol.* 135:2589-2542 (1985)).

In some embodiments, the non-competitive assays need not be sandwich assays. For instance, the antibodies or antigens in the sample can be bound directly to the solid surface. The presence of antibodies or antigens in the sample can then be detected using labeled antigen or antibody, respectively.

In some embodiments, antibodies and/or proteins can be conjugated or otherwise linked or connected (e.g., covalently or noncovalently) to a solid support (e.g., bead, plate, slide, dish, membrane or well) in accordance with known techniques. Antibodies can also be conjugated or otherwise linked or connected to detectable groups such as radiolabels (e.g., $^{35}S$, $^{125}I$, $^{32}P$, $^{13}H$, $^{14}C$, $^{131}I$), enzyme labels (e.g., horseradish peroxidase, alkaline phosphatase), gold beads, chemiluminescence labels, ligands (e.g., biotin) and/or fluorescence labels (e.g., fluorescein) in accordance with known techniques.

A variety of organic and inorganic polymers, both natural and synthetic can be used as the material for the solid surface. Nonlimiting examples of polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that can be used include, but are not limited to, paper, glass, ceramic, metal, metalloids, semiconductive materials, cements and the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes can be employed depending upon the nature of the system.

A variety of immunoassay systems can be used, including but not limited to, radio-immunoassays (RIA), enzyme-linked immunosorbent assays (ELISA) assays, enzyme immunoassays (EIA), "sandwich" assays, gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin/avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, immunoprecipitation, competitive binding assays and immunohistochemical staining. These and other assays are described, among other places, in Hampton et al. (*Serological Methods, a Laboratory Manual*, APS Press, St Paul, Minn. (1990)) and Maddox et al. (*J. Exp. Med.* 158:1211-1216 (1993); the entire contents of which are incorporated herein by reference for teachings directed to immunoassays).

The methods of this invention can also be carried out using a variety of solid phase systems, such as described in U.S. Pat. No. 5,879,881, as well as in a dry strip lateral flow system (e.g., a "dipstick" system), such as described, for example, in U.S. Patent Publication No. 20030073147, the entire contents of each of which are incorporated by reference herein.

Embodiments of the present invention include monoclonal antibodies produced from B cells isolated from a subject of this invention that has produced an immune response against the chimeric coronavirus spike protein of this invention, wherein said monoclonal antibodies are specific to epitopes present on the chimeric coronavirus spike protein. Such monoclonal antibodies can be specific for an epitope in any of the first, second, third or fourth regions of the chimeric coronavirus spike protein of this invention as described herein.

The term "antibody" or "antibodies" as used herein refers to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, or can be a chimeric or humanized antibody. See, e.g., Walker et al., *Molec. Immunol.* 26:403-11 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980. The antibody can further be a single chain antibody or bispecific antibody. The antibody can also be humanized for administration to a human subject.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254:1275-1281).

Monoclonal antibodies can be produced in a hybridoma cell line according to the technique of Kohler and Milstein, (1975) *Nature* 265:495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as *E. coli* by recombinant techniques known to those skilled in the art. See, e.g., W. Huse, (1989) *Science* 246:1275-81.

Antibodies can also be obtained by phage display techniques known in the art or by immunizing a heterologous host with a cell containing an epitope of interest.

"Nidovirus" as used herein refers to viruses within the order Nidovirales, including the families Coronaviridae and Arteriviridae. All viruses within the order Nidovirales share the unique feature of synthesizing a nested set of multiple subgenomic mRNAs. See M. Lai and K. Holmes, *Coronaviridae*: The Viruses and Their Replication, in Fields Virology, pg 1163, ($4^{th}$ Ed. 2001). Particular examples of Coronaviridae include, but are not limited to, toroviruses and coronaviruses.

"Coronavirus" as used herein refers to a genus in the family Coronaviridae, which family is in turn classified within the order Nidovirales. The coronaviruses are large, enveloped, positive-stranded RNA viruses. They have the largest genomes of all RNA viruses and replicate by a unique mechanism that results in a high frequency of recombination. The coronaviruses include antigenic groups I, II, and III. Nonlimiting examples of coronaviruses include SARS coronavirus, MERS coronavirus, transmissible gastroenteritis virus (TGEV), human respiratory coronavirus, porcine respiratory coronavirus, canine coronavirus, feline enteric coronavirus, feline infectious peritonitis virus, rabbit coronavirus, murine hepatitis virus, sialodacryoadenitis virus, porcine hemagglutinating encephalomyelitis virus, bovine coronavirus, avian infectious bronchitis virus, and turkey coronavirus, as well as chimeras of any of the foregoing. See Lai and Holmes "Coronaviridae: The Viruses and Their Replication" in Fields *Virology*, ($4^{th}$ Ed. 2001).

A "nidovirus permissive cell" or "coronavirus permissive cell" as used herein can be any cell in which a coronavirus can at least replicate, including both naturally occurring and recombinant cells. In some embodiments the permissive cell is also one that the nidovirus or coronavirus can infect. The permissive cell can be one that has been modified by recombinant means to produce a cell surface receptor for the nidovirus or coronavirus.

An "isolated" nucleic acid molecule is one that is chemically synthesized (e.g., derived from reverse transcription) or is separated from other nucleic acid molecules that are present in the natural source of the nucleic acid molecule. Preferably, an "isolated" nucleic acid molecule is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. (e.g., as described in Sambrook et al., eds., "Molecular Cloning: A Laboratory Manual," 2nd ed., Cold Spring Harbor Laboratory, Cold Spring Harbor Laboratory Press, Cold Spring Harbor, N.Y., 1989).

In particular embodiments, a nucleic acid of this invention has at least about 50%, 60%, 70%, 75%, 80%, 85%, 90%, 95%, 98% or more nucleic acid sequence homology with the sequences specifically disclosed herein. The term "homology" as used herein refers to a degree of similarity between two or more sequences. There can be partial homology or complete homology (i.e., identity). A partially homologous sequence that at least partially inhibits an identical sequence from hybridizing to a target nucleic acid is referred to using the functional term "substantially homologous." The inhibition of hybridization to the target sequence can be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding can be tested by the use of a second target sequence, which lacks even a partial degree of complementarity (e.g., less than about 30% identity). In the absence of non-specific binding, the probe will not hybridize to the second non-complementary target sequence.

Alternatively stated, in particular embodiments, nucleic acids encoding a cDNA of a coronavirus that hybridize under the conditions described herein to the complement of the sequences specifically disclosed herein can also be used according to the present invention. The term "hybridization" as used herein refers to any process by which a first strand of nucleic acid binds with a second strand of nucleic acid through base pairing.

The term "stringent" as used here refers to hybridization conditions that are commonly understood in the art to define the commodities of the hybridization procedure. High stringency hybridization conditions that will permit homologous nucleotide sequences to hybridize to a nucleotide sequence as given herein are well known in the art. As one example, hybridization of such sequences to the nucleic acid molecules disclosed herein can be carried out in 25% formamide, 5×SSC, 5×Denhardt's solution and 5% dextran sulfate at 42° C., with wash conditions of 25% formamide, 5×SSC and 0.1% SDS at 42° C., to allow hybridization of sequences of about 60% homology. Another example includes hybridization conditions of 6×SSC, 0.1% SDS at about 45° C., followed by wash conditions of 0.2×SSC, 0.1% SDS at 50-65° C. Another example of stringent conditions is represented by a wash stringency of 0.3 M NaCl, 0.03M sodium citrate, 0.1% SDS at 60-70° C. using a standard hybridization assay (see SAMBROOK et al., EDS., MOLECULAR CLONING: A LABORATORY MANUAL 2d ed. (Cold Spring Harbor, N.Y. 1989, the entire contents of which are incorporated by reference herein).

The nucleic acids, proteins, peptides, viruses, vectors, particles, antibodies and populations of this invention are intended for use as therapeutic agents and immunological reagents, for example, as antigens, immunogens, vaccines, and/or nucleic acid delivery vehicles. Thus, in various embodiments, the present invention provides a composition comprising the nucleic acid, virus, vector, particle, antibody and/or population of this invention in a pharmaceutically acceptable carrier. The compositions described herein can be formulated for use as reagents (e.g., to produce antibodies) and/or for administration in a pharmaceutical carrier in accordance with known techniques. See, e.g., Remington, *The Science And Practice of Pharmacy* (latest edition).

In embodiments of this invention wherein a chimeric coronavirus spike protein is being administered, delivered and/or introduced into a subject, e.g., to elicit or induce an immune response, the protein can be administered, delivered and/or introduced into the subject as a protein present in an inactivated (e.g., inactivated through UV irradiation or formalin treatment) coronavirus. The protein or active fragment thereof of this invention can be administered, delivered and/or introduced into the subject according to any method now known or later identified for administration, introduction and/or delivery of protein or active fragment thereof, as would be well known to one of ordinary skill in the art. Nonlimiting examples include administration of the protein or fragment with a protease inhibitor or other agent to protect it from degradation and/or with a polyalkylene glycol moiety (e.g., polyethylene glycol).

In some embodiments, the coronavirus protein or active fragment thereof can be administered to a subject as a nucleic acid molecule, which can be a naked nucleic acid molecule or a nucleic acid molecule present in a vector (e.g., a delivery vector, which in some embodiments can be a VRP). The nucleic acids and vectors of this invention can be administered orally, intranasally, parenterally (e.g., intravenously), by intramuscular injection, by intraperitoneal injection, transdermally, extracorporeally, topically or the like. In the methods described herein which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for expression of the polypeptides and/or fragments of this invention. The vector can be a commercially available preparation or can be constructed in the laboratory according to methods well known in the art.

Delivery of the nucleic acid or vector to cells can be via a variety of mechanisms, including but not limited to recombinant vectors including bacterial, viral and fungal vectors, liposomal delivery agents, nanoparticles, and gene gun related-mechanisms.

As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system, which can package a recombinant retroviral genome. The recombinant retrovirus can then be used to infect and thereby deliver to the infected cells nucleic acid encoding the polypeptide and/or fragment of this invention. The exact method of introducing the exogenous nucleic acid into mammalian cells is, of course, not limited to the use of retroviral vectors. Other techniques are widely available for this procedure including the use of adenoviral vectors, alphaviral vectors (e.g., VRPs), adeno-associated viral (AAV) vectors, lentiviral vectors, pseudotyped retroviral vectors and vaccinia viral vectors, as well as any other viral vectors now known or developed in the future. Physical transduction techniques can also be used, such as liposome delivery and receptor-mediated and other endocytosis mechanisms. This invention can be used in conjunction with any of these or other commonly used gene transfer methods.

If ex vivo methods are employed, cells or tissues can be removed and maintained outside the body according to standard protocols well known in the art. The nucleic acids and vectors of this invention can be introduced into the cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or transplanted back into the subject per standard methods for the cell or tissue type. Standard methods are known for transplantation or infusion of various cells into a subject.

Parenteral administration of the peptides, polypeptides, nucleic acids and/or vectors of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, intranasal, subcutaneous, intramuscular, intraperitoneal, intravenous and intratracheal routes, as well as a slow release or sustained release system such that a constant dosage is maintained. See, e.g., U.S. Pat. No. 3,610,795, which is incorporated by reference herein in its entirety.

In the manufacture of a pharmaceutical composition according to embodiments of the present invention, the composition of this invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. A "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include, without limitation, any of the standard pharmaceutical carriers such as phosphate buffered saline solutions, water, emulsions such as oil/water emulsion, microemulsions and various types of wetting agents. A pharmaceutically acceptable carrier can comprise, consist essentially of or consist of one or more synthetic components (e.g., components that do not naturally occur in nature), as are known in the art.

The carrier may be a solid or a liquid, or both, and is preferably formulated with the composition of this invention as a unit-dose formulation. The pharmaceutical compositions are prepared by any of the well-known techniques of pharmacy including, but not limited to, admixing the components, optionally including one or more accessory ingredients. Exemplary pharmaceutically acceptable carriers include, but are not limited to, sterile pyrogen-free water and sterile pyrogen-free physiological saline solution. Such carriers can further include protein (e.g., serum albumin) and sugar (sucrose, sorbitol, glucose, etc.)

The pharmaceutical compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration. The compositions herein may also be administered via a skin scarification method, or transdermally via a patch or liquid. The compositions may be delivered subdermally in the form of a biodegradable material that releases the compositions over a period of time. The most suitable route in any given case will depend, as is well known in the art, on such factors as the species, age, gender and overall condition of the subject, the nature and severity of the condition being treated and/or on the nature of the particular composition (i.e., dosage, formulation) that is being administered.

A subject of this invention is any animal that is capable of producing an immune response against a coronavirus. A subject of this invention can also be any animal that is susceptible to infection by coronavirus and/or susceptible to diseases or disorders caused by coronavirus infection. A subject of this invention can be a mammal and in particular embodiments is a human, which can be an infant, a child, an adult or an elderly adult. A "subject at risk of infection by a coronavirus" or a "subject at risk of coronavirus infection" is any subject who may be or has been exposed to a coronavirus.

As used herein, an "effective amount" refers to an amount of a compound or composition that is sufficient to produce a desired effect, which can be a therapeutic, prophylactic and/or beneficial effect.

Thus, the present invention provides a method of inducing or eliciting an immune response in a subject, comprising administering to the subject an effective amount of a virus, vector, particle, population and/or composition of this invention.

The present invention also provides a method of treating and/or preventing a coronavirus infection in a subject, comprising administering to the subject an effective amount of a virus, vector, particle, population and/or composition of this invention.

Also as used herein, the terms "treat," "treating" and "treatment" include any type of mechanism, action or activity that results in a change in the medical status of a subject, including an improvement in the condition of the subject (e.g., change or improvement in one or more symptoms and/or clinical parameters), delay in the progression of the condition, delay of the onset of a disease or illness, etc.

One nonlimiting example of an effective amount of a virus or virus particle (e.g., VRP) of this invention is from about $10^4$ to about $10^{10}$, preferably from about $10^5$ to about $10^9$, and in particular from about $10^6$ to about $10^8$ infectious units (IU, as measured by indirect immunofluorescence assay), or virus particles, per dose, which can be administered to a subject, depending upon the age, species and/or condition of the subject being treated. For subunit vaccines (e.g., purified antigens) a dose range of from about 1 to about 100 micrograms can be used. As would be well known to one of ordinary skill in the art, the optimal dosage would need to be determined for any given antigen or vaccine, e.g., according to the method of production and resulting immune response.

As one example, if the nucleic acid of this invention is delivered to the cells of a subject in an adenovirus vector, the dosage for administration of adenovirus to humans can range from about $10^7$ to $10^9$ plaque forming units (pfu) per injection, but can be as high as $10^{12}$, $10^{15}$ and/or $10^{20}$ pfu per injection. Ideally, a subject will receive a single injection. If additional injections are necessary, they can be repeated at daily/weekly/monthly intervals for an indefinite period and/or until the efficacy of the treatment has been established. As set forth herein, the efficacy of treatment can be determined by evaluating the symptoms and clinical parameters described herein and/or by detecting a desired immunological response.

The exact amount of the nucleic acid or vector required will vary from subject to subject, depending on the species, age, weight and general condition of the subject, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein.

For administration of serum or antibodies, as one nonlimiting example, a dosage range of from about 20 to about 40 international Units/Kilogram can be used, although it would be well understood that optimal dosage for administration to a subject of this invention needs to be determined, e.g., according to the method of production and resulting immune response.

In some embodiments of the present invention, the compositions can be administered with an adjuvant. As used herein, "adjuvant" describes a substance, which can be any immunomodulating substance capable of being combined with the polypeptide or nucleic acid vaccine to enhance, improve or otherwise modulate an immune response in a subject without deleterious effect on the subject.

Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN™. adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN™ 85 detergent (ICI Surfactants), 0.7% (v/v) TWEEN™ 80 detergent (ICI Surfactants), 2.5% (v/v) ethanol, 200 pg/ml Quil A, 100 μg/ml cholesterol, and 0.5% (v/v) lecithin Modified SEAM 1/2 is an oil-in-water emulsion comprising 5% (v/v) squalene, 1% (v/v) SPAN™ 85 detergent, 0.7% (v/v) Tween 80 detergent, 2.5% (v/v) ethanol, 100 μg/ml Quil A, and 50 μg/ml cholesterol. Other immunomodulatory agents that can be included in the vaccine include, e.g., one or more interleukins, interferons, or other known cytokines.

In some embodiments, VEE replicon vectors can be used to express coronavirus structural genes in producing combination vaccines. Dendritic cells, which are professional antigen-presenting cells and potent inducers of T-cell responses to viral antigens, are preferred targets of VEE and VEE replicon particle infection, while SARS coronavirus targets the mucosal surfaces of the respiratory and gastrointestinal tract. As the VEE and coronavirus replicon RNAs synergistically interact, two-vector vaccine systems are feasible that may result in increased immunogenicity when compared with either vector alone. Combination prime-boost vaccines (e.g., DNA immunization and vaccinia virus vectors) have dramatically enhanced the immune response (notably cellular responses) against target papillomavirus and lentivirus antigens compared to single-immunization regimens (Chen et al. (2000) *Vaccine* 18:2015-2022; Gonzalo et al. (1999) *Vaccine* 17:887-892; Hanke et al. (1998) *Vaccine* 16:439-445; Pancholi et al. (2000). *J. Infect. Dis.* 182:18-27). Using different recombinant viral vectors (influenza and vaccinia) to prime and boost may also synergistically enhance the immune response, sometimes by an order of magnitude or more (Gonzalo, et al. (1999) *Vaccine* 17:887-892). Thus, the present invention also provides methods of combining different recombinant viral vectors (e.g., VEE and coronavirus) in prime boost protocols.

Examples

A Multivalent Vaccine that Elicits Broader Protection Against Emerging Human Coronaviruses Replicon particles (VRPs) based on Venezuelan Equine Encephalitis Virus (VEEV) have been successfully used as vector platforms to deliver a variety of antigens. However, the requirement of wild type VEEV proteins for packaging restricts their production to biological safety laboratory level 3 (BSL3) containment and the risk of generation of wild-type VEEV through recombination imposes a high risk for use of these VRPs in humans. To circumvent this issue, we constructed VRPs using attenuated VEEV strain 3526, which can be packaged under biological safety laboratory level 2 (BSL2). Using Severe Acute Respiratory Syndrome Coronavirus (SARS-CoV) Spike protein (S) as a model antigen, we show that the VRP 3526 vaccine platform (VRP 3526 S) is equally efficacious in antigen production, antibody induction and protecting young and aged mice from lethal SARS disease caused by homologous and heterologous strains of SARS-CoV.

SARS-CoV originated from a pool of heterologous viruses circulating in bats, confounding vaccine and therapeutic design should future outbreaks emerge. To address this issue, the VRP 3526 platform was used and a synthetically designed chimeric S protein containing different regions of S proteins from of BtCoV HKU3, SARS CoV S and BtCoV 279 S was constructed in V3526 backbone (Chimera S). Chimera S was efficiently expressed and was recognized by polyclonal serum to SARS-CoV. Chimera S was also effective in protecting mice from SARS disease induced by several divergent strains of SARS CoV belonging to subgroup 2b. A zoonotic lethal challenge HKU3 virus from subgroup 2b (HKU3-SRBD-MAv) was then created where receptor binding domain (RBD) from HKU3 Spike was replaced by SARS-CoV RBD. Serial passage of this virus in mice resulted in severe airway disease and lethality. The Chimera S vaccine and SARS-CoV S vaccine was successful in eliciting complete protection from weight loss and viral replication caused by HKU3-SRBD-MAv, whereas BtCoV 279 S and BtCoV HKU 3 S elicited partial protection.

Collectively, these studies describe the generation of a safe VRP platform that can be manufactured under BSL2 and also demonstrate a strategy for broadening vaccine efficacy for epidemic and closely related zoonotic pools which may emerge in the future.

The results as shown in FIGS. 10-18 demonstrate: 1) the generation of a VRP 3526 platform that can be prepared under BSL2; 2) that the VRP 3526 platform has efficacy in young and aged models of SARS disease; 3) the generation of a subgroup specific Chimeric S protein vaccine for coronaviruses; 4) the creation of a subgroup specific lethal zoonotic challenge virus (HKU3-SRBD-MAv) that is representative of a virus that may emerge into the human population in the future; 5) the generation of a Chimera S vaccine that is effective in protection from divergent strains of lethal SARS CoV and HKU3-SRBD-MAv; 6) that a Chimeric Spike vaccine design can be effectively applied to coronaviruses from other subgroups; and 7) that the VRP 3526 platform and chimeric spike vaccine design can be broadly applicable to other zoonotic viruses that may emerge into humans.

All publications, patent applications, patents and other references cited herein are incorporated by reference in their entireties for the teachings relevant to the sentence and/or paragraph in which the reference is presented.

The invention is described by the following claims, with equivalents of the claims to be included therein.

What is claimed is:

1. A chimeric coronavirus spike protein comprising, in orientation from amino to carboxy terminus:

a) a first region comprising a portion of a coronavirus spike protein ectodomain that precedes a coronavirus spike protein receptor binding domain (RBD) as located in a nonchimeric coronavirus spike protein, of a first coronavirus;

b) a second region comprising a coronavirus spike protein receptor binding domain (RBD) of a second coronavirus that is different from said first coronavirus;

c) a third region comprising a portion of a coronavirus spike protein S1 domain as located in a nonchimeric coronavirus spike protein immediately downstream of the RBD, contiguous with a portion of a coronavirus spike protein S2 domain as located immediately upstream of a fusion protein domain in a nonchimeric coronavirus spike protein, wherein said third region is of said first coronavirus; and d) a fourth region comprising a portion of a coronavirus spike protein from the start of the fusion protein domain through the carboxy terminal end as located in a nonchimeric coronavirus spike protein of a third coronavirus that is different from said first coronavirus and said second coronavirus.

2. The chimeric coronavirus spike protein of claim 1, wherein the chimeric coronavirus spike protein is derived from subgroup 1a coronaviruses, subgroup 1b coronaviruses, subgroup 2a coronaviruses, subgroup 2b coronaviruses, subgroup 2c coronaviruses, subgroup 2d coronaviruses or subgroup 3 coronaviruses.

3. The chimeric coronavirus of claim 2, derived from subgroup 2b coronaviruses wherein said first, second and third subgroup 2b coronaviruses are different from one another and wherein the subgroup 2b coronaviruses are selected from the group consisting of Bat SARS CoV (GenBank Accession No. FJ211859), SARS CoV (GenBank Accession No. FJ211860), BtSARS.HKU3.1 (GenBank Accession No. DQ022305), BtSARS.HKU3.2 (GenBank Accession No. DQ084199), BtSARS.HKU3.3 (GenBank Accession No. DQ084200), BtSARS.Rm1 (GenBank Accession No. DQ412043), BtCoV.279.2005 (GenBank Accession No. DQ648857), BtSARS.Rf1 (GenBank Accession No. DQ412042), BtCoV.273.2005 (GenBank Accession No. DQ648856), BtSARS.Rp3 (GenBank Accession No. DQ071615), SARS CoV.A022 (GenBank Accession No. AY686863), SARSCoV.CUHK-W1 (GenBank Accession No. AY278554), SARSCoV.GD01 (GenBank Accession No. AY278489), SARSCoV.HC.SZ.61.03 (GenBank Accession No. AY515512), SARSCoV.SZ16 (GenBank Accession No. AY304488), SARSCoV.Urbani (GenBank Accession No. AY278741), SARSCoV.civet010 (GenBank Accession No. AY572035), and SARSCoV.MA.15 (GenBank Accession No. DQ497008).

4. The chimeric subgroup 2b coronavirus spike protein of claim 3, wherein said first subgroup 2b coronavirus is Bat SARS CoV-HKU3 (GenBank Accession No. FJ211859), said second subgroup 2b coronavirus is SARSCoV.Urbani (GenBank Accession No. AY278741.1), and said third subgroup 2b coronavirus is BtCoV 279.2005 (DQ648857).

5. The chimeric coronavirus spike protein of claim 1, comprising the amino acid sequence:

third subgroup 2c coronaviruses are different from one another and wherein the subgroup 2c coronaviruses are selected from the group consisting of Middle East respiratory syndrome coronavirus isolate Riyadh_2_2012 (GenBank Accession No. KF600652.1), Middle East respiratory syndrome coronavirus isolate Al-Hasa_18_2013 (GenBank Accession No. KF600651.1), Middle East respiratory syndrome coronavirus isolate Al-Hasa_17_2013 (GenBank Accession No. KF600647.1), Middle East respiratory syndrome coronavirus isolate Al-Hasa_15_2013 (GenBank Accession No. KF600645.1), Middle East respiratory syndrome coronavirus isolate Al-Hasa_16_2013 (GenBank Accession No. KF600644.1), Middle East respiratory syndrome coronavirus isolate Al-Hasa_21_2013 (GenBank Accession No. KF600634), Middle East respiratory syndrome coronavirus isolate Al-Hasa_19_2013 (GenBank Accession No. KF600632), Middle East respiratory syndrome coronavirus isolate Buraidah_1_2013 (GenBank Accession No. KF600630.1), Middle East respiratory syndrome coronavirus isolate Hafr-Al-Batin_1_2013 (GenBank Accession No. KF600628.1), Middle East respiratory syndrome coronavirus isolate Al-Hasa_12_2013 (GenBank Accession No. KF600627.1), Middle East respiratory syndrome coronavirus isolate Bisha_1_2012 (GenBank Accession No. KF600620.1), Middle East respiratory syndrome coronavirus isolate Riyadh_3_2013 (GenBank Accession No. KF600613.1), Middle East respiratory syndrome coronavirus isolate Riyadh_1_2012 (GenBank Accession No.

(SEQ ID NO: 1)

```
   1 MKILIFAFLA NLAKAQEGCG IISRKPQPKM AQVSSSRRGV YYNDDIFRSD VLHLTQDYFL
  61 PFDSNLTQYF SLNVDSDRYT YFDNPILDFG DGVYFAATEK SNVIRGWIFG SSFDNTTQSA
 121 VIVNNSTHII IRVCNFNLCK EPMYTVSRGT QQNAWVYQSA FNCTYDRVEK SFQLDTTPKT
 181 GNFKDLREYV FKNRDGFLSV YQTYTAVNLP RGLPTGFSVL KPILKLPFGI NITSYRVVMA
 241 MFSQTTSNFL PESAAYYVGN LKYSTFMLRF NENGTITDAV DCSQNPLAEL KCTIKNFNVD
 301 KGIYQTSNFR VSPTQEVIRF PNITNLCPFG EVFNATKFPS VYAWERKKIS NCVADYSVLY
 361 NSTFFSTFKC YGVSATKLND LCFSNVYADS FVVKGDDVRQ IAPGQTGVIA DYNYKLPDDF
 421 MGCVLAWNTR NIDATSTGNY NYKYRYLRHG KLRPFERDIS NVPFSPDGKP CTPPALNCYW
 481 PLNDYGFYTT TGIGYQPYRV VVLSFELLNA PATVCGPKLS TDLVKNQCVN FNFNGLKGTG
 541 VLTSSSKRFQ SFQQFGRDTS DFTDSVRDPQ TLEILDISPC SFGGVSVITP GTNASSEVAV
 601 LYQDVNCTDV PTAIRADQLT PAWRVYSTGV NVFQTQAGCL IGAEHVNASY ECDIPIGAGI
 661 CASYHTASVL RSTGQKSIVA YTMSLGAENS IAYANNSIAI PTNFSISVTT EVMPVSMAKT
 721 AVDCTMYICG DSLECSNLLL QYGSFCTQLN RALTGIAIEQ DKNTQEVFAQ VKQMYKTPAI
 781 KDFGGFNFSQ ILPDPSKPTK RSFIEDLLFN KVTLADAGFM KQYGDCLGDV SARDLICAQK
 841 FNGLTVLPPL LTDEMVAAYT AALVSGTATA GWTFGAGSAL QIPFAMQMAY RFNGIGVTQN
 901 VLYENQKQIA NQFNKAISQI QESLTTTSTA LGKLQDVVND NAQALNTLVK QLSSNFGAIS
 961 SVLNDILSRL DKVEAEVQID RLITGRLQSL QTYVTQQLIR AAEIRASANL AATKMSECVL
1021 GQSKRVDFCG KGYHLMSFPQ AAPHGVVFLH VTYVPSQERN FTTAPAICHE GKAYFPREGV
1081 FVSNGTSWFI TQRNFYSPQI ITTDNTFVAG NCDVVIGIIN NTVYDPLQPE LDSFKEELDK
1141 YFKNHTSPDV DLGDISGINA SVVNIQKEID RLNEVAKNLN ESLIDLQELG KYEQYIKWPW
1201 YVWLGFIAGL IAIVMVTILL CCMTSCCSCL KGACSCGSCC KFDEDDSEPV LKGVKLHYT.
```

6. The chimeric coronavirus of claim 2, derived from subgroup 2c coronaviruses wherein said first, second and KF600612.1), Middle East respiratory syndrome coronavirus isolate Al-Hasa_3_2013 (GenBank Accession No.

KF186565.1), Middle East respiratory syndrome coronavirus isolate Al-Hasa_1_2013 (GenBank Accession No. KF186567.1), Middle East respiratory syndrome coronavirus isolate Al-Hasa_2_2013 (GenBank Accession No. KF186566.1), Middle East respiratory syndrome coronavirus isolate Al-Hasa_4_2013 (GenBank Accession No. KF186564.1), Middle East respiratory syndrome coronavirus (GenBank Accession No. KF192507.1), Betacoronavirus England 1-N1 (GenBank Accession No. NC_019843), MERS-CoV_SA-N1 (GenBank Accession No. KC667074), an isolate of Middle East Respiratory Syndrome Coronavirus having GenBank Accession No: KF600656.1, GenBank Accession No: KF600655.1, GenBank Accession No: KF600654.1, GenBank Accession No: KF600649.1, GenBank Accession No: KF600648.1, GenBank Accession No: KF600646.1, GenBank Accession No: KF600643.1, GenBank Accession No: KF600642.1, GenBank Accession No: KF600640.1, GenBank Accession No: KF600639.1, GenBank Accession No: KF600638.1, GenBank Accession No: KF600637.1, GenBank Accession No: KF600636.1, GenBank Accession No: KF600635.1, GenBank Accession No: KF600631.1, GenBank Accession No: KF600626.1, GenBank Accession No: KF600625.1, GenBank Accession No: KF600624.1, GenBank Accession No: KF600623.1, GenBank Accession No: KF600622.1, GenBank Accession No: KF600621.1, GenBank Accession No: KF600619.1, GenBank Accession No: KF600618.1, GenBank Accession No: KF600616.1, GenBank Accession No: KF600615.1, GenBank Accession No: KF600614.1, GenBank Accession No: KF600641.1, GenBank Accession No: KF600633.1, GenBank Accession No: KF600629.1, or GenBank Accession No: KF600617.1, Coronavirus Neoromicia/PML-PHE1/RSA/2011 GenBank Accession: KC869678.2, Bat Coronavirus Taper/CILKSA_287/Bisha/Saudi Arabia/GenBank Accession No: KF493885.1, Bat coronavirus Rhhar/CII_KSA_003/Bisha/Saudi Arabia/2013 GenBank Accession No: KF493888.1, Bat coronavirus Pikuh/CII_KSA_001/Riyadh/Saudi Arabia/2013 GenBank Accession No: KF493887.1, Bat coronavirus Rhhar/CII_KSA_002/Bisha/Saudi Arabia/2013 GenBank Accession No: KF493886.1, Bat Coronavirus Rhhar/CII_KSA_004/Bisha/Saudi Arabia/2013 GenBank Accession No: KF493884.1, BtCoV.HKU4.2 (GenBank Accession No. EF065506), BtCoV.HKU4.1 (GenBank Accession No. NC_009019), BtCoV.HKU4.3 (GenBank Accession No. EF065507), BtCoV.HKU4.4 (GenBank Accession No. EF065508), BtCoV133.2005 (GenBank Accession No. NC_008315), BtCoV.HKU5.5 (GenBank Accession No. EF065512); BtCoV.HKU5.1 (GenBank Accession No. NC_009020), BtCoV.HKU5.2 (GenBank Accession No. EF065510), BtCoV.HKU5.3 (GenBank Accession No. EF065511), human betacoronavirus 2c Jordan-N3/2012 (GenBank Accession No. KC776174.11; human betacoronavirus 2c EMC/2012 (GenBank Accession No. JX869059.2), and a Pipistrellus bat coronavirus HKU5 isolate having GenBank Accession No:KC522089.1, GenBank Accession No:KC522088.1, GenBank Accession No:KC522087.1, GenBank Accession No:KC522086.1, GenBank Accession No: KC522085.1, GenBank Accession No:KC522084.1, GenBank Accession No:KC522083.1, GenBank Accession No:KC522082.1, GenBank Accession No:KC522081.1, GenBank Accession No:KC522080.1, GenBank Accession No:KC522079.1, GenBank Accession No: KC522078.1, GenBank Accession No:KC522077.1, GenBank Accession No:KC522076.1, GenBank Accession No:KC522075.1, GenBank Accession No:KC522104.1, GenBank Accession No:KC522104.1, GenBank Accession No:KC522103.1, GenBank Accession No: KC522102.1, GenBank Accession No:KC522101.1, GenBank Accession No:KC522100.1, GenBank Accession No:KC522099.1, GenBank Accession No:KC522098.1, GenBank Accession No:KC522097.1, GenBank Accession No:KC522096.1, GenBank Accession No: KC522095.1, GenBank Accession No:KC522094.1, GenBank Accession No:KC522093.1, GenBank Accession No:KC522092.1, GenBank Accession No:KC522091.1, GenBank Accession No:KC522090.1, GenBank Accession No:KC522119.1 GenBank Accession No: KC522118.1 GenBank Accession No:KC522117.1 GenBank Accession No:KC522116.1 GenBank Accession No:KC522115.1 GenBank Accession No:KC522114.1 GenBank Accession No:KC522113.1 GenBank Accession No:KC522112.1 GenBank Accession No: KC522111.1 GenBank Accession No:KC522110.1 GenBank Accession No:KC522109.1 GenBank Accession No:KC522108.1, GenBank Accession No:KC522107.1, GenBank Accession No:KC522106.1, GenBank Accession No:KC522105.1) Pipistrellus bat coronavirus HKU4 isolates (GenBank Accession No:KC522048.1, GenBank Accession No:KC522047.1, GenBank Accession No:KC522046.1, GenBank Accession No:KC522045.1, GenBank Accession No:KC522044.1, GenBank Accession No:KC522043.1, GenBank Accession No: KC522042.1, GenBank Accession No:KC522041.1, GenBank Accession No:KC522040.1 GenBank Accession No:KC522039.1, GenBank Accession No:KC522038.1, GenBank Accession No:KC522037.1, GenBank Accession No:KC522036.1, GenBank Accession No:KC522048.1 GenBank Accession No:KC522047.1, GenBank Accession No:KC522046.1 GenBank Accession No:KC522045.1 GenBank Accession No:KC522044.1 GenBank Accession No:KC522043.1 GenBank Accession No:KC522042.1 GenBank Accession No:KC522041.1 GenBank Accession No:KC522040.1, GenBank Accession No:KC522039.1 GenBank Accession No:KC522038.1 GenBank Accession No:KC522037.1 GenBank Accession No:KC522036.1, GenBank Accession No:KC522061.1 GenBank Accession No:KC522060.1 GenBank Accession No:KC522059.1 GenBank Accession No:KC522058.1 GenBank Accession No:KC522057.1 GenBank Accession No:KC522056.1 GenBank Accession No:KC522055.1 GenBank Accession No:KC522054.1 GenBank Accession No:KC522053.1 GenBank Accession No:KC522052.1 GenBank Accession No:KC522051.1 GenBank Accession No:KC522050.1 GenBank Accession No:KC522049.1 GenBank Accession No:KC522074.1, GenBank Accession No:KC522073.1 GenBank Accession No:KC522072.1 GenBank Accession No:KC522071.1 GenBank Accession No:KC522070.1 GenBank Accession No:KC522069.1 GenBank Accession No:KC522068.1 GenBank Accession No:KC522067.1, GenBank Accession No:KC522066.1 GenBank Accession No:KC522065.1 GenBank Accession No:KC522064.1, GenBank Accession No:KC522063.1, or GenBank Accession No:KC522062.1.

7. The chimeric subgroup 2c coronavirus spike protein of claim 6, wherein said first subgroup 2c coronavirus is BtCoV HKU4.2 (GenBank Accession No. EF065506.1); said second subgroup 2c coronavirus is MERS-CoV (GenBank Accession No. JX869059.2), and said third subgroup 2c coronavirus is BtCoV HKU5.5 (EF065512.1).

8. The chimeric coronavirus spike protein of claim 1, comprising the amino acid sequence:

(SEQ ID NO: 5)

1 MTLLMCLLMS LLIFVRGCDS QFVDMSPASN TSECLESQVD AAAFSKLMWP YPIDPSKVDG

61 IIYPLGRTYS NITLAYTGLF PLQGDLGSQY LYSVSHAVGH DGDPTKAYIS NYSLLVNDFD

121 NGFVVRIGAA ANSTGTIVIS PSVNTKIKKA YPAFILGSSL TNTSAGQPLY ANYSLTIIPD

181 GCGTVLHAFY CILKPRTVNR CPSGTGYVSY FIYETVHNDC QSTINRNASL NSFKSFFDLV

241 NCTFFNSWDI TADETKEWFG ITQDTQGVHL YSSRKGDLYG GNMFRFATLP VYEGIKYYTV

301 IPRSFRSKAN KREAWAAFYV YKLHQLTYLL DFSVDGYIRR AIDCGHDDLS QLHCSYTSFE

361 VDTGVYSVSS YEAKPSGSVV EQAEGVECDF SPLLSGTPPQ VYNFKRLVFT NCNYNLTKLL

421 SLFSVNDFTC SQISPAAIAS NCYSSLILDY FSYPLSMKSD LSVSSAGPIS QFNYKQSFSN

481 PTCLILATVP HNLTTITKPL KYSYINKCSR LLSDDRTEVP QLVNANQYSP CVSIVPSTVW

541 EDGDYYRKQL SPLEGGGWLV ASGSTVAMTE QLQMGFGITV QYGTDTNSVC PKLDLGDSLT

601 ITNRLGKCVD YSLYGVTGRG VFQNCTAVGV KQQRFVYDSF DNLVGYYSDD GNYYCVRPCV

661 SVPVSVIyDK STNLHATLFG SVACEHVTTM MSQFSRLTQS NLRRRDSNIP LQTAVGCVIG

721 LSNNSLVVSD CKLPLGQSLC AVPPVSTFRS YSASQFQLAV LNYTSPIVVT PINSSGFTAA

781 IPTNFSFSVT QEYIETSIQK VTVDCKQYVC NGFTRCEKLL VEYGQFCSKI NQALHGANLR

841 QDESVYSLYS NIKTTSTQTL EYGLNGDFNL TLLQVPQIGG SSSSYRSAIE DLLFDKVTIA

901 DPGYMQGYDD CMKQGPQSAR DLICAQYVSG YKVLPPLYDP NMEAAYTSSL LGSIAGAGWT

961 AGLSSFAAIP FAQSMFYRLN GVG*ITQQVLS ENQKIIANKF NQALGAMQTG FTTTNLAFNK*

1021 *VQDAVNANAM ALSKLAAELS NTFGAISSSI SDILARLDTV EQEAQIDRLI NGRLTSLNAF*

1081 *VAQQLVRTEA AARSAQLAQD KVNECVKSQS KRNGFCGTGT HIVSFAINAP NGLYFFHVGY*

1141 *QPTSHVNATA AYGLCNTENP PKCIAPIDGY FVLNQTTSTA RSSGDQHWYY TGSSFFHPEP*

1201 *ITEANSKYVS MDVKFENLTN KLPPPLLSNS TDLDFKDELE EFFKNVSSQG PNFQEISKIN*

1261 *TTLLNLNTEL MVLSEVVKQL NESYIDLKEL GNYTFYQKWP WYIWLGFIAG LVALALCVFF*

1321 *ILCCTGCGTS CLGKLKCNRC CDSYDEYEVE KIHVH.*

9. An isolated nucleic acid molecule encoding the chimeric coronavirus spike protein of claim 1.

10. A vector comprising the isolated nucleic acid molecule encoding the chimeric coronavirus spike protein of claim 1.

11. A Venezuelan equine encephalitis replicon particle (VRP) comprising the isolated nucleic acid molecule encoding the chimeric coronavirus spike protein of claim 1.

12. A virus like particle (VLP) comprising the chimeric coronavirus spike protein of claim 1 and a matrix protein of any virus that can form a VLP.

13. A coronavirus particle comprising the chimeric coronavirus spike protein of claim 1.

14. A population of VLPs of claim 12.

15. A composition comprising the chimeric spike protein of claim 1 in a pharmaceutically acceptable carrier.

16. A composition comprising the nucleic acid molecule of claim 9 in a pharmaceutically acceptable carrier.

17. A composition comprising the vector of claim 10 in a pharmaceutically acceptable carrier.

18. A composition comprising the VRP of claim 11 in a pharmaceutically acceptable carrier.

19. A composition comprising the population of claim 14 in a pharmaceutically acceptable carrier.

20. A method of producing an immune response to a coronavirus in a subject, comprising administering to the subject an effective amount of the chimeric coronavirus spike protein of claim 1, thereby producing an immune response to a coronavirus in the subject.

21. A method of treating a coronavirus infection in a subject in need thereof, comprising administering to the subject an effective amount of the chimeric coronavirus spike protein of claim 1, thereby treating a coronavirus infection in the subject.

22. A method of preventing a disease or disorder caused by a coronavirus infection in a subject, comprising administering to the subject an effective amount of the chimeric coronavirus spike protein of claim 1, thereby preventing a disease or disorder caused by a coronavirus infection in the subject.

23. A method of protecting a subject from the effects of coronavirus infection, comprising administering to the subject an effective amount of the chimeric coronavirus spike protein of claim 1, thereby protection the subject from the effects of coronavirus infection.

* * * * *

UNITED STATES PATENT AND TRADEMARK OFFICE

CERTIFICATE OF CORRECTION

PATENT NO. : 9,884,895 B2
APPLICATION NO. : 15/124992
DATED : February 6, 2018
INVENTOR(S) : Baric et al.

It is certified that error appears in the above-identified patent and that said Letters Patent is hereby corrected as shown below:

In the Specification

Column 4, Line 40:
Please correct "S ma" to read -- $S_{MIX}$ --

Column 4, Line 43:
Please correct "S ma" to read -- $S_{MIX}$ --

Column 6, Line 40:
Please correct "51" to read -- S1 --

Column 19, Line 52:
Please correct "SARSCoV.GDO1" to read -- SARSCoV.GD01 --

Column 21, Line 7:
Please correct "NC 008315" to read -- NC_008315 --

Column 22, Line 49:
Please correct "N601061.1" to read -- JN601061.1 --

Column 23, Line 34:
Please correct "NC 001846" to read -- NC_001846 --

Column 23, Lines 34-35:
Please correct "NC 007732" to read -- NC_007732 --

Signed and Sealed this
Twenty-fourth Day of July, 2018

Andrei Iancu
*Director of the United States Patent and Trademark Office*

In the Claims

Column 91, Claim 6, Line 34:
Please correct "Taper/CILKSA_287/" to read -- Taper/CII_KSA_287/ --

Column 91, Claim 6, Line 53:
Please correct "KC776174.11;" to read -- KC776174.1); --

Column 93, Claim 8, Sequence 661:
Please correct "SVPVSVIyDK" to read -- SVPVSVIYDK --

SEQUENCE LISTING

```
<160> NUMBER OF SEQ ID NOS: 8

<210> SEQ ID NO 1
<211> LENGTH: 1259
<212> TYPE: PRT
<213> ORGANISM: Artificial
<220> FEATURE:
<223> OTHER INFORMATION: chimeric coronavirus spike protein

<400> SEQUENCE: 1

Met Lys Ile Leu Ile Phe Ala Phe Leu Ala Asn Leu Ala Lys Ala Gln
1               5                   10                  15

Glu Gly Cys Gly Ile Ile Ser Arg Lys Pro Gln Pro Lys Met Ala Gln
            20                  25                  30

Val Ser Ser Ser Arg Arg Gly Val Tyr Tyr Asn Asp Asp Ile Phe Arg
        35                  40                  45

Ser Asp Val Leu His Leu Thr Gln Asp Tyr Phe Leu Pro Phe Asp Ser
    50                  55                  60

Asn Leu Thr Gln Tyr Phe Ser Leu Asn Val Asp Ser Asp Arg Tyr Thr
65                  70                  75                  80

Tyr Phe Asp Asn Pro Ile Leu Asp Phe Gly Asp Gly Val Tyr Phe Ala
                85                  90                  95

Ala Thr Glu Lys Ser Asn Val Ile Arg Gly Trp Ile Phe Gly Ser Ser
            100                 105                 110

Phe Asp Asn Thr Thr Gln Ser Ala Val Ile Val Asn Asn Ser Thr His
        115                 120                 125

Ile Ile Ile Arg Val Cys Asn Phe Asn Leu Cys Lys Glu Pro Met Tyr
    130                 135                 140

Thr Val Ser Arg Gly Thr Gln Gln Asn Ala Trp Val Tyr Gln Ser Ala
145                 150                 155                 160
```

-continued

```
Phe Asn Cys Thr Tyr Asp Arg Val Glu Lys Ser Phe Gln Leu Asp Thr
                165                 170                 175

Thr Pro Lys Thr Gly Asn Phe Lys Asp Leu Arg Glu Tyr Val Phe Lys
            180                 185                 190

Asn Arg Asp Gly Phe Leu Ser Val Tyr Gln Thr Tyr Thr Ala Val Asn
        195                 200                 205

Leu Pro Arg Gly Leu Pro Thr Gly Phe Ser Val Leu Lys Pro Ile Leu
    210                 215                 220

Lys Leu Pro Phe Gly Ile Asn Ile Thr Ser Tyr Arg Val Val Met Ala
225                 230                 235                 240

Met Phe Ser Gln Thr Thr Ser Asn Phe Leu Pro Glu Ser Ala Ala Tyr
                245                 250                 255

Tyr Val Gly Asn Leu Lys Tyr Ser Thr Phe Met Leu Arg Phe Asn Glu
            260                 265                 270

Asn Gly Thr Ile Thr Asp Ala Val Asp Cys Ser Gln Asn Pro Leu Ala
        275                 280                 285

Glu Leu Lys Cys Thr Ile Lys Asn Phe Asn Val Asp Lys Gly Ile Tyr
    290                 295                 300

Gln Thr Ser Asn Phe Arg Val Ser Pro Thr Gln Glu Val Ile Arg Phe
305                 310                 315                 320

Pro Asn Ile Thr Asn Leu Cys Pro Phe Gly Glu Val Phe Asn Ala Thr
                325                 330                 335

Lys Phe Pro Ser Val Tyr Ala Trp Glu Arg Lys Lys Ile Ser Asn Cys
            340                 345                 350

Val Ala Asp Tyr Ser Val Leu Tyr Asn Ser Thr Phe Phe Ser Thr Phe
        355                 360                 365

Lys Cys Tyr Gly Val Ser Ala Thr Lys Leu Asn Asp Leu Cys Phe Ser
    370                 375                 380

Asn Val Tyr Ala Asp Ser Phe Val Val Lys Gly Asp Asp Val Arg Gln
385                 390                 395                 400

Ile Ala Pro Gly Gln Thr Gly Val Ile Ala Asp Tyr Asn Tyr Lys Leu
                405                 410                 415

Pro Asp Asp Phe Met Gly Cys Val Leu Ala Trp Asn Thr Arg Asn Ile
            420                 425                 430

Asp Ala Thr Ser Thr Gly Asn Tyr Asn Tyr Lys Tyr Arg Tyr Leu Arg
        435                 440                 445

His Gly Lys Leu Arg Pro Phe Glu Arg Asp Ile Ser Asn Val Pro Phe
    450                 455                 460

Ser Pro Asp Gly Lys Pro Cys Thr Pro Pro Ala Leu Asn Cys Tyr Trp
465                 470                 475                 480

Pro Leu Asn Asp Tyr Gly Phe Tyr Thr Thr Thr Gly Ile Gly Tyr Gln
                485                 490                 495

Pro Tyr Arg Val Val Val Leu Ser Phe Glu Leu Leu Asn Ala Pro Ala
            500                 505                 510

Thr Val Cys Gly Pro Lys Leu Ser Thr Asp Leu Val Lys Asn Gln Cys
        515                 520                 525

Val Asn Phe Asn Phe Asn Gly Leu Lys Gly Thr Gly Val Leu Thr Ser
    530                 535                 540

Ser Ser Lys Arg Phe Gln Ser Phe Gln Gln Phe Gly Arg Asp Thr Ser
545                 550                 555                 560

Asp Phe Thr Asp Ser Val Arg Asp Pro Gln Thr Leu Glu Ile Leu Asp
                565                 570                 575
```

-continued

```
Ile Ser Pro Cys Ser Phe Gly Gly Val Ser Val Ile Thr Pro Gly Thr
            580                 585                 590

Asn Ala Ser Ser Glu Val Ala Val Leu Tyr Gln Asp Val Asn Cys Thr
        595                 600                 605

Asp Val Pro Thr Ala Ile Arg Ala Asp Gln Leu Thr Pro Ala Trp Arg
    610                 615                 620

Val Tyr Ser Thr Gly Val Asn Val Phe Gln Thr Gln Ala Gly Cys Leu
625                 630                 635                 640

Ile Gly Ala Glu His Val Asn Ala Ser Tyr Glu Cys Asp Ile Pro Ile
                645                 650                 655

Gly Ala Gly Ile Cys Ala Ser Tyr His Thr Ala Ser Val Leu Arg Ser
            660                 665                 670

Thr Gly Gln Lys Ser Ile Val Ala Tyr Thr Met Ser Leu Gly Ala Glu
        675                 680                 685

Asn Ser Ile Ala Tyr Ala Asn Asn Ser Ile Ala Ile Pro Thr Asn Phe
    690                 695                 700

Ser Ile Ser Val Thr Thr Glu Val Met Pro Val Ser Met Ala Lys Thr
705                 710                 715                 720

Ala Val Asp Cys Thr Met Tyr Ile Cys Gly Asp Ser Leu Glu Cys Ser
                725                 730                 735

Asn Leu Leu Leu Gln Tyr Gly Ser Phe Cys Thr Gln Leu Asn Arg Ala
            740                 745                 750

Leu Thr Gly Ile Ala Ile Glu Gln Asp Lys Asn Thr Gln Glu Val Phe
        755                 760                 765

Ala Gln Val Lys Gln Met Tyr Lys Thr Pro Ala Ile Lys Asp Phe Gly
    770                 775                 780

Gly Phe Asn Phe Ser Gln Ile Leu Pro Asp Pro Ser Lys Pro Thr Lys
785                 790                 795                 800

Arg Ser Phe Ile Glu Asp Leu Leu Phe Asn Lys Val Thr Leu Ala Asp
                805                 810                 815

Ala Gly Phe Met Lys Gln Tyr Gly Asp Cys Leu Gly Asp Val Ser Ala
            820                 825                 830

Arg Asp Leu Ile Cys Ala Gln Lys Phe Asn Gly Leu Thr Val Leu Pro
        835                 840                 845

Pro Leu Leu Thr Asp Glu Met Val Ala Ala Tyr Thr Ala Ala Leu Val
    850                 855                 860

Ser Gly Thr Ala Thr Ala Gly Trp Thr Phe Gly Ala Gly Ser Ala Leu
865                 870                 875                 880

Gln Ile Pro Phe Ala Met Gln Met Ala Tyr Arg Phe Asn Gly Ile Gly
                885                 890                 895

Val Thr Gln Asn Val Leu Tyr Glu Asn Gln Lys Gln Ile Ala Asn Gln
            900                 905                 910

Phe Asn Lys Ala Ile Ser Gln Ile Gln Glu Ser Leu Thr Thr Thr Ser
        915                 920                 925

Thr Ala Leu Gly Lys Leu Gln Asp Val Val Asn Asp Asn Ala Gln Ala
    930                 935                 940

Leu Asn Thr Leu Val Lys Gln Leu Ser Ser Asn Phe Gly Ala Ile Ser
945                 950                 955                 960

Ser Val Leu Asn Asp Ile Leu Ser Arg Leu Asp Lys Val Glu Ala Glu
                965                 970                 975

Val Gln Ile Asp Arg Leu Ile Thr Gly Arg Leu Gln Ser Leu Gln Thr
            980                 985                 990

Tyr Val Thr Gln Gln Leu Ile Arg  Ala Ala Glu Ile Arg  Ala Ser Ala
```

```
        995                 1000                1005

Asn Leu  Ala Ala Thr Lys Met  Ser Glu Cys Val Leu  Gly Gln Ser
    1010                 1015                 1020

Lys Arg  Val Asp Phe Cys Gly  Lys Gly Tyr His Leu  Met Ser Phe
    1025                 1030                 1035

Pro Gln  Ala Ala Pro His Gly  Val Val Phe Leu His  Val Thr Tyr
    1040                 1045                 1050

Val Pro  Ser Gln Glu Arg Asn  Phe Thr Thr Ala Pro  Ala Ile Cys
    1055                 1060                 1065

His Glu  Gly Lys Ala Tyr Phe  Pro Arg Glu Gly Val  Phe Val Ser
    1070                 1075                 1080

Asn Gly  Thr Ser Trp Phe Ile  Thr Gln Arg Asn Phe  Tyr Ser Pro
    1085                 1090                 1095

Gln Ile  Ile Thr Thr Asp Asn  Thr Phe Val Ala Gly  Asn Cys Asp
    1100                 1105                 1110

Val Val  Ile Gly Ile Ile Asn  Asn Thr Val Tyr Asp  Pro Leu Gln
    1115                 1120                 1125

Pro Glu  Leu Asp Ser Phe Lys  Glu Glu Leu Asp Lys  Tyr Phe Lys
    1130                 1135                 1140

Asn His  Thr Ser Pro Asp Val  Asp Leu Gly Asp Ile  Ser Gly Ile
    1145                 1150                 1155

Asn Ala  Ser Val Val Asn Ile  Gln Lys Glu Ile Asp  Arg Leu Asn
    1160                 1165                 1170

Glu Val  Ala Lys Asn Leu Asn  Glu Ser Leu Ile Asp  Leu Gln Glu
    1175                 1180                 1185

Leu Gly  Lys Tyr Glu Gln Tyr  Ile Lys Trp Pro Trp  Tyr Val Trp
    1190                 1195                 1200

Leu Gly  Phe Ile Ala Gly Leu  Ile Ala Ile Val Met  Val Thr Ile
    1205                 1210                 1215

Leu Leu  Cys Cys Met Thr Ser  Cys Cys Ser Cys Leu  Lys Gly Ala
    1220                 1225                 1230

Cys Ser  Cys Gly Ser Cys Cys  Lys Phe Asp Glu Asp  Asp Ser Glu
    1235                 1240                 1245

Pro Val  Leu Lys Gly Val Lys  Leu His Tyr Thr
    1250                 1255


<210> SEQ ID NO 2
<211> LENGTH: 1242
<212> TYPE: PRT
<213> ORGANISM: Artificial
<220> FEATURE:
<223> OTHER INFORMATION: SARS coronavirus

<400> SEQUENCE: 2

Met Lys Ile Leu Ile Phe Ala Phe Leu Ala Asn Leu Ala Lys Ala Gln
1               5                   10                  15

Glu Gly Cys Gly Ile Ile Ser Arg Lys Pro Gln Pro Lys Met Ala Gln
            20                  25                  30

Val Ser Ser Ser Arg Arg Gly Val Tyr Tyr Asn Asp Asp Ile Phe Arg
        35                  40                  45

Ser Asp Val Leu His Leu Thr Gln Asp Tyr Phe Leu Pro Phe Asp Ser
    50                  55                  60

Asn Leu Thr Gln Tyr Phe Ser Leu Asn Val Asp Ser Asp Arg Tyr Thr
65                  70                  75                  80

Tyr Phe Asp Asn Pro Ile Leu Asp Phe Gly Asp Gly Val Tyr Phe Ala
```

-continued

```
                85                  90                  95

Ala Thr Glu Lys Ser Asn Val Ile Arg Gly Trp Ile Phe Gly Ser Ser
            100                 105                 110

Phe Asp Asn Thr Thr Gln Ser Ala Val Ile Val Asn Asn Ser Thr His
        115                 120                 125

Ile Ile Ile Arg Val Cys Asn Phe Asn Leu Cys Lys Glu Pro Met Tyr
    130                 135                 140

Thr Val Ser Arg Gly Thr Gln Gln Asn Ala Trp Val Tyr Gln Ser Ala
145                 150                 155                 160

Phe Asn Cys Thr Tyr Asp Arg Val Glu Lys Ser Phe Gln Leu Asp Thr
                165                 170                 175

Thr Pro Lys Thr Gly Asn Phe Lys Asp Leu Arg Glu Tyr Val Phe Lys
            180                 185                 190

Asn Arg Asp Gly Phe Leu Ser Val Tyr Gln Thr Tyr Thr Ala Val Asn
        195                 200                 205

Leu Pro Arg Gly Leu Pro Thr Gly Phe Ser Val Leu Lys Pro Ile Leu
    210                 215                 220

Lys Leu Pro Phe Gly Ile Asn Ile Thr Ser Tyr Arg Val Val Met Ala
225                 230                 235                 240

Met Phe Ser Gln Thr Thr Ser Asn Phe Leu Pro Glu Ser Ala Ala Tyr
                245                 250                 255

Tyr Val Gly Asn Leu Lys Tyr Ser Thr Phe Met Leu Arg Phe Asn Glu
            260                 265                 270

Asn Gly Thr Ile Thr Asp Ala Val Asp Cys Ser Gln Asn Pro Leu Ala
        275                 280                 285

Glu Leu Lys Cys Thr Ile Lys Asn Phe Asn Val Asp Lys Gly Ile Tyr
    290                 295                 300

Gln Thr Ser Asn Phe Arg Val Ser Pro Thr Gln Glu Val Ile Arg Phe
305                 310                 315                 320

Pro Asn Ile Thr Asn Arg Cys Pro Phe Asp Lys Val Phe Asn Ala Thr
                325                 330                 335

Arg Phe Pro Asn Val Tyr Ala Trp Glu Arg Thr Lys Ile Ser Asp Cys
            340                 345                 350

Val Ala Asp Tyr Thr Val Leu Tyr Asn Ser Thr Ser Phe Ser Thr Phe
        355                 360                 365

Lys Cys Tyr Gly Val Ser Pro Ser Lys Leu Ile Asp Leu Cys Phe Thr
    370                 375                 380

Ser Val Tyr Ala Asp Thr Phe Leu Ile Arg Ser Ser Glu Val Arg Gln
385                 390                 395                 400

Val Ala Pro Gly Glu Thr Gly Val Ile Ala Asp Tyr Asn Tyr Lys Leu
                405                 410                 415

Pro Asp Asp Phe Thr Gly Cys Val Ile Ala Trp Asn Thr Ala Lys His
            420                 425                 430

Asp Thr Gly Asn Tyr Tyr Tyr Arg Ser His Arg Lys Thr Lys Leu Lys
        435                 440                 445

Pro Phe Glu Arg Asp Leu Ser Ser Asp Asp Gly Asn Gly Val Tyr Thr
    450                 455                 460

Leu Ser Thr Tyr Asp Phe Asn Pro Asn Val Pro Val Ala Tyr Gln Ala
465                 470                 475                 480

Thr Arg Val Val Val Leu Ser Phe Glu Leu Leu Asn Ala Pro Ala Thr
                485                 490                 495

Val Cys Gly Pro Lys Leu Ser Thr Glu Leu Val Lys Asn Gln Cys Val
            500                 505                 510
```

-continued

```
Asn Phe Asn Phe Asn Gly Leu Lys Gly Thr Gly Val Leu Thr Ser Ser
        515                 520                 525

Ser Lys Arg Phe Gln Ser Phe Gln Gln Phe Gly Arg Asp Thr Ser Asp
    530                 535                 540

Phe Thr Asp Ser Val Arg Asp Pro Gln Thr Leu Glu Ile Leu Asp Ile
545                 550                 555                 560

Ser Pro Cys Ser Phe Gly Gly Val Ser Val Ile Thr Pro Gly Thr Asn
                565                 570                 575

Ala Ser Ser Glu Val Ala Val Leu Tyr Gln Asp Val Asn Cys Thr Asp
            580                 585                 590

Val Pro Thr Ala Ile Arg Ala Asp Gln Leu Thr Pro Ala Trp Arg Val
        595                 600                 605

Tyr Ser Thr Gly Val Asn Val Phe Gln Thr Gln Ala Gly Cys Leu Ile
    610                 615                 620

Gly Ala Glu His Val Asn Ala Ser Tyr Glu Cys Asp Ile Pro Ile Gly
625                 630                 635                 640

Ala Gly Ile Cys Ala Ser Tyr His Thr Ala Ser Val Leu Arg Ser Thr
                645                 650                 655

Gly Gln Lys Ser Ile Val Ala Tyr Thr Met Ser Leu Gly Ala Glu Asn
            660                 665                 670

Ser Ile Ala Tyr Ala Asn Asn Ser Ile Ala Ile Pro Thr Asn Phe Ser
        675                 680                 685

Ile Ser Val Thr Thr Glu Val Met Pro Val Ser Met Ala Lys Thr Ala
    690                 695                 700

Val Asp Cys Thr Met Tyr Ile Cys Gly Asp Ser Leu Glu Cys Ser Asn
705                 710                 715                 720

Leu Leu Leu Gln Tyr Gly Ser Phe Cys Thr Gln Leu Asn Arg Ala Leu
                725                 730                 735

Thr Gly Ile Ala Ile Glu Gln Asp Lys Asn Thr Gln Glu Val Phe Ala
            740                 745                 750

Gln Val Lys Gln Met Tyr Lys Thr Pro Ala Ile Lys Asp Phe Gly Gly
        755                 760                 765

Phe Asn Phe Ser Gln Ile Leu Pro Asp Pro Ser Lys Pro Thr Lys Arg
    770                 775                 780

Ser Phe Ile Glu Asp Leu Leu Phe Asn Lys Val Thr Leu Ala Asp Ala
785                 790                 795                 800

Gly Phe Met Lys Gln Tyr Gly Asp Cys Leu Gly Asp Val Ser Ala Arg
                805                 810                 815

Asp Leu Ile Cys Ala Gln Lys Phe Asn Gly Leu Thr Val Leu Pro Pro
            820                 825                 830

Leu Leu Thr Asp Glu Met Val Ala Ala Tyr Thr Ala Ala Leu Val Ser
        835                 840                 845

Gly Thr Ala Thr Ala Gly Trp Thr Phe Gly Ala Gly Ala Ala Leu Gln
    850                 855                 860

Ile Pro Phe Ala Met Gln Met Ala Tyr Arg Phe Asn Gly Ile Gly Val
865                 870                 875                 880

Thr Gln Asn Val Leu Tyr Glu Asn Gln Lys Leu Ile Ala Asn Gln Phe
                885                 890                 895

Asn Ser Ala Ile Gly Lys Ile Gln Glu Ser Leu Ser Ser Thr Ala Ser
            900                 905                 910

Ala Leu Gly Lys Leu Gln Asp Val Val Asn Gln Asn Ala Gln Ala Leu
        915                 920                 925
```

Asn Thr Leu Val Lys Gln Leu Ser Ser Asn Phe Gly Ala Ile Ser Ser
    930                 935                 940

Val Leu Asn Asp Ile Leu Ser Arg Leu Asp Lys Val Glu Ala Glu Val
945                 950                 955                 960

Gln Ile Asp Arg Leu Ile Thr Gly Arg Leu Gln Ser Leu Gln Thr Tyr
                965                 970                 975

Val Thr Gln Gln Leu Ile Arg Ala Ala Glu Ile Arg Ala Ser Ala Asn
            980                 985                 990

Leu Ala Ala Thr Lys Met Ser Glu Cys Val Leu Gly Gln Ser Lys Arg
        995                 1000                1005

Val Asp Phe Cys Gly Lys Gly Tyr His Leu Met Ser Phe Pro Gln
    1010                1015                1020

Ser Ala Pro His Gly Val Val Phe Leu His Val Thr Tyr Val Pro
    1025                1030                1035

Ser Gln Glu Lys Asn Phe Thr Thr Ala Pro Ala Ile Cys His Glu
    1040                1045                1050

Gly Lys Ala Tyr Phe Pro Arg Glu Gly Val Phe Val Ser Asn Gly
    1055                1060                1065

Thr Ser Trp Phe Ile Thr Gln Arg Asn Phe Tyr Ser Pro Gln Leu
    1070                1075                1080

Ile Thr Thr Asp Asn Thr Phe Val Ser Gly Asn Cys Asp Val Val
    1085                1090                1095

Ile Gly Ile Ile Asn Asn Thr Val Tyr Asp Pro Leu Gln Pro Glu
    1100                1105                1110

Leu Asp Ser Phe Lys Glu Glu Leu Asp Lys Tyr Phe Lys Asn His
    1115                1120                1125

Thr Ser Pro Asp Val Asp Leu Gly Asp Ile Ser Gly Ile Asn Ala
    1130                1135                1140

Ser Val Val Asn Ile Gln Lys Glu Ile Asp Arg Leu Asn Glu Val
    1145                1150                1155

Ala Lys Asn Leu Asn Glu Ser Leu Ile Asp Leu Gln Glu Leu Gly
    1160                1165                1170

Lys Tyr Glu Gln Tyr Ile Lys Trp Pro Trp Tyr Val Trp Leu Gly
    1175                1180                1185

Phe Ile Ala Gly Leu Ile Ala Ile Val Met Val Thr Ile Leu Leu
    1190                1195                1200

Cys Cys Met Thr Ser Cys Cys Ser Cys Leu Lys Gly Ala Cys Ser
    1205                1210                1215

Cys Gly Ser Cys Cys Lys Phe Asp Glu Asp Asp Ser Glu Pro Val
    1220                1225                1230

Leu Lys Gly Val Lys Leu His Tyr Thr
    1235                1240

<210> SEQ ID NO 3
<211> LENGTH: 1255
<212> TYPE: PRT
<213> ORGANISM: Artificial
<220> FEATURE:
<223> OTHER INFORMATION: SARS coronavirus

<400> SEQUENCE: 3

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

-continued

```
His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
```

-continued

```
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880
```

-continued

```
Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                 1015                 1020

Phe Cys  Gly Lys Gly Tyr His  Leu Met Ser Phe Pro  Gln Ala Ala
    1025                 1030                 1035

Pro His  Gly Val Val Phe Leu  His Val Thr Tyr Val  Pro Ser Gln
    1040                 1045                 1050

Glu Arg  Asn Phe Thr Thr Ala  Pro Ala Ile Cys His  Glu Gly Lys
    1055                 1060                 1065

Ala Tyr  Phe Pro Arg Glu Gly  Val Phe Val Phe Asn  Gly Thr Ser
    1070                 1075                 1080

Trp Phe  Ile Thr Gln Arg Asn  Phe Phe Ser Pro Gln  Ile Ile Thr
    1085                 1090                 1095

Thr Asp  Asn Thr Phe Val Ser  Gly Asn Cys Asp Val  Val Ile Gly
    1100                 1105                 1110

Ile Ile  Asn Asn Thr Val Tyr  Asp Pro Leu Gln Pro  Glu Leu Asp
    1115                 1120                 1125

Ser Phe  Lys Glu Glu Leu Asp  Lys Tyr Phe Lys Asn  His Thr Ser
    1130                 1135                 1140

Pro Asp  Val Asp Leu Gly Asp  Ile Ser Gly Ile Asn  Ala Ser Val
    1145                 1150                 1155

Val Asn  Ile Gln Lys Glu Ile  Asp Arg Leu Asn Glu  Val Ala Lys
    1160                 1165                 1170

Asn Leu  Asn Glu Ser Leu Ile  Asp Leu Gln Glu Leu  Gly Lys Tyr
    1175                 1180                 1185

Glu Gln  Tyr Ile Lys Trp Pro  Trp Tyr Val Trp Leu  Gly Phe Ile
    1190                 1195                 1200

Ala Gly  Leu Ile Ala Ile Val  Met Val Thr Ile Leu  Leu Cys Cys
    1205                 1210                 1215

Met Thr  Ser Cys Cys Ser Cys  Leu Lys Gly Ala Cys  Ser Cys Gly
    1220                 1225                 1230

Ser Cys  Cys Lys Phe Asp Glu  Asp Asp Ser Glu Pro  Val Leu Lys
    1235                 1240                 1245

Gly Val  Lys Leu His Tyr Thr
    1250                 1255
```

<210> SEQ ID NO 4
<211> LENGTH: 1241

```
<212> TYPE: PRT
<213> ORGANISM: Artificial
<220> FEATURE:
<223> OTHER INFORMATION: SARS coronavirus

<400> SEQUENCE: 4

Met Lys Val Leu Ile Phe Ala Leu Leu Phe Ser Leu Ala Lys Ala Gln
1               5                   10                  15

Glu Gly Cys Gly Ile Ile Ser Arg Lys Pro Gln Pro Lys Met Glu Lys
            20                  25                  30

Val Ser Ser Ser Arg Arg Gly Val Tyr Tyr Asn Asp Asp Ile Phe Arg
        35                  40                  45

Ser Asp Val Leu His Leu Thr Gln Asp Tyr Phe Leu Pro Phe Asp Ser
    50                  55                  60

Asn Leu Thr Gln Tyr Phe Ser Leu Asn Ile Asp Ser Asn Lys Tyr Thr
65                  70                  75                  80

Tyr Phe Asp Asn Pro Ile Leu Asp Phe Gly Asp Gly Val Tyr Phe Ala
                85                  90                  95

Ala Thr Glu Lys Ser Asn Val Ile Arg Gly Trp Ile Phe Gly Ser Ser
            100                 105                 110

Phe Asp Asn Thr Thr Gln Ser Ala Ile Ile Val Asn Asn Ser Thr His
        115                 120                 125

Ile Ile Ile Arg Val Cys Asn Phe Asn Leu Cys Lys Glu Pro Met Tyr
    130                 135                 140

Thr Val Ser Lys Gly Thr Gln Gln Ser Ser Trp Val Tyr Gln Ser Ala
145                 150                 155                 160

Phe Asn Cys Thr Tyr Asp Arg Val Glu Lys Ser Phe Gln Leu Asp Thr
                165                 170                 175

Ala Pro Lys Thr Gly Asn Phe Lys Asp Leu Arg Glu Tyr Val Phe Lys
            180                 185                 190

Asn Arg Asp Gly Phe Leu Ser Val Tyr Gln Thr Tyr Thr Ala Val Asn
        195                 200                 205

Leu Pro Arg Gly Phe Pro Ala Gly Phe Ser Val Leu Arg Pro Ile Leu
    210                 215                 220

Lys Leu Pro Phe Gly Ile Asn Ile Thr Ser Tyr Arg Val Val Met Thr
225                 230                 235                 240

Met Phe Ser Gln Phe Asn Ser Asn Phe Leu Pro Glu Ser Ala Ala Tyr
                245                 250                 255

Tyr Val Gly Asn Leu Lys Tyr Thr Thr Phe Met Leu Ser Phe Asn Glu
            260                 265                 270

Asn Gly Thr Ile Thr Asp Ala Val Asp Cys Ser Gln Asn Pro Leu Ala
        275                 280                 285

Glu Leu Lys Cys Thr Ile Lys Asn Phe Asn Val Ser Lys Gly Ile Tyr
    290                 295                 300

Gln Thr Ser Asn Phe Arg Val Thr Pro Thr Gln Glu Val Val Arg Phe
305                 310                 315                 320

Pro Asn Ile Thr Asn Arg Cys Pro Phe Asp Lys Val Phe Asn Ala Ser
                325                 330                 335

Arg Phe Pro Asn Val Tyr Ala Trp Glu Arg Thr Lys Ile Ser Asp Cys
            340                 345                 350

Val Ala Asp Tyr Thr Val Leu Tyr Asn Ser Thr Ser Phe Ser Thr Phe
        355                 360                 365

Lys Cys Tyr Gly Val Ser Pro Ser Lys Leu Ile Asp Leu Cys Phe Thr
    370                 375                 380
```

-continued

Ser Val Tyr Ala Asp Thr Phe Leu Ile Arg Ser Ser Glu Val Arg Gln
385 390 395 400

Val Ala Pro Gly Glu Thr Gly Val Ile Ala Asp Tyr Asn Tyr Lys Leu
405 410 415

Pro Asp Asp Phe Thr Gly Cys Val Ile Ala Trp Asn Thr Ala Gln Gln
420 425 430

Asp Gln Gly Gln Tyr Tyr Tyr Arg Ser Tyr Arg Lys Glu Lys Leu Lys
435 440 445

Pro Phe Glu Arg Asp Leu Ser Ser Asp Glu Asn Gly Val Tyr Thr Leu
450 455 460

Ser Thr Tyr Asp Phe Tyr Pro Ser Ile Pro Val Glu Tyr Gln Ala Thr
465 470 475 480

Arg Val Val Val Leu Ser Phe Glu Leu Leu Asn Ala Pro Ala Thr Val
485 490 495

Cys Gly Pro Lys Leu Ser Thr Gln Leu Val Lys Asn Gln Cys Val Asn
500 505 510

Phe Asn Phe Asn Gly Leu Arg Gly Thr Gly Val Leu Thr Thr Ser Ser
515 520 525

Lys Arg Phe Gln Ser Phe Gln Gln Phe Gly Arg Asp Thr Ser Asp Phe
530 535 540

Thr Asp Ser Val Arg Asp Pro Gln Thr Leu Glu Ile Leu Asp Ile Ser
545 550 555 560

Pro Cys Ser Phe Gly Gly Val Ser Val Ile Thr Pro Gly Thr Asn Ala
565 570 575

Ser Ser Glu Val Ala Val Leu Tyr Gln Asp Val Asn Cys Thr Asp Val
580 585 590

Pro Thr Ser Ile His Ala Asp Gln Leu Thr Pro Ala Trp Arg Val Tyr
595 600 605

Ser Thr Gly Val Asn Val Phe Gln Thr Gln Ala Gly Cys Leu Ile Gly
610 615 620

Ala Glu His Val Asn Ala Ser Tyr Glu Cys Asp Ile Pro Ile Gly Ala
625 630 635 640

Gly Ile Cys Ala Ser Tyr His Thr Ala Ser Val Leu Arg Ser Thr Gly
645 650 655

Gln Lys Ser Ile Val Ala Tyr Thr Met Ser Leu Gly Ala Glu Asn Ser
660 665 670

Ile Ala Tyr Ala Asn Asn Ser Ile Ala Ile Pro Thr Asn Phe Ser Ile
675 680 685

Ser Val Thr Thr Glu Val Met Pro Val Ser Ile Ala Lys Thr Ser Val
690 695 700

Asp Cys Thr Met Tyr Ile Cys Gly Asp Ser Leu Glu Cys Ser Asn Leu
705 710 715 720

Leu Leu Gln Tyr Gly Ser Phe Cys Thr Gln Leu Asn Arg Ala Leu Thr
725 730 735

Gly Ile Ala Ile Glu Gln Asp Lys Asn Thr Gln Glu Val Phe Ala Gln
740 745 750

Val Lys Gln Met Tyr Lys Thr Pro Ala Ile Lys Asp Phe Gly Gly Phe
755 760 765

Asn Phe Ser Gln Ile Leu Pro Asp Pro Ser Lys Pro Thr Lys Arg Ser
770 775 780

Phe Ile Glu Asp Leu Leu Phe Asn Lys Val Thr Leu Ala Asp Ala Gly
785 790 795 800

Phe Met Lys Gln Tyr Gly Glu Cys Leu Gly Asp Ile Ser Ala Arg Asp

-continued

```
                805                 810                 815

Leu Ile Cys Ala Gln Lys Phe Asn Gly Leu Thr Val Leu Pro Pro Leu
            820                 825                 830

Leu Thr Asp Glu Met Ile Ala Ala Tyr Thr Ala Ala Leu Val Ser Gly
        835                 840                 845

Thr Ala Thr Ala Gly Trp Thr Phe Gly Ala Gly Ser Ala Leu Gln Ile
    850                 855                 860

Pro Phe Ala Met Gln Met Ala Tyr Arg Phe Asn Gly Ile Gly Val Thr
865                 870                 875                 880

Gln Asn Val Leu Tyr Glu Asn Gln Lys Gln Ile Ala Asn Gln Phe Asn
                885                 890                 895

Lys Ala Ile Ser Gln Ile Gln Glu Ser Leu Thr Thr Thr Ser Thr Ala
            900                 905                 910

Leu Gly Lys Leu Gln Asp Val Val Asn Asp Asn Ala Gln Ala Leu Asn
        915                 920                 925

Thr Leu Val Lys Gln Leu Ser Ser Asn Phe Gly Ala Ile Ser Ser Val
    930                 935                 940

Leu Asn Asp Ile Leu Ser Arg Leu Asp Lys Val Glu Ala Glu Val Gln
945                 950                 955                 960

Ile Asp Arg Leu Ile Thr Gly Arg Leu Gln Ser Leu Gln Thr Tyr Val
                965                 970                 975

Thr Gln Gln Leu Ile Arg Ala Ala Glu Ile Arg Ala Ser Ala Asn Leu
            980                 985                 990

Ala Ala Thr Lys Met Ser Glu Cys  Val Leu Gly Gln Ser  Lys Arg Val
        995                 1000                1005

Asp Phe  Cys Gly Lys Gly Tyr  His Leu Met Ser Phe  Pro Gln Ala
    1010                1015                1020

Ala Pro  His Gly Val Val Phe  Leu His Val Thr Tyr  Val Pro Ser
    1025                1030                1035

Gln Glu  Arg Asn Phe Thr Thr  Ala Pro Ala Ile Cys  His Glu Gly
    1040                1045                1050

Lys Ala  Tyr Phe Pro Arg Glu  Gly Val Phe Val Ser  Asn Gly Thr
    1055                1060                1065

Ser Trp  Phe Ile Thr Gln Arg  Asn Phe Tyr Ser Pro  Gln Ile Ile
    1070                1075                1080

Thr Thr  Asp Asn Thr Phe Val  Ala Gly Asn Cys Asp  Val Val Ile
    1085                1090                1095

Gly Ile  Ile Asn Asn Thr Val  Tyr Asp Pro Leu Gln  Pro Glu Leu
    1100                1105                1110

Asp Ser  Phe Lys Glu Glu Leu  Asp Lys Tyr Phe Lys  Asn His Thr
    1115                1120                1125

Ser Pro  Asp Val Asp Leu Gly  Asp Ile Ser Gly Ile  Asn Ala Ser
    1130                1135                1140

Val Val  Asn Ile Gln Lys Glu  Ile Asp Arg Leu Asn  Glu Val Ala
    1145                1150                1155

Lys Asn  Leu Asn Glu Ser Leu  Ile Asp Leu Gln Glu  Leu Gly Lys
    1160                1165                1170

Tyr Glu  Gln Tyr Ile Lys Trp  Pro Trp Tyr Val Trp  Leu Gly Phe
    1175                1180                1185

Ile Ala  Gly Leu Ile Ala Ile  Val Met Val Thr Ile  Leu Leu Cys
    1190                1195                1200

Cys Met  Thr Ser Cys Cys Ser  Cys Leu Lys Gly Ala  Cys Ser Cys
    1205                1210                1215
```

```
Gly Ser Cys Cys Lys Phe Asp Glu Asp Asp Ser Glu Pro Val Leu
    1220                1225                1230

Lys Gly Val Lys Leu His Tyr Thr
    1235                1240


<210> SEQ ID NO 5
<211> LENGTH: 1355
<212> TYPE: PRT
<213> ORGANISM: Artificial
<220> FEATURE:
<223> OTHER INFORMATION: chimeric coronavirus spike protein

<400> SEQUENCE: 5

Met Thr Leu Leu Met Cys Leu Leu Met Ser Leu Leu Ile Phe Val Arg
1               5                   10                  15

Gly Cys Asp Ser Gln Phe Val Asp Met Ser Pro Ala Ser Asn Thr Ser
            20                  25                  30

Glu Cys Leu Glu Ser Gln Val Asp Ala Ala Ala Phe Ser Lys Leu Met
        35                  40                  45

Trp Pro Tyr Pro Ile Asp Pro Ser Lys Val Asp Gly Ile Ile Tyr Pro
    50                  55                  60

Leu Gly Arg Thr Tyr Ser Asn Ile Thr Leu Ala Tyr Thr Gly Leu Phe
65                  70                  75                  80

Pro Leu Gln Gly Asp Leu Gly Ser Gln Tyr Leu Tyr Ser Val Ser His
                85                  90                  95

Ala Val Gly His Asp Gly Asp Pro Thr Lys Ala Tyr Ile Ser Asn Tyr
            100                 105                 110

Ser Leu Leu Val Asn Asp Phe Asp Asn Gly Phe Val Val Arg Ile Gly
        115                 120                 125

Ala Ala Ala Asn Ser Thr Gly Thr Ile Val Ile Ser Pro Ser Val Asn
    130                 135                 140

Thr Lys Ile Lys Lys Ala Tyr Pro Ala Phe Ile Leu Gly Ser Ser Leu
145                 150                 155                 160

Thr Asn Thr Ser Ala Gly Gln Pro Leu Tyr Ala Asn Tyr Ser Leu Thr
                165                 170                 175

Ile Ile Pro Asp Gly Cys Gly Thr Val Leu His Ala Phe Tyr Cys Ile
            180                 185                 190

Leu Lys Pro Arg Thr Val Asn Arg Cys Pro Ser Gly Thr Gly Tyr Val
        195                 200                 205

Ser Tyr Phe Ile Tyr Glu Thr Val His Asn Asp Cys Gln Ser Thr Ile
    210                 215                 220

Asn Arg Asn Ala Ser Leu Asn Ser Phe Lys Ser Phe Phe Asp Leu Val
225                 230                 235                 240

Asn Cys Thr Phe Phe Asn Ser Trp Asp Ile Thr Ala Asp Glu Thr Lys
                245                 250                 255

Glu Trp Phe Gly Ile Thr Gln Asp Thr Gln Gly Val His Leu Tyr Ser
            260                 265                 270

Ser Arg Lys Gly Asp Leu Tyr Gly Gly Asn Met Phe Arg Phe Ala Thr
        275                 280                 285

Leu Pro Val Tyr Glu Gly Ile Lys Tyr Tyr Thr Val Ile Pro Arg Ser
    290                 295                 300

Phe Arg Ser Lys Ala Asn Lys Arg Glu Ala Trp Ala Ala Phe Tyr Val
305                 310                 315                 320

Tyr Lys Leu His Gln Leu Thr Tyr Leu Leu Asp Phe Ser Val Asp Gly
                325                 330                 335
```

```
Tyr Ile Arg Arg Ala Ile Asp Cys Gly His Asp Asp Leu Ser Gln Leu
            340                 345                 350

His Cys Ser Tyr Thr Ser Phe Glu Val Asp Thr Gly Val Tyr Ser Val
        355                 360                 365

Ser Ser Tyr Glu Ala Lys Pro Ser Gly Ser Val Val Glu Gln Ala Glu
    370                 375                 380

Gly Val Glu Cys Asp Phe Ser Pro Leu Leu Ser Gly Thr Pro Pro Gln
385                 390                 395                 400

Val Tyr Asn Phe Lys Arg Leu Val Phe Thr Asn Cys Asn Tyr Asn Leu
                405                 410                 415

Thr Lys Leu Leu Ser Leu Phe Ser Val Asn Asp Phe Thr Cys Ser Gln
            420                 425                 430

Ile Ser Pro Ala Ala Ile Ala Ser Asn Cys Tyr Ser Ser Leu Ile Leu
        435                 440                 445

Asp Tyr Phe Ser Tyr Pro Leu Ser Met Lys Ser Asp Leu Ser Val Ser
    450                 455                 460

Ser Ala Gly Pro Ile Ser Gln Phe Asn Tyr Lys Gln Ser Phe Ser Asn
465                 470                 475                 480

Pro Thr Cys Leu Ile Leu Ala Thr Val Pro His Asn Leu Thr Thr Ile
                485                 490                 495

Thr Lys Pro Leu Lys Tyr Ser Tyr Ile Asn Lys Cys Ser Arg Leu Leu
            500                 505                 510

Ser Asp Asp Arg Thr Glu Val Pro Gln Leu Val Asn Ala Asn Gln Tyr
        515                 520                 525

Ser Pro Cys Val Ser Ile Val Pro Ser Thr Val Trp Glu Asp Gly Asp
    530                 535                 540

Tyr Tyr Arg Lys Gln Leu Ser Pro Leu Glu Gly Gly Gly Trp Leu Val
545                 550                 555                 560

Ala Ser Gly Ser Thr Val Ala Met Thr Glu Gln Leu Gln Met Gly Phe
                565                 570                 575

Gly Ile Thr Val Gln Tyr Gly Thr Asp Thr Asn Ser Val Cys Pro Lys
            580                 585                 590

Leu Asp Leu Gly Asp Ser Leu Thr Ile Thr Asn Arg Leu Gly Lys Cys
        595                 600                 605

Val Asp Tyr Ser Leu Tyr Gly Val Thr Gly Arg Gly Val Phe Gln Asn
    610                 615                 620

Cys Thr Ala Val Gly Val Lys Gln Gln Arg Phe Val Tyr Asp Ser Phe
625                 630                 635                 640

Asp Asn Leu Val Gly Tyr Tyr Ser Asp Asp Gly Asn Tyr Tyr Cys Val
                645                 650                 655

Arg Pro Cys Val Ser Val Pro Val Ser Val Ile Tyr Asp Lys Ser Thr
            660                 665                 670

Asn Leu His Ala Thr Leu Phe Gly Ser Val Ala Cys Glu His Val Thr
        675                 680                 685

Thr Met Met Ser Gln Phe Ser Arg Leu Thr Gln Ser Asn Leu Arg Arg
    690                 695                 700

Arg Asp Ser Asn Ile Pro Leu Gln Thr Ala Val Gly Cys Val Ile Gly
705                 710                 715                 720

Leu Ser Asn Asn Ser Leu Val Val Ser Asp Cys Lys Leu Pro Leu Gly
                725                 730                 735

Gln Ser Leu Cys Ala Val Pro Pro Val Ser Thr Phe Arg Ser Tyr Ser
            740                 745                 750
```

```
Ala Ser Gln Phe Gln Leu Ala Val Leu Asn Tyr Thr Ser Pro Ile Val
        755                 760                 765

Val Thr Pro Ile Asn Ser Ser Gly Phe Thr Ala Ala Ile Pro Thr Asn
    770                 775                 780

Phe Ser Phe Ser Val Thr Gln Glu Tyr Ile Glu Thr Ser Ile Gln Lys
785                 790                 795                 800

Val Thr Val Asp Cys Lys Gln Tyr Val Cys Asn Gly Phe Thr Arg Cys
                805                 810                 815

Glu Lys Leu Leu Val Glu Tyr Gly Gln Phe Cys Ser Lys Ile Asn Gln
            820                 825                 830

Ala Leu His Gly Ala Asn Leu Arg Gln Asp Glu Ser Val Tyr Ser Leu
        835                 840                 845

Tyr Ser Asn Ile Lys Thr Thr Ser Thr Gln Thr Leu Glu Tyr Gly Leu
    850                 855                 860

Asn Gly Asp Phe Asn Leu Thr Leu Leu Gln Val Pro Gln Ile Gly Gly
865                 870                 875                 880

Ser Ser Ser Ser Tyr Arg Ser Ala Ile Glu Asp Leu Leu Phe Asp Lys
                885                 890                 895

Val Thr Ile Ala Asp Pro Gly Tyr Met Gln Gly Tyr Asp Asp Cys Met
            900                 905                 910

Lys Gln Gly Pro Gln Ser Ala Arg Asp Leu Ile Cys Ala Gln Tyr Val
        915                 920                 925

Ser Gly Tyr Lys Val Leu Pro Pro Leu Tyr Asp Pro Asn Met Glu Ala
    930                 935                 940

Ala Tyr Thr Ser Ser Leu Leu Gly Ser Ile Ala Gly Ala Gly Trp Thr
945                 950                 955                 960

Ala Gly Leu Ser Ser Phe Ala Ala Ile Pro Phe Ala Gln Ser Met Phe
                965                 970                 975

Tyr Arg Leu Asn Gly Val Gly Ile Thr Gln Gln Val Leu Ser Glu Asn
            980                 985                 990

Gln Lys Ile Ile Ala Asn Lys Phe  Asn Gln Ala Leu Gly  Ala Met Gln
        995                 1000                1005

Thr Gly  Phe Thr Thr Thr Asn  Leu Ala Phe Asn Lys  Val Gln Asp
    1010                 1015                 1020

Ala Val  Asn Ala Asn Ala Met  Ala Leu Ser Lys Leu  Ala Ala Glu
    1025                 1030                 1035

Leu Ser  Asn Thr Phe Gly Ala  Ile Ser Ser Ser Ile  Ser Asp Ile
    1040                 1045                 1050

Leu Ala  Arg Leu Asp Thr Val  Glu Gln Glu Ala Gln  Ile Asp Arg
    1055                 1060                 1065

Leu Ile  Asn Gly Arg Leu Thr  Ser Leu Asn Ala Phe  Val Ala Gln
    1070                 1075                 1080

Gln Leu  Val Arg Thr Glu Ala  Ala Ala Arg Ser Ala  Gln Leu Ala
    1085                 1090                 1095

Gln Asp  Lys Val Asn Glu Cys  Val Lys Ser Gln Ser  Lys Arg Asn
    1100                 1105                 1110

Gly Phe  Cys Gly Thr Gly Thr  His Ile Val Ser Phe  Ala Ile Asn
    1115                 1120                 1125

Ala Pro  Asn Gly Leu Tyr Phe  Phe His Val Gly Tyr  Gln Pro Thr
    1130                 1135                 1140

Ser His  Val Asn Ala Thr Ala  Ala Tyr Gly Leu Cys  Asn Thr Glu
    1145                 1150                 1155

Asn Pro  Pro Lys Cys Ile Ala  Pro Ile Asp Gly Tyr  Phe Val Leu
```

```
    1160                1165                1170

Asn Gln  Thr Thr Ser Thr Ala  Arg Ser Ser Gly Asp  Gln His Trp
    1175                1180                1185

Tyr Tyr  Thr Gly Ser Ser Phe  Phe His Pro Glu Pro  Ile Thr Glu
    1190                1195                1200

Ala Asn  Ser Lys Tyr Val Ser  Met Asp Val Lys Phe  Glu Asn Leu
    1205                1210                1215

Thr Asn  Lys Leu Pro Pro Pro  Leu Leu Ser Asn Ser  Thr Asp Leu
    1220                1225                1230

Asp Phe  Lys Asp Glu Leu Glu  Glu Phe Phe Lys Asn  Val Ser Ser
    1235                1240                1245

Gln Gly  Pro Asn Phe Gln Glu  Ile Ser Lys Ile Asn  Thr Thr Leu
    1250                1255                1260

Leu Asn  Leu Asn Thr Glu Leu  Met Val Leu Ser Glu  Val Val Lys
    1265                1270                1275

Gln Leu  Asn Glu Ser Tyr Ile  Asp Leu Lys Glu Leu  Gly Asn Tyr
    1280                1285                1290

Thr Phe  Tyr Gln Lys Trp Pro  Trp Tyr Ile Trp Leu  Gly Phe Ile
    1295                1300                1305

Ala Gly  Leu Val Ala Leu Ala  Leu Cys Val Phe Phe  Ile Leu Cys
    1310                1315                1320

Cys Thr  Gly Cys Gly Thr Ser  Cys Leu Gly Lys Leu  Lys Cys Asn
    1325                1330                1335

Arg Cys  Cys Asp Ser Tyr Asp  Glu Tyr Glu Val Glu  Lys Ile His
    1340                1345                1350

Val His
    1355


<210> SEQ ID NO 6
<211> LENGTH: 1352
<212> TYPE: PRT
<213> ORGANISM: Artificial
<220> FEATURE:
<223> OTHER INFORMATION: Bat coronavirus

<400> SEQUENCE: 6

Met Thr Leu Leu Met Cys Leu Leu Met Ser Leu Leu Ile Phe Val Arg
1               5                   10                  15

Gly Cys Asp Ser Gln Phe Val Asp Met Ser Pro Ala Ser Asn Thr Ser
            20                  25                  30

Glu Cys Leu Glu Ser Gln Val Asp Ala Ala Ala Phe Ser Lys Leu Met
        35                  40                  45

Trp Pro Tyr Pro Ile Asp Pro Ser Lys Val Asp Gly Ile Ile Tyr Pro
    50                  55                  60

Leu Gly Arg Thr Tyr Ser Asn Ile Thr Leu Ala Tyr Thr Gly Leu Phe
65                  70                  75                  80

Pro Leu Gln Gly Asp Leu Gly Ser Gln Tyr Leu Tyr Ser Val Ser His
                85                  90                  95

Ala Val Gly His Asp Gly Asp Pro Thr Lys Ala Tyr Ile Ser Asn Tyr
            100                 105                 110

Ser Leu Leu Val Asn Asp Phe Asp Asn Gly Phe Val Val Arg Ile Gly
        115                 120                 125

Ala Ala Ala Asn Ser Thr Gly Thr Ile Val Ile Ser Pro Ser Val Asn
    130                 135                 140

Thr Lys Ile Lys Lys Ala Tyr Pro Ala Phe Ile Leu Gly Ser Ser Leu
```

-continued

```
145                 150                 155                 160

Thr Asn Thr Ser Ala Gly Gln Pro Leu Tyr Ala Asn Tyr Ser Leu Thr
                165                 170                 175

Ile Ile Pro Asp Gly Cys Gly Thr Val Leu His Ala Phe Tyr Cys Ile
            180                 185                 190

Leu Lys Pro Arg Thr Val Asn Arg Cys Pro Ser Gly Thr Gly Tyr Val
        195                 200                 205

Ser Tyr Phe Ile Tyr Glu Thr Val His Asn Asp Cys Gln Ser Thr Ile
    210                 215                 220

Asn Arg Asn Ala Ser Leu Asn Ser Phe Lys Ser Phe Phe Asp Leu Val
225                 230                 235                 240

Asn Cys Thr Phe Phe Asn Ser Trp Asp Ile Thr Ala Asp Glu Thr Lys
                245                 250                 255

Glu Trp Phe Gly Ile Thr Gln Asp Thr Gln Gly Val His Leu Tyr Ser
            260                 265                 270

Ser Arg Lys Gly Asp Leu Tyr Gly Gly Asn Met Phe Arg Phe Ala Thr
        275                 280                 285

Leu Pro Val Tyr Glu Gly Ile Lys Tyr Tyr Thr Val Ile Pro Arg Ser
    290                 295                 300

Phe Arg Ser Lys Ala Asn Lys Arg Glu Ala Trp Ala Ala Phe Tyr Val
305                 310                 315                 320

Tyr Lys Leu His Gln Leu Thr Tyr Leu Leu Asp Phe Ser Val Asp Gly
                325                 330                 335

Tyr Ile Arg Arg Ala Ile Asp Cys Gly His Asp Asp Leu Ser Gln Leu
            340                 345                 350

His Cys Ser Tyr Thr Ser Phe Glu Val Asp Thr Gly Val Tyr Ser Val
        355                 360                 365

Ser Ser Tyr Glu Ala Ser Ala Thr Gly Thr Phe Ile Glu Gln Pro Asn
    370                 375                 380

Ala Thr Glu Cys Asp Phe Ser Pro Met Leu Thr Gly Val Ala Pro Gln
385                 390                 395                 400

Val Tyr Asn Phe Lys Arg Leu Val Phe Ser Asn Cys Asn Tyr Asn Leu
                405                 410                 415

Thr Lys Leu Leu Ser Leu Phe Ala Val Asp Glu Phe Ser Cys Asn Gly
            420                 425                 430

Ile Ser Pro Asp Ala Ile Ala Arg Gly Cys Tyr Ser Thr Leu Thr Val
        435                 440                 445

Asp Tyr Phe Ala Tyr Pro Leu Ser Met Lys Ser Tyr Ile Arg Pro Gly
    450                 455                 460

Ser Ala Gly Asn Ile Pro Leu Tyr Asn Tyr Lys Gln Ser Phe Ala Asn
465                 470                 475                 480

Pro Thr Cys Arg Val Met Ala Ser Val Leu Ala Asn Val Thr Ile Thr
                485                 490                 495

Lys Pro His Ala Tyr Gly Tyr Ile Ser Lys Cys Ser Arg Leu Thr Gly
            500                 505                 510

Ala Asn Gln Asp Val Glu Thr Pro Leu Tyr Ile Asn Pro Gly Glu Tyr
        515                 520                 525

Ser Ile Cys Arg Asp Phe Ser Pro Gly Gly Phe Ser Glu Asp Gly Gln
    530                 535                 540

Val Phe Lys Arg Thr Leu Thr Gln Phe Glu Gly Gly Gly Leu Leu Ile
545                 550                 555                 560

Gly Val Gly Thr Arg Val Pro Met Thr Asp Asn Leu Gln Met Ser Phe
                565                 570                 575
```

```
Ile Ile Ser Val Gln Tyr Gly Thr Gly Thr Asp Ser Val Cys Pro Met
            580                 585                 590

Leu Asp Leu Gly Asp Ser Leu Thr Ile Thr Asn Arg Leu Gly Lys Cys
        595                 600                 605

Val Asp Tyr Ser Leu Tyr Gly Val Thr Gly Arg Gly Val Phe Gln Asn
    610                 615                 620

Cys Thr Ala Val Gly Val Lys Gln Gln Arg Phe Val Tyr Asp Ser Phe
625                 630                 635                 640

Asp Asn Leu Val Gly Tyr Tyr Ser Asp Asp Gly Asn Tyr Tyr Cys Val
                645                 650                 655

Arg Pro Cys Val Ser Val Pro Val Ser Val Ile Tyr Asp Lys Ser Thr
            660                 665                 670

Asn Leu His Ala Thr Leu Phe Gly Ser Val Ala Cys Glu His Val Thr
        675                 680                 685

Thr Met Met Ser Gln Phe Ser Arg Leu Thr Gln Ser Asn Leu Arg Arg
    690                 695                 700

Arg Asp Ser Asn Ile Pro Leu Gln Thr Ala Val Gly Cys Val Ile Gly
705                 710                 715                 720

Leu Ser Asn Asn Ser Leu Val Val Ser Asp Cys Lys Leu Pro Leu Gly
                725                 730                 735

Gln Ser Leu Cys Ala Val Pro Pro Val Ser Thr Phe Arg Ser Tyr Ser
            740                 745                 750

Ala Ser Gln Phe Gln Leu Ala Val Leu Asn Tyr Thr Ser Pro Ile Val
        755                 760                 765

Val Thr Pro Ile Asn Ser Ser Gly Phe Thr Ala Ala Ile Pro Thr Asn
    770                 775                 780

Phe Ser Phe Ser Val Thr Gln Glu Tyr Ile Glu Thr Ser Ile Gln Lys
785                 790                 795                 800

Val Thr Val Asp Cys Lys Gln Tyr Val Cys Asn Gly Phe Thr Arg Cys
                805                 810                 815

Glu Lys Leu Leu Val Glu Tyr Gly Gln Phe Cys Ser Lys Ile Asn Gln
            820                 825                 830

Ala Leu His Gly Ala Asn Leu Arg Gln Asp Glu Ser Val Tyr Ser Leu
        835                 840                 845

Tyr Ser Asn Ile Lys Thr Thr Ser Thr Gln Thr Leu Glu Tyr Gly Leu
    850                 855                 860

Asn Gly Asp Phe Asn Leu Thr Leu Leu Gln Val Pro Gln Ile Gly Gly
865                 870                 875                 880

Ser Ser Ser Ser Tyr Arg Ser Ala Ile Glu Asp Leu Leu Phe Asp Lys
                885                 890                 895

Val Thr Ile Ala Asp Pro Gly Tyr Met Gln Gly Tyr Asp Asp Cys Met
            900                 905                 910

Lys Gln Gly Pro Gln Ser Ala Arg Asp Leu Ile Cys Ala Gln Tyr Val
        915                 920                 925

Ser Gly Tyr Lys Val Leu Pro Pro Leu Tyr Asp Pro Asn Met Glu Ala
    930                 935                 940

Ala Tyr Thr Ser Ser Leu Leu Gly Ser Ile Ala Gly Ala Gly Trp Thr
945                 950                 955                 960

Ala Gly Leu Ser Ser Phe Ala Ala Ile Pro Phe Ala Gln Ser Met Phe
                965                 970                 975

Tyr Arg Leu Asn Gly Val Gly Ile Thr Gln Gln Val Leu Ser Glu Asn
            980                 985                 990
```

```
Gln Lys Leu Ile Ala Asn Lys Phe  Asn Gln Ala Leu Gly  Ala Met Gln
        995                 1000                 1005

Thr Gly  Phe Thr Thr Ser Asn  Leu Ala Phe Ser Lys  Val Gln Asp
    1010                 1015                 1020

Ala Val  Asn Ala Asn Ala Gln  Ala Leu Ser Lys Leu  Ala Ser Glu
    1025                 1030                 1035

Leu Ser  Asn Thr Phe Gly Ala  Ile Ser Ser Ser Ile  Ser Asp Ile
    1040                 1045                 1050

Leu Ala  Arg Leu Asp Thr Val  Glu Gln Asp Ala Gln  Ile Asp Arg
    1055                 1060                 1065

Leu Ile  Asn Gly Arg Leu Thr  Ser Leu Asn Ala Phe  Val Ser Gln
    1070                 1075                 1080

Gln Leu  Val Arg Ser Glu Thr  Ala Ala Arg Ser Ala  Gln Leu Ala
    1085                 1090                 1095

Ser Asp  Lys Val Asn Glu Cys  Val Lys Ser Gln Ser  Lys Arg Asn
    1100                 1105                 1110

Gly Phe  Cys Gly Ser Gly Thr  His Ile Val Ser Phe  Val Val Asn
    1115                 1120                 1125

Ala Pro  Asn Gly Phe Tyr Phe  Phe His Val Gly Tyr  Val Pro Thr
    1130                 1135                 1140

Asn Tyr  Thr Asn Val Thr Ala  Ala Tyr Gly Leu Cys  Asn Asn Asn
    1145                 1150                 1155

Asn Pro  Pro Leu Cys Ile Ala  Pro Ile Asp Gly Tyr  Phe Ile Thr
    1160                 1165                 1170

Asn Gln  Thr Thr Thr Tyr Ser  Val Asp Thr Glu Trp  Tyr Tyr Thr
    1175                 1180                 1185

Gly Ser  Ser Phe Tyr Lys Pro  Glu Pro Ile Thr Gln  Ala Asn Ser
    1190                 1195                 1200

Arg Tyr  Val Ser Ser Asp Val  Lys Phe Asp Lys Leu  Glu Asn Asn
    1205                 1210                 1215

Leu Pro  Pro Pro Leu Leu Glu  Asn Ser Thr Asp Val  Asp Phe Lys
    1220                 1225                 1230

Asp Glu  Leu Glu Glu Phe Phe  Lys Asn Val Thr Ser  His Gly Pro
    1235                 1240                 1245

Asn Phe  Ala Glu Ile Ser Lys  Ile Asn Thr Thr Leu  Leu Asp Leu
    1250                 1255                 1260

Ser Asp  Glu Met Ala Met Leu  Gln Glu Val Val Lys  Gln Leu Asn
    1265                 1270                 1275

Asp Ser  Tyr Ile Asp Leu Lys  Glu Leu Gly Asn Tyr  Thr Tyr Tyr
    1280                 1285                 1290

Asn Lys  Trp Pro Trp Tyr Val  Trp Leu Gly Phe Ile  Ala Gly Leu
    1295                 1300                 1305

Val Ala  Leu Leu Leu Cys Val  Phe Phe Leu Leu Cys  Cys Thr Gly
    1310                 1315                 1320

Cys Gly  Thr Ser Cys Leu Gly  Lys Met Lys Cys Lys  Asn Cys Cys
    1325                 1330                 1335

Asp Ser  Tyr Glu Glu Tyr Asp  Val Glu Lys Ile His  Val His
    1340                 1345                 1350
```

<210> SEQ ID NO 7
<211> LENGTH: 1353
<212> TYPE: PRT
<213> ORGANISM: Artificial
<220> FEATURE:
<223> OTHER INFORMATION: MERS coronavirus -continued

<400> SEQUENCE: 7

Met Ile His Ser Val Phe Leu Leu Met Phe Leu Leu Thr Pro Thr Glu
1 5 10 15

Ser Tyr Val Asp Val Gly Pro Asp Ser Val Lys Ser Ala Cys Ile Glu
20 25 30

Val Asp Ile Gln Gln Thr Phe Phe Asp Lys Thr Trp Pro Arg Pro Ile
35 40 45

Asp Val Ser Lys Ala Asp Gly Ile Ile Tyr Pro Gln Gly Arg Thr Tyr
50 55 60

Ser Asn Ile Thr Ile Thr Tyr Gln Gly Leu Phe Pro Tyr Gln Gly Asp
65 70 75 80

His Gly Asp Met Tyr Val Tyr Ser Ala Gly His Ala Thr Gly Thr Thr
85 90 95

Pro Gln Lys Leu Phe Val Ala Asn Tyr Ser Gln Asp Val Lys Gln Phe
100 105 110

Ala Asn Gly Phe Val Val Arg Ile Gly Ala Ala Ala Asn Ser Thr Gly
115 120 125

Thr Val Ile Ile Ser Pro Ser Thr Ser Ala Thr Ile Arg Lys Ile Tyr
130 135 140

Pro Ala Phe Met Leu Gly Ser Ser Val Gly Asn Phe Ser Asp Gly Lys
145 150 155 160

Met Gly Arg Phe Phe Asn His Thr Leu Val Leu Leu Pro Asp Gly Cys
165 170 175

Gly Thr Leu Leu Arg Ala Phe Tyr Cys Ile Leu Glu Pro Arg Ser Gly
180 185 190

Asn His Cys Pro Ala Gly Asn Ser Tyr Thr Ser Phe Ala Thr Tyr His
195 200 205

Thr Pro Ala Thr Asp Cys Ser Asp Gly Asn Tyr Asn Arg Asn Ala Ser
210 215 220

Leu Asn Ser Phe Lys Glu Tyr Phe Asn Leu Arg Asn Cys Thr Phe Met
225 230 235 240

Tyr Thr Tyr Asn Ile Thr Glu Asp Glu Ile Leu Glu Trp Phe Gly Ile
245 250 255

Thr Gln Thr Ala Gln Gly Val His Leu Phe Ser Ser Arg Tyr Val Asp
260 265 270

Leu Tyr Gly Gly Asn Met Phe Gln Phe Ala Thr Leu Pro Val Tyr Asp
275 280 285

Thr Ile Lys Tyr Tyr Ser Ile Ile Pro His Ser Ile Arg Ser Ile Gln
290 295 300

Ser Asp Arg Lys Ala Trp Ala Ala Phe Tyr Val Tyr Lys Leu Gln Pro
305 310 315 320

Leu Thr Phe Leu Leu Asp Phe Ser Val Asp Gly Tyr Ile Arg Arg Ala
325 330 335

Ile Asp Cys Gly Phe Asn Asp Leu Ser Gln Leu His Cys Ser Tyr Glu
340 345 350

Ser Phe Asp Val Glu Ser Gly Val Tyr Ser Val Ser Ser Phe Glu Ala
355 360 365

Lys Pro Ser Gly Ser Val Val Glu Gln Ala Glu Gly Val Glu Cys Asp
370 375 380

Phe Ser Pro Leu Leu Ser Gly Thr Pro Pro Gln Val Tyr Asn Phe Lys
385 390 395 400

Arg Leu Val Phe Thr Asn Cys Asn Tyr Asn Leu Thr Lys Leu Leu Ser

-continued

```
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830
```

-continued

```
Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys  Phe Asn Gln Ala Leu  Gly Ala Met
        995                 1000                1005

Gln Thr  Gly Phe Thr Thr Thr  Asn Glu Ala Phe Gln  Lys Val Gln
    1010                 1015                 1020

Asp Ala  Val Asn Asn Asn Ala  Gln Ala Leu Ser Lys  Leu Ala Ser
    1025                 1030                 1035

Glu Leu  Ser Asn Thr Phe Gly  Ala Ile Ser Ala Ser  Ile Gly Asp
    1040                 1045                 1050

Ile Ile  Gln Arg Leu Asp Val  Leu Glu Gln Asp Ala  Gln Ile Asp
    1055                 1060                 1065

Arg Leu  Ile Asn Gly Arg Leu  Thr Thr Leu Asn Ala  Phe Val Ala
    1070                 1075                 1080

Gln Gln  Leu Val Arg Ser Glu  Ser Ala Ala Leu Ser  Ala Gln Leu
    1085                 1090                 1095

Ala Lys  Asp Lys Val Asn Glu  Cys Val Lys Ala Gln  Ser Lys Arg
    1100                 1105                 1110

Ser Gly  Phe Cys Gly Gln Gly  Thr His Ile Val Ser  Phe Val Val
    1115                 1120                 1125

Asn Ala  Pro Asn Gly Leu Tyr  Phe Met His Val Gly  Tyr Tyr Pro
    1130                 1135                 1140

Ser Asn  His Ile Glu Val Val  Ser Ala Tyr Gly Leu  Cys Asp Ala
    1145                 1150                 1155

Ala Asn  Pro Thr Asn Cys Ile  Ala Pro Val Asn Gly  Tyr Phe Ile
    1160                 1165                 1170

Lys Thr  Asn Asn Thr Arg Ile  Val Asp Glu Trp Ser  Tyr Thr Gly
    1175                 1180                 1185

Ser Ser  Phe Tyr Ala Pro Glu  Pro Ile Thr Ser Leu  Asn Thr Lys
    1190                 1195                 1200

Tyr Val  Ala Pro Gln Val Thr  Tyr Gln Asn Ile Ser  Thr Asn Leu
    1205                 1210                 1215

Pro Pro  Pro Leu Leu Gly Asn  Ser Thr Gly Ile Asp  Phe Gln Asp
    1220                 1225                 1230
```

Glu Leu Asp Glu Phe Phe Lys Asn Val Ser Thr Ser Ile Pro Asn
1235 1240 1245

Phe Gly Ser Leu Thr Gln Ile Asn Thr Thr Leu Leu Asp Leu Thr
1250 1255 1260

Tyr Glu Met Leu Ser Leu Gln Gln Val Val Lys Ala Leu Asn Glu
1265 1270 1275

Ser Tyr Ile Asp Leu Lys Glu Leu Gly Asn Tyr Thr Tyr Tyr Asn
1280 1285 1290

Lys Trp Pro Trp Tyr Ile Trp Leu Gly Phe Ile Ala Gly Leu Val
1295 1300 1305

Ala Leu Ala Leu Cys Val Phe Phe Ile Leu Cys Cys Thr Gly Cys
1310 1315 1320

Gly Thr Asn Cys Met Gly Lys Leu Lys Cys Asn Arg Cys Cys Asp
1325 1330 1335

Arg Tyr Glu Glu Tyr Asp Leu Glu Pro His Lys Val His Val His
1340 1345 1350

<210> SEQ ID NO 8
<211> LENGTH: 1357
<212> TYPE: PRT
<213> ORGANISM: Artificial
<220> FEATURE:
<223> OTHER INFORMATION: Bat coronavirus

<400> SEQUENCE: 8

Met Ile Arg Ser Val Leu Val Leu Met Cys Ser Leu Thr Phe Ile Gly
1 5 10 15

Asn Arg Thr Ser Cys Gln Ser Val Asp Ile Gly Thr Pro Val Thr Gly
20 25 30

Ser Cys Leu Arg Ser Gln Val Arg Pro Glu Tyr Phe Asp Ile Val His
35 40 45

Asn Thr Trp Pro Met Pro Ile Asp Thr Ser Lys Ala Glu Gly Val Ile
50 55 60

Tyr Pro Asn Gly Lys Ser Tyr Ser Asn Ile Ser Leu Thr Tyr Thr Gly
65 70 75 80

Leu Tyr Pro Lys Ala Lys Asp Leu Gly Lys Gln Tyr Leu Phe Ser Asp
85 90 95

Gly His Ser Ala Pro Asn Gln Leu Asn Asp Leu Phe Val Ser Asn Tyr
100 105 110

Ser Ala Gln Val Glu Ser Phe Asp Asp Gly Phe Val Val Arg Ile Gly
115 120 125

Ala Ala Ser Asn Lys Thr Gly Thr Thr Val Ile Ser Gln Thr Thr Phe
130 135 140

Lys Pro Ile Lys Lys Ile Tyr Pro Gly Phe Met Leu Gly His Ala Val
145 150 155 160

Gly Asn Tyr Thr Pro Thr Asn Ile Thr Gly Arg Tyr Leu Asn His Thr
165 170 175

Leu Val Ile Leu Pro Asp Gly Cys Gly Thr Leu Val His Ala Phe Tyr
180 185 190

Cys Ile Leu Gln Pro Arg Thr Gln Ala Asn Cys Pro Gly Ala Ser Ser
195 200 205

Phe Thr Ser Val Thr Leu Trp Asp Thr Pro Ala Thr Asp Cys Ala Pro
210 215 220

Ser Gly Val Tyr Asn Ser Leu Ala Asn Leu Asn Ala Phe Lys Leu Tyr
225 230 235 240

-continued

```
Phe Asp Leu Ile Asn Cys Thr Phe Arg Tyr Asn Tyr Thr Ile Thr Glu
                245                 250                 255

Asp Glu Asn Ala Glu Trp Phe Gly Ile Thr Gln Asp Thr Gln Gly Val
            260                 265                 270

His Leu Tyr Ser Ser Arg Lys Glu Asn Val Phe Arg Asn Asn Met Phe
        275                 280                 285

His Phe Ala Thr Leu Pro Val Tyr Gln Lys Ile Leu Tyr Tyr Thr Val
    290                 295                 300

Ile Pro Arg Ser Ile Arg Ser Pro Phe Asn Asp Arg Lys Ala Trp Ala
305                 310                 315                 320

Ala Phe Tyr Ile Tyr Lys Leu His Pro Leu Thr Tyr Leu Leu Asn Phe
                325                 330                 335

Asp Val Glu Gly Tyr Ile Thr Lys Ala Val Asp Cys Gly Tyr Asp Asp
            340                 345                 350

Phe Ala Gln Leu Gln Cys Ser Tyr Glu Asn Phe Asp Val Glu Thr Gly
        355                 360                 365

Val Tyr Ser Val Ser Ser Phe Glu Ala Ser Pro Arg Gly Glu Phe Ile
    370                 375                 380

Glu Gln Ala Thr Thr Gln Glu Cys Asp Phe Thr Pro Met Leu Thr Gly
385                 390                 395                 400

Thr Pro Pro Pro Ile Tyr Asp Phe Lys Arg Leu Val Phe Thr Asn Cys
                405                 410                 415

Asn Tyr Asn Leu Thr Lys Leu Leu Ser Leu Phe Gln Val Ser Glu Phe
            420                 425                 430

Ser Cys His Gln Val Ser Pro Ser Ser Leu Ala Thr Gly Cys Tyr Ser
        435                 440                 445

Ser Leu Thr Val Asp Tyr Phe Ala Tyr Ser Thr Asp Met Ser Ser Tyr
    450                 455                 460

Leu Gln Pro Gly Ser Ala Gly Glu Ile Val Gln Phe Asn Tyr Lys Gln
465                 470                 475                 480

Asp Phe Ser Asn Pro Thr Cys Arg Val Leu Ala Thr Val Pro Thr Asn
                485                 490                 495

Leu Thr Thr Ile Thr Lys Ser Ser Asn Tyr Val His Leu Thr Glu Cys
            500                 505                 510

Tyr Lys Ser Thr Ala Tyr Gly Lys Asn Tyr Leu Tyr Asn Ala Pro Gly
        515                 520                 525

Gly Tyr Thr Pro Cys Leu Ser Leu Ala Ser Arg Gly Phe Thr Thr Asn
    530                 535                 540

Arg Gln Ser His Ser Leu Glu Leu Pro Asp Gly Tyr Leu Val Thr Thr
545                 550                 555                 560

Gly Ser Val Tyr Pro Val Asn Gly Asn Leu Gln Met Ala Phe Ile Ile
                565                 570                 575

Ser Val Gln Tyr Gly Thr Asp Thr Asn Ser Val Cys Pro Met Gln Ala
            580                 585                 590

Leu Arg Asn Asp Thr Ser Ile Glu Asp Lys Leu Asp Val Cys Val Glu
        595                 600                 605

Tyr Ser Leu His Gly Ile Thr Gly Arg Gly Val Phe His Asn Cys Thr
    610                 615                 620

Ser Val Gly Leu Arg Asn Gln Arg Phe Val Tyr Asp Thr Phe Asp Asn
625                 630                 635                 640

Leu Val Gly Tyr His Ser Asp Asn Gly Asn Tyr Tyr Cys Val Arg Pro
                645                 650                 655

Cys Val Ser Val Pro Val Ser Val Ile Tyr Asp Lys Ala Ser Asn Ser
```

-continued

```
            660                 665                 670

His Ala Thr Leu Phe Gly Ser Val Ala Cys Ser His Val Thr Thr Met
        675                 680                 685

Met Ser Gln Phe Ser Arg Met Thr Lys Thr Asn Leu Pro Ala Arg Thr
    690                 695                 700

Thr Pro Gly Pro Leu Gln Thr Thr Val Gly Cys Ala Met Gly Phe Ile
705                 710                 715                 720

Asn Ser Ser Met Val Val Asp Glu Cys Gln Leu Pro Leu Gly Gln Ser
                725                 730                 735

Leu Cys Ala Ile Pro Pro Thr Thr Ser Thr Arg Phe Arg Arg Ala Thr
            740                 745                 750

Ser Ile Pro Asp Val Phe Gln Ile Ala Thr Leu Asn Phe Thr Ser Pro
        755                 760                 765

Leu Thr Leu Ala Pro Ile Asn Ser Thr Gly Phe Val Val Ala Val Pro
    770                 775                 780

Thr Asn Phe Thr Phe Gly Val Thr Gln Glu Phe Ile Glu Thr Thr Ile
785                 790                 795                 800

Gln Lys Ile Thr Val Asp Cys Lys Gln Tyr Val Cys Asn Gly Phe Lys
                805                 810                 815

Lys Cys Glu Asp Leu Leu Lys Glu Tyr Gly Gln Phe Cys Ser Lys Ile
            820                 825                 830

Asn Gln Ala Leu His Gly Ala Asn Leu Arg Gln Asp Glu Ser Ile Ala
        835                 840                 845

Asn Leu Phe Ser Ser Ile Lys Thr Gln Asn Thr Gln Pro Leu Gln Ala
    850                 855                 860

Gly Leu Asn Gly Asp Phe Asn Leu Thr Met Leu Gln Ile Pro Gln Val
865                 870                 875                 880

Thr Thr Gly Glu Arg Lys Tyr Arg Ser Thr Ile Glu Asp Leu Leu Phe
                885                 890                 895

Asn Lys Val Thr Ile Ala Asp Pro Gly Tyr Met Gln Gly Tyr Asp Glu
            900                 905                 910

Cys Met Gln Gln Gly Pro Gln Ser Ala Arg Asp Leu Ile Cys Ala Gln
        915                 920                 925

Tyr Val Ala Gly Tyr Lys Val Leu Pro Pro Leu Tyr Asp Pro Tyr Met
    930                 935                 940

Glu Ala Ala Tyr Thr Ser Ser Leu Leu Gly Ser Ile Ala Gly Ala Ser
945                 950                 955                 960

Trp Thr Ala Gly Leu Ser Ser Phe Ala Ala Ile Pro Phe Ala Gln Ser
                965                 970                 975

Ile Phe Tyr Arg Leu Asn Gly Val Gly Ile Thr Gln Gln Val Leu Ser
            980                 985                 990

Glu Asn Gln Lys Ile Ile Ala Asn  Lys Phe Asn Gln Ala  Leu Gly Ala
        995                 1000                 1005

Met Gln  Thr Gly Phe Thr Thr  Thr Asn Leu Ala Phe  Asn Lys Val
    1010                 1015                 1020

Gln Asp  Ala Val Asn Ala Asn  Ala Met Ala Leu Ser  Lys Leu Ala
    1025                 1030                 1035

Ala Glu  Leu Ser Asn Thr Phe  Gly Ala Ile Ser Ser  Ser Ile Ser
    1040                 1045                 1050

Asp Ile  Leu Ala Arg Leu Asp  Thr Val Glu Gln Glu  Ala Gln Ile
    1055                 1060                 1065

Asp Arg  Leu Ile Asn Gly Arg  Leu Thr Ser Leu Asn  Ala Phe Val
    1070                 1075                 1080
```

-continued

```
Ala Gln  Gln Leu Val Arg Thr  Glu Ala Ala Ala Arg  Ser Ala Gln
    1085                 1090                 1095

Leu Ala  Gln Asp Lys Val Asn  Glu Cys Val Lys Ser  Gln Ser Lys
    1100                 1105                 1110

Arg Asn  Gly Phe Cys Gly Thr  Gly Thr His Ile Val  Ser Phe Ala
    1115                 1120                 1125

Ile Asn  Ala Pro Asn Gly Leu  Tyr Phe Phe His Val  Gly Tyr Gln
    1130                 1135                 1140

Pro Thr  Ser His Val Asn Ala  Thr Ala Ala Tyr Gly  Leu Cys Asn
    1145                 1150                 1155

Thr Glu  Asn Pro Pro Lys Cys  Ile Ala Pro Ile Asp  Gly Tyr Phe
    1160                 1165                 1170

Val Leu  Asn Gln Thr Thr Ser  Thr Ala Arg Ser Ser  Gly Asp Gln
    1175                 1180                 1185

His Trp  Tyr Tyr Thr Gly Ser  Ser Phe Phe His Pro  Glu Pro Ile
    1190                 1195                 1200

Thr Glu  Ala Asn Ser Lys Tyr  Val Ser Met Asp Val  Lys Phe Glu
    1205                 1210                 1215

Asn Leu  Thr Asn Lys Leu Pro  Pro Pro Leu Leu Ser  Asn Ser Thr
    1220                 1225                 1230

Asp Leu  Asp Phe Lys Asp Glu  Leu Glu Glu Phe Phe  Lys Asn Val
    1235                 1240                 1245

Ser Ser  Gln Gly Pro Asn Phe  Gln Glu Ile Ser Lys  Ile Asn Thr
    1250                 1255                 1260

Thr Leu  Leu Asn Leu Asn Thr  Glu Leu Met Val Leu  Ser Glu Val
    1265                 1270                 1275

Val Lys  Gln Leu Asn Glu Ser  Tyr Ile Asp Leu Lys  Glu Leu Gly
    1280                 1285                 1290

Asn Tyr  Thr Phe Tyr Gln Lys  Trp Pro Trp Tyr Ile  Trp Leu Gly
    1295                 1300                 1305

Phe Ile  Ala Gly Leu Val Ala  Leu Ala Leu Cys Val  Phe Phe Ile
    1310                 1315                 1320

Leu Cys  Cys Thr Gly Cys Gly  Thr Ser Cys Leu Gly  Lys Leu Lys
    1325                 1330                 1335

Cys Asn  Arg Cys Cys Asp Ser  Tyr Asp Glu Tyr Glu  Val Glu Lys
    1340                 1345                 1350

Ile His  Val His
    1355
```